United States Patent [19]
Winkler et al.

[11] Patent Number: 5,648,373
[45] Date of Patent: Jul. 15, 1997

[54] COA-IT AND PAF INHIBITORS

[75] Inventors: James David Winkler, Fort Washington, Pa.; Floyd Harold Chilton, III, Pilot Mountain, N.C.; Deirdre Mary Bernadette Hickey, Welwyn, England

[73] Assignees: SmithKline Beecham Corporation, Philadelphia, Pa.; The Johns Hopkins University, Baltimore, Md.

[21] Appl. No.: 102,877

[22] Filed: Aug. 6, 1993

Related U.S. Application Data

[63] Continuation-in-part of PCT/US93/01247, Feb. 11, 1993, which is a continuation-in-part of Ser. No. 833,850, Feb. 11, 1992, abandoned, Ser. No. 833,877, Feb. 11, 1992, abandoned, Ser. No. 833,878, Feb. 11, 1992, abandoned, Ser. No. 833,879, Feb. 11, 1992, abandoned, Ser. No. 833,880, Feb. 11, 1992, abandoned, and Ser. No. 834,048, Feb. 11, 1992, abandoned.

[30] Foreign Application Priority Data

Feb. 11, 1992 [GB] United Kingdom .......... 9202827

[51] Int. Cl.$^6$ .......... A61K 31/415
[52] U.S. Cl. .......... 514/398; 514/359; 514/374; 514/392; 514/397; 514/406; 514/425; 514/825; 514/826; 514/863; 514/916; 514/921
[58] Field of Search .......... 514/392, 397, 514/398, 359, 406, 374, 425, 825, 826, 863, 916, 921

[56] References Cited

U.S. PATENT DOCUMENTS

| | | | |
|---|---|---|---|
| 3,021,338 | 2/1962 | Bortnick | 548/323.5 X |
| 4,355,039 | 10/1982 | Niedballa et al. | 548/323.5 X |
| 5,087,634 | 2/1992 | Reitz et al. | 514/381 |
| 5,248,689 | 9/1993 | Girard et al. | 514/397 |
| 5,256,695 | 10/1993 | Poss | 514/563 |
| 5,338,752 | 8/1994 | Hickey et al. | 514/382 |

FOREIGN PATENT DOCUMENTS

| | | | |
|---|---|---|---|
| 0 653160 | 1/1992 | Australia | 548/112 |
| 2 000 774 | 1/1979 | United Kingdom | 548/323.5 |
| 9204331 | 3/1992 | WIPO . | |

OTHER PUBLICATIONS

CA 116(25):255613, 19 Mar. 1992, Hickey et al.
CA 82(25):170937W, 1975, Jorgensen.
CA 117(3):26565, 19 Mar. 1992, Hickey et al.
CA 117(11):111 616JA, 19 Mar. 1992, Hickey et al.
CA 115(5):49682, 1991, Meanwell et al.
CA 112(6):42581b, 1989, Duerr.
CA 110(16):141549h, 1986, Schmitz et al.
CA 105(23):20887p, 1986, Lautenschlaeger et al.
Medline 92170539, 1991, Winkler et al.
Medline 911521139, 1991, Winkler et al.
CA 116(13):125547d, 1991, Suguira et al.
CA 115(17):177545a, 1991, Uemura et al.
Ninio et al., Regulation of the COA–Independent Transacylase in Human Neutrophils, Federation of European Biochemical Societies, Jul. 1991, pp. 138–140.

*Primary Examiner*—Brain M. Burn
*Attorney, Agent, or Firm*—Dara L. Dinner; Stephen Venetianer; Edward T. Lentz

[57] ABSTRACT

Coenzyme A-independent transacylase is required for the release of free arachidonic acid, and the production of arachidonic acid metabolites and platelet activation factor. Blocking of this enzyme inhibits the production of these inflammatory mediators and will be of therapeutic utility in a broad range of allergic and inflammatory diseases and disorders. Compounds are described herein which inhibit the action of CoA-IT and are therefore useful in the treatment of disease states caused thereby.

30 Claims, 12 Drawing Sheets

Role of CoA-Independent transacylase in Arachidonic acid and Platelet-Activating Factor Metabolism

COA-IT AND PAF INHIBITORS

This application is a continuation-in-part application of PCT application US93/01247, filed 11 Feb. 1993, which is a continuation-in-part application of U.S. Ser. Nos. 07/833,850 (now abandoned); 07/833,877 (now abandoned); 07/833,878 (now abandoned); 07/833,879 (now abandoned); 07/833,880 (now abandoned); 07/834,048 (now abandoned), all filed 11 Feb. 1992.

FIELD OF THE INVENTION

The invention relates to the area of inflammatory mediators. The invention is based on the discovery that blocking a key enzyme responsible for arachidonate movement (or remodelling), Coenzyme A-independent transacylase (CoA-IT), inhibits the production of lipid mediators (free arachidonic acid, arachidonic acid metabolites, and platelet-activating factor (PAF)). It has been discovered that CoA-IT is required to maintain arachidonate content in cellular phospholipids, for the release of free arachidonic acid and the synthesis of arachidonic acid metabolites and PAF. As CoA-IT is involved in arachidonate phospholipid metabolism, and required for the release of free arachidonaic acid and the production of eicosanoids and PAF, inhibition of such would be useful for the treatment of disease states caused thereby.

BACKGROUND OF THE INVENTION

An early event in the response of most inflammatory cells to immunologic activation and other stimuli is the release of newly formed products (mediators) which alter the function and biochemistry of surrounding cells and tissues. The ensuing biological responses, as well as much of the pathogenesis which is attributed to inflammation and allergy, are thought to be dependent on the effects that these newly-formed mediators have on adjacent cells within the inflammatory region.

In the last 20 years, it has become apparent that lipid mediators are among the most potent and important products which are generated during inflammatory reactions. The synthesis of most lipid mediators is initiated by the cleavage of complex phospholipid molecules which contain arachidonate at their sn-2 position. Free arachidonic acid is released from these phospholipids and this represents the rate-limiting step in the formation of eicosanoids (leukotrienes, prostaglandins and thromboxanes). As arachidonic acid is released, it is then converted to oxygenated derivatives by at least two enzymatic systems (lipoxygenase and/or cyclooxygenase). Concomitant with arachidonate release, lysophospholipids are formed. One of these lyso phospholipids, 1-alkyl-2-lyso-sn-glycero-3-phosphocholine, is then acetylated to form platelet-activating factor (PAF). Each of the cell types involved in the inflammatory response produce and secrete a unique subset of lipid mediators. The quantities and nature of the metabolites depend on which enzymes and precursor phospholipid pools are available to inflammatory cells.

Once lipid mediators such as PAF and eicosanoids are formed by the aforementioned pathways, they induce signs and symptoms observed in the pathogenesis of various inflammatory disorders. Indeed, the pathophysiological activity of arachidonic acid (and its metabolites) is well known to those skilled in the art. For example, these mediators have been implicated as having an important role in allergy, asthma, anaphylaxis, adult respiratory distress syndrome, reperfusion injury, inflammatory bowel disease, rheumatoid arthritis, endotoxic shock, and cardiovascular disease. Aalmon and Higgs [Br. Med. Bull (1978) 43:285–296]; Piper et al. [Ann. NY Acad. Sci. (1991) 629:112–119]; Holtzman [Am. Rev. Respir. Dis. (1991) 143:188–203]. Snyder (Am. J. Physiol. Cell Physiol.) (1990) 259:C697–C708]; Prescott et al. [J. Biol. Chem. (1990) 265:17381–17384].

Similar to arachidonate products, PAF is a potent proinflammatory mediator produced by a variety of cells. In vitro, PAF stimulates the movement and aggregation of neutrophils and the release therefrom of tissue-damaging enzymes and oxygen radicals. PAF has also been implicated in activation of leukocytes, monocytes, and macrophages. These activities contribute to the actions of PAF as having (pathological) physiological activity in inflammatory and allergic responses. PAF has also been implicated in smooth muscle contraction, pain, edema, hypotensive action, increases in vascular permeability, cardiovascular disorders, asthma, lung edema, endotoxin shock, and adult respiratory distress syndrome. PAF elicits these responses either directly through its own cellular receptor(s) or indirectly by inducing the synthesis of other mediators.

Accordingly, a method which antagonises the production of free arachidonic acid, its metabolites or PAF will have clinical utility in the treatment of a variety of allergic, inflammatory and hypersecretory conditions such as asthma, arthritis, rhinitis, bronchitis and urticaria, as well as reperfusion injury and other disease involving lipid mediators of inflammation.

Many published patent applications or issued U.S. patents exist which describe various compounds having utility as PAF or Eicosanoid antagonists. Such patents include U.S. Pat. Nos. 4,788,205, 4,801,598, 4,981,860, 4,992,455, 4,983,592, 5,011,847, 5,019,581 and 5,002,941.

Described in this application is a method to inhibit the generation of lipid mediators. As mentioned above, arachidonate-containing phospholipids are the key precursors for a broad range of lipid mediators including arachidonic acid, eicosanoids and PAF. Because of the special role arachidonate-containing phospholipids have in mediator generation, inflammatory cells treat these phospholipids differently than other fatty acid-containing phospholipids. In particular, there are enzymes which control the amount of arachidonate in different phospholipid pools and these enzymes are tightly regulated to maintain arachidonate homeostasis. The movement of arachidonate into and from all phospholipids was originally thought to be exclusively by CoA-dependent acyl transferase activities. Holub et al., *Adv. Lipid Res.*, 16:1–125 (1978); Lands et al., In The Enzymes of Biological Membranes, ed. Martonosi, A., pp. 3–85, Plenum Press, NY, 1976. However, it has now been demonstrated that an enzyme, CoA-IT, is involved in the movment of arachidonate into particular (1-alkyl- and 1-alkenyl) phospholipid pools. These are the phospholipid pools of arachidonate that are preferentially mobilized during cell activation. Moreover, arachidonic acid and lyso-PAF released from these pools are utilized for eicosanoid and PAF, respectively.

CoA-IT has a specificity for certain phospholipids as donor and acceptor molecules. The fatty acid transferred is long chained and unsaturated, and almost exclusively arachidonate. Other fatty acids such as the 16:0, 18:1 or 18:2 are not apparently moved into alkyl and 1-alkenyl phospholipid pools by CoA-IT. The specificity of CoA-IT is in direct contrast to many other CoA-dependent acylation activities which acylate a wide variety of lysophospholipids with no selectivity for arachidonate.

Accordingly, a method by which CoA-IT is inhibited will consequently and preferentially decrease the arachidonate content of 1-alkyl- and 1-alkenyl-linked phospholipids and will therefore decrease the production of pro-inflammatory mediators such as free arachidonic acid, leukotriene and PAF during an inflammatory response. Accordingly, a method by which CoA-IT is inhibited, will have clinical utility in the treatment of allergic, inflammatory and hypersecretory conditions.

SUMMARY OF THE INVENTION

It is an object of this invention to provide a method of treating or reducing allergy and inflammation. It is also an object of this invention to inhibit undesirable lipid mediator production.

This invention is based on the discovery that blocking CoA- independent transacylase, using selective pharmacologic tools, prevents the movement of arachidonate into phospholipid pools needed for the concomitant formation of PAF, free arachidonic acid and its metabolites such as eicosanoids.

The invention relates to a method of treating disease or disorders mediated by free arachidonic acid, its metabolites and/or PAF by administering to a patient in need thereof, an effective amount of a compound which inhibits the production, activation or action of CoA-IT. Inhibition of CoA-IT inhibits lipid mediator production as well as signs and symptoms of disease and disorders induced by lipid mediators.

The premise of this invention is that blocking the movement of arachidonate into specific arachidonate-containing phospholipid pools inhibits lipid mediator (PAF and eicosanoid) production by inflammatory cells. More precisely, when arachidonate is prevented from entering key common precursor phospholipids, precursor molecules will not be formed. If key precursor pools are not formed, arachidonate cannot be removed from these precursors. This means that free arachidonic acid and lyso PAF will be not be mobilized and therefore PAF as well as eicosanoids will not be produced. The end result of CoA-IT inhibition will be reduced signs and symptoms of allergy and inflammation mediated by eicosanoids and PAF.

Still another aspect of the invention relates to a method of screening chemical compounds for potential anti-inflammatory action. In this way, chemical compounds can be rapidly and easily screened for the ability to inhibit CoA-IT and be useful as an anti-inflammatory agent.

Another aspect of the invention relates to the therapeutic use, in medicine,of the compounds, and pharmaceutical compositions, as disclosed herein, in particular for compounds of Formulas (I) to (VI), as inhibitors of CoA-IT activity. As CoA-IT activity is required for the release of lipid inflammatory mediators, such as arachidonic acid and the production of platelet-activiating factor, by inflammatory cells and that inhibition of the production, activation or activity of CoA-IT will have beneficial and therapeutic effect the compounds of the present invention, as described herein, which are inhibitors of CoA-IT are useful in the treatment of disease states caused thereby.

Treatment of disease states caused by these lipid inflammatory mediators i.e., arachidonate, eicosanoids and PAF, include certain cardiovascular disorders such as but not limited to, myocardial infarction, stroke, circulatory shock, or hypotension, ischemia, reperfusion injury, inflammatory diseases such as, but not limited to, arthritis, inflammatory bowel disease, Crohn's disease, or ulcerative colitis, respiratory disease such as but not limited to, asthma, or adult respiratory distress syndrome, analphylaxis, shock such as but not limited to endotoxic shock, topical disesases, such as but not limited to actinic keratosis, psoriasis, or contact dermatitis, or pyresis.

BRIEF DESCRIPTION OF THE DRAWINGS

The accompanying drawings contain the following figures.

DETAILED DESCRIPTION OF THE INVENTION

It has now been discovered that CoA-IT activity is required for lipid mediator production. Specifically, it has been discovered that CoA-IT activity is required for the movement of arachidonate into, and the maintance of arachidonate within, phospholipid pools from which it can be released to form free arachidonic acid and for the production of lyso PAF needed for PAF synthesis. Further, CoA-IT has been shown to be crucial in the mobilization of lyso-PAF and free arachidonic acid during inflammatory cell activation. Inhibition of CoA-IT activity will result in a decrease in arachidonate content of phospholipids, a decreased production of PAF, and a decreased release of free arachidonic acid from cellular phospholipids.

Figure 1:
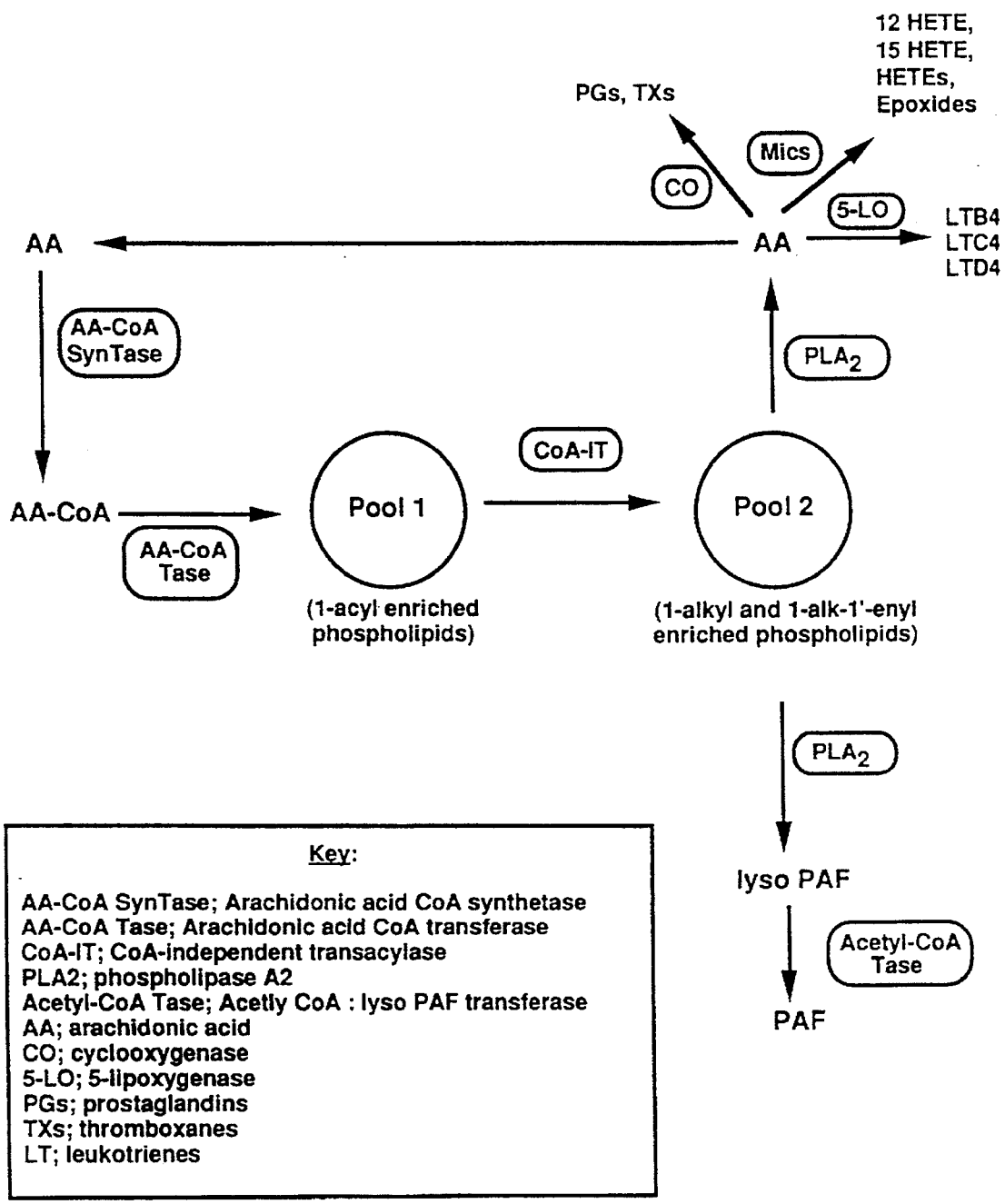
FIG. 1 illustrates the Role of CoA-Independent Transacylase in Arachidonic Acid and Platelet-Activating Factor Metabolism.

More specficially, FIG. 1 shows a simplified scheme of how arachidonic acid is directed through phospholipids of inflammatory cells. As arachidonic acid enters inflammatory cells or is produced within these cells, it is converted to arachidonoyl-CoA by the enzyme arachidonoyl CoA synthetase. At that point, arachidonic acid is incorporated into the sn-2 position of a lyso phospholipid by arachidonoyl-CoA acyl transferase. The arachidonate-containing phospholipids formed in this reaction appear to belong to a special group or pool (pool 1) of phospholipids which contains predominantly 1-acyl-linkages at the sn-1 position of the molecule. When cells are not stimulated, arachidonic acid is slowly transferred from this first pool to other pools (pool 2) of phospholipids which contain predominantly 1-alkyl and 1-alk-1-enyl linkages at the sn-1 position and phosphatidylcholine and phosphatidylethanolamine linkages at the sn-3 position of phospholipids. This transfer into other pools of AA-containing phospholipids is accomplished by the enzyme CoA-IT.

During inflammatory cell stimulation, there is a calcium-dependent activation of an enzyme phospholipase $A_2$ which removes arachidonic acid from arachidonate-containing phospholipids which are predominantly in the second (1-alkyl and 1-alk-1-enyl) pool (pool 2). Arachidonic acid and lyso phospholipids formed in this reaction become key intermediates for eicosanoid generation and platelet activating factor generation, respectively. In particular, one of these arachidonate-containing phospholipids in pool 2, 1-alkyl-2-arachidonyl-sn-glycero-3-phosphocholine, is a common precursor for arachidonate and platelet-activating factor. During inflammatory cell activation, arachidonic acid is rapidly depleted from phospholipids in pool 2. As these pools are depleted by the action of phospholipase $A_2$, they are rapidly replenished by CoA-IT. It is our discovery that the movement of arachidonate into special pools mediated by CoA-IT is required for lipid mediator production and that the blockage of CoA-IT will decrease arachidonate content within cellular phospholipids and inhibit lipid mediator production. This will have beneficial therapeutic effects for diseases mediated, in some part, by eicosanoids and platelet-activating factor.

1. Characteristics of CoA-IT Activity

CoA-IT activity had been defined to have the following characteristics.

A. Co-factors

CoA-IT activity is independent of the presence of Coenzyme A. In addition, no other co-factors required for activity or that modulate activity have been discovered. CoA-IT activity is not altered by the absence or presence of calcium (0–10 mM), magnesium (0–10 mM), EGTA (0–2 mM), EDTA (0–10 mM), ATP, CoA or CoA-fatty acids.

B. pH

CoA-IT activity over a wide range of pH levels was determined. The results demonstrate that the enzyme is active over a broad pH range of 6.5–9. The activity of the enzyme rapidly decreases below pH 6.5 and above pH 10.

C. Kinetics.

The kinetics of the CoA-IT reaction were studied with various concentrations of 1-alkyl-2-lyso-GPC. CoA-IT activity increases as a function of the concentration of substrate, 1-alkyl-2-lyso-GPC. The enzyme exhibits an apparent substrate affinity ($K_m$) for 1-alkyl-2-lyso-GPC of 0.1–2 μM.

D. Other Characteristics

CoA-IT is stable when treated with dithiothreitol (DTT) or 2-mercaptoethanol (1–10 mM). CoA-IT is inactivated by exposure to heat or acid and is inhibited by addition of detergents such as 3-octyl glucoside, deoxycholate, cholate, Triton X-100, C12E8, CHAPS and hexadecyl-trimethyl ammonium bromide.

E. Specificity

A key characteristic of CoA-IT is the exquisite specificity of this enzyme for polyunsaturated fatty acids and especially arachidonic acid. Sugiura et al. (J. Biol. Chem. (1987) 262:1199–1205); Chilton et al. (J Biol. Chem. (1983) 258:7268–7271); Kramer and Deykin (J. Biol. Chem. (183) 258:13806–13811).

F. Location

Within the cell, CoA-IT activity is completely and tightly associated with microsomal membranes. Treatment of these membranes with 2M KCl fails to extract more than 75% of the CoA-IT activity, suggesting that CoA-IT is an integral membrane component. The subcellular location of CoA-IT activity remains to be determined.

Evidence of CoA-IT activity exists in a variety of inflammatory cells, including human neutrophils, monocytes, lung mast cells, guinea pig eosinophils and human U937 monocytic and HL-60 granulocyte cells lines. There is also preliminary evidence that somewhat less CoA-IT activity is found in tissues such as lung, liver and kidney. Less activity yet is found in heart, skeletal muscle and brain.

G. Comparison with other enzymes

CoA-IT has characteristics which distinguish its activity from the activities of other enzymes involved in lipid metabolism, such as phospholipase $A_2$, lypoxygenases, cyclooxygenases, CoA-dependent acyltransferases and PAF acetyl transferase.

These differences include different co-factor requirements, location within cells, effects of detergents on activity, effects of heat or acid treatment, stability to reducing agents such as dithiothreitol (DTT) and selectivity for arachidonate-containing substrates. The following Table, Table I, summarizes these differences in characteristics between CoA-IT and other enzymes.

TABLE I

Comparison of CoA-IT to other enzymes

| Property | CoA-IT | Pan.PLA$_2$ | LMW PLA$_2$ | HMW PLA$_2$ |
|---|---|---|---|---|
| Co-factors | None | Ca$^{2+}$ | Ca$^{2+}$ | Ca$^{2+}$ |
| Location | membrane | extracellular | extracellular | cytosol |
| Detergent | inhibition | stimulation | inhibition | stimulation |
| Heat/Acid | unstable | stable | stable | unstable |
| DTT | no effect | inhibition | inhibition | no effect |
| AA sel | yes | no | no | yes |

| Property | CoA-IT | CoA-D | AcetylTase | AcetylHy |
|---|---|---|---|---|
| Co-factors | None | CoA | Ca$^{2+}$/A-CoA | none |
| Location | membrane | membrane | membrane | cyto/LDL |
| Detergent | inhibition | mixed | no effect | mixed |
| Heat/Acid | unstable | — | — | stable |
| DTT | no effect | no effect | no effect | inhibition |
| AA Sel | yes | no | no | no |

| Property | CoA-IT | CO | 5LO | |
|---|---|---|---|---|
| Co-factors | None | peroxide | peroxide | |
| Location | membrane | membrane | cyto-memb | |
| Detergent | inhibition | no effect | — | |
| Heat/Acid | unstable | unstable | unstable | |
| DTT | no effect | — | no effect | |
| AA Sel | yes | yes | yes | |

Key to Table 1:
Pan. Pancreatic
LDL low density lipoprotein
CoA-D CoA-dependant acyltransferase
AcetylTase Acetyl-CoA transferase
—no data available
LMW low molecular weight
HMW high molecular weight
cyto cytosol
Ca$^{2+}$calcium
CO cyclooxygenase
5LO 5-lipoxygenase
DTT dithiotheritol
A-CoA Acetic-CoA
AA Sel Arachidonic acid selectivity This distinction of CoA-IT from the other enzymes based on characteristics is important for several reasons. First, the data indicate that CoA-IT activity is a novel enzyme activity. Second, even though a microsomal preparation is used to assess CoA-IT activity, the distinct characteristics of CoA-IT assure that the assays measure only CoA-IT activity. Finally, the characteristics of CoA-IT demonstrate that the pharmacological utility of inhibition of CoA-IT is unique.

2. CoA-IT inhibition (a) Evaluation of CoA-IT inhibition in broken cell assays

Figure 2:
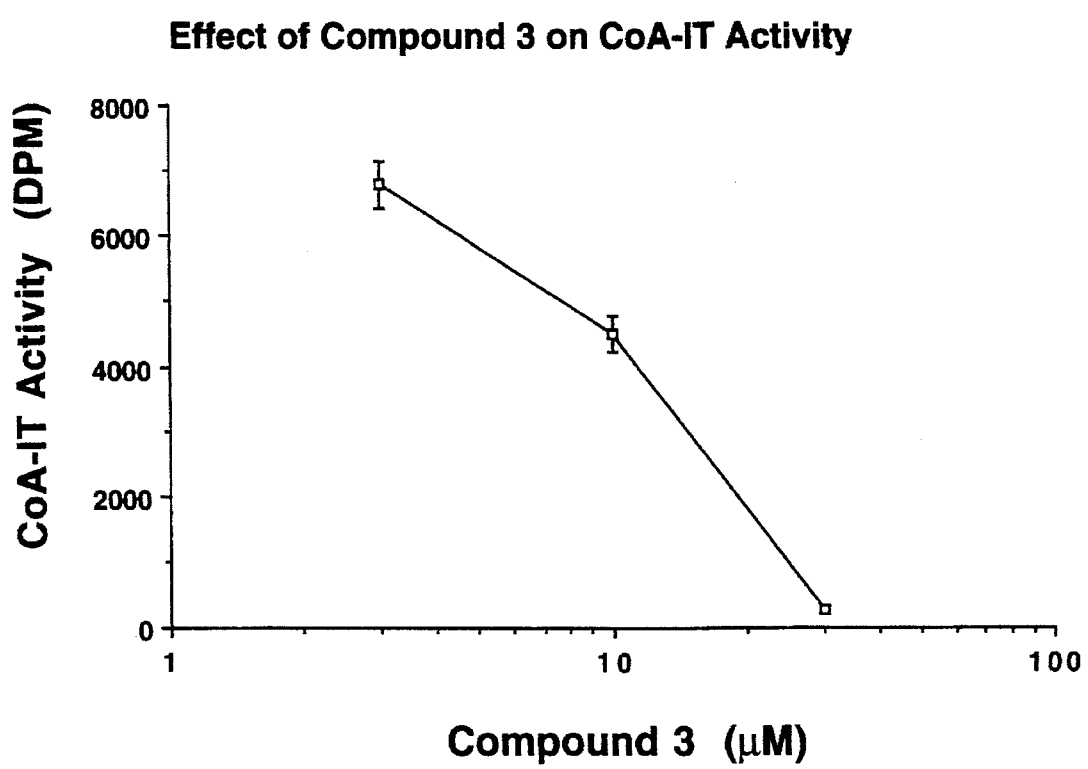
FIG. 2 illustrates the effects of the compound of Example 3, Diethyl 7-(3,4,5-triphenyl-2-oxo-2,3-dihydro-imidazol-1-yl)heptane-phosphonate on CoA-IT activity.

Inhibitors of CoA-IT activity have now been discovered and characterized. Suitable inhibitors can readily be identified employing the broken cell assay (a) described below. For example, FIG. 2 shows the effect of compound 3 on CoA-IT activity. Often, inhibitors will include an imidazole structure.

(b) Evaluation of CoA-IT inhibitors in intact cells

Figure 3:
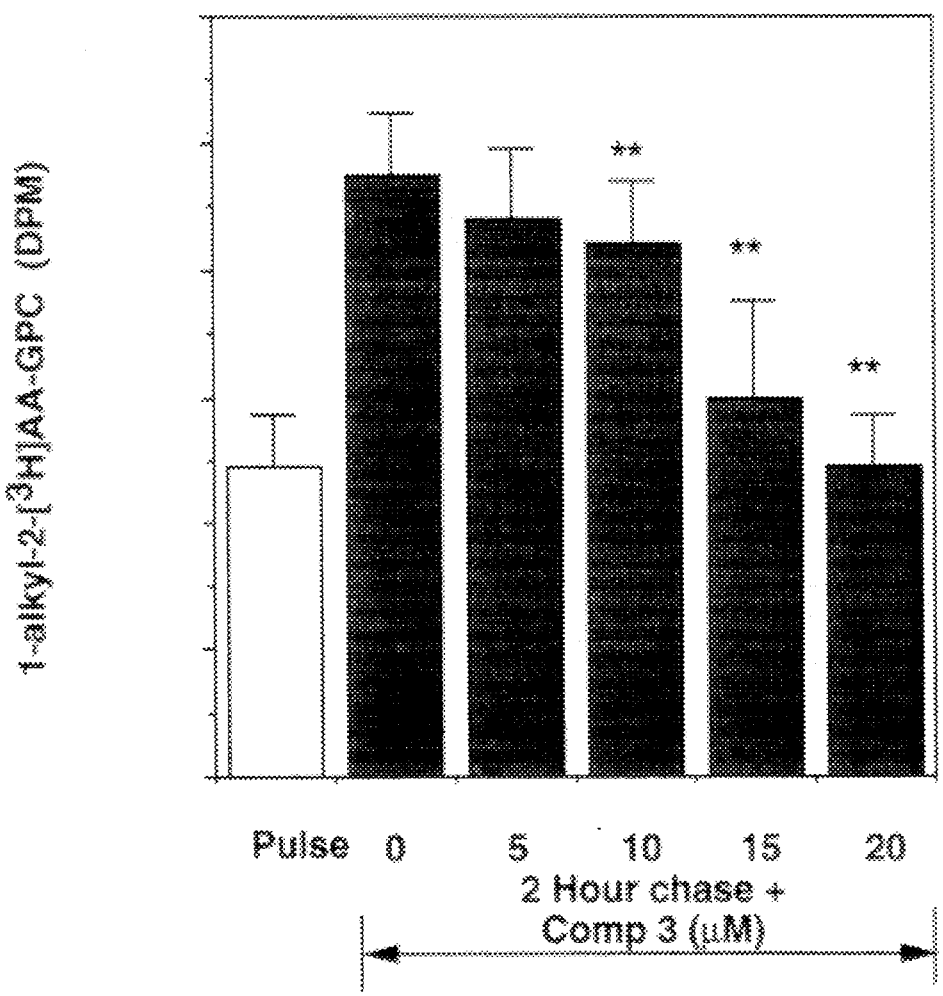
FIG. 3 illustrates the effects of the compound of Example 3, Diethyl 7-(3,4,5-triphenyl-2-oxo-2,3-dihydro-imidazol-1-yl)heptane-phosphonate which produce a concentration-dependent blockade in the movement of [$^3$H]arachidonate into 1-ether-linked phospholipids, 1-alkyl PC and 1-alkenyl PE.
Figure 3A:
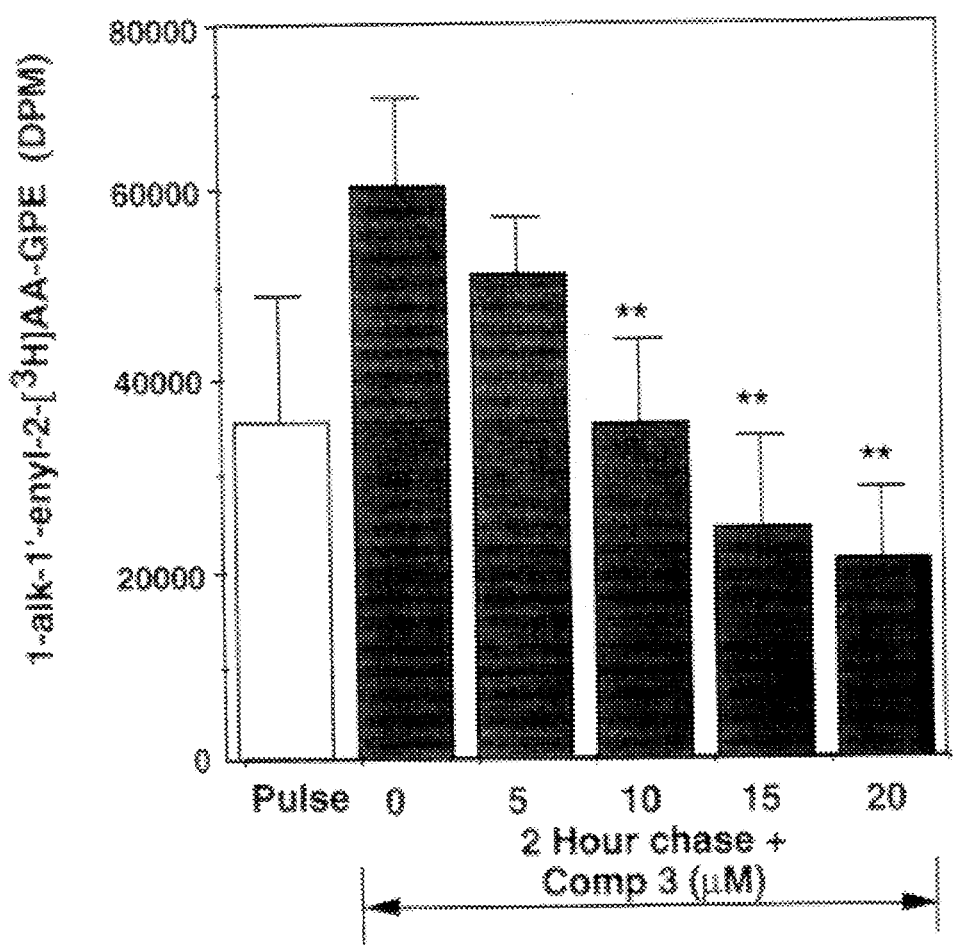
Figure 4A:
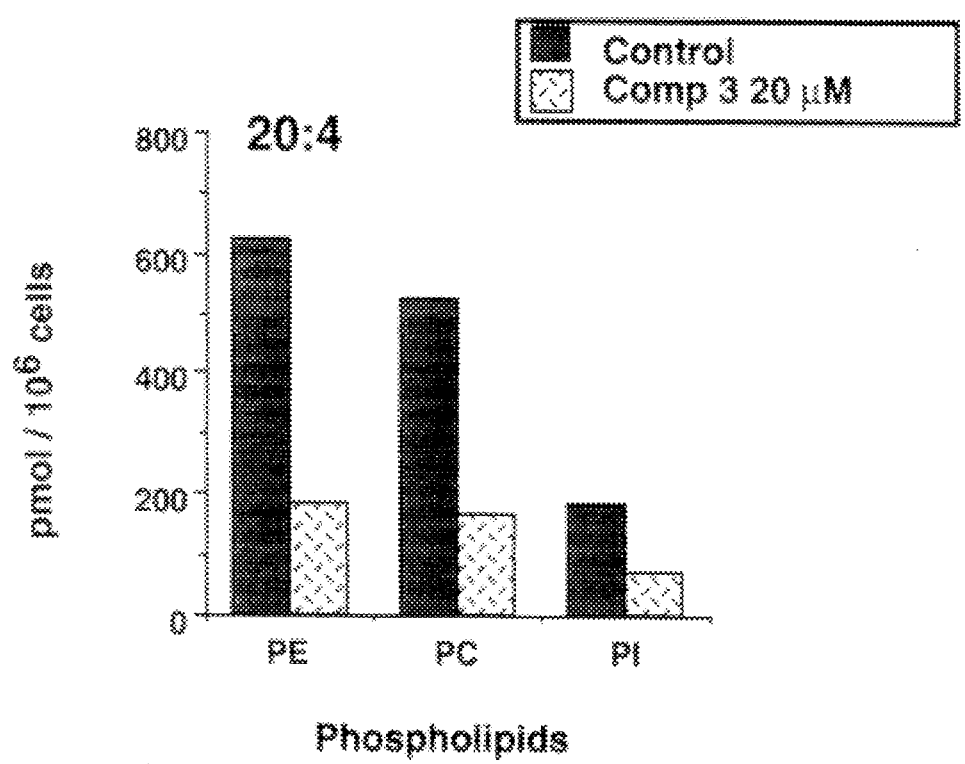
FIG. 4 illustrates the effects of the compound of Example 3, Diethyl 7-(3,4,5-triphenyl-2-oxo-2,3-dihydro-imidazol-1-yl)heptane-phosphonate which induced a concentration-dependent loss of arachidonate from all major phospholipid classes of the mast cell. In contrast, there was no loss in the mass of 18:0, 18:1, 18:2 from PI, PE and PC in response to Compound 3.
Figure 4B:
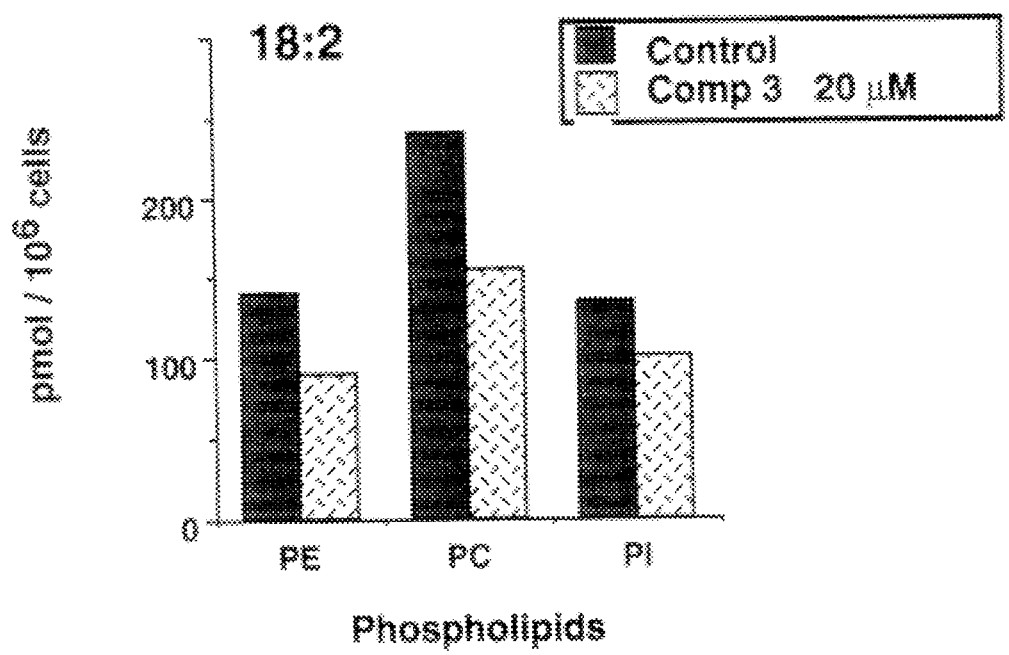
Figure 4C:
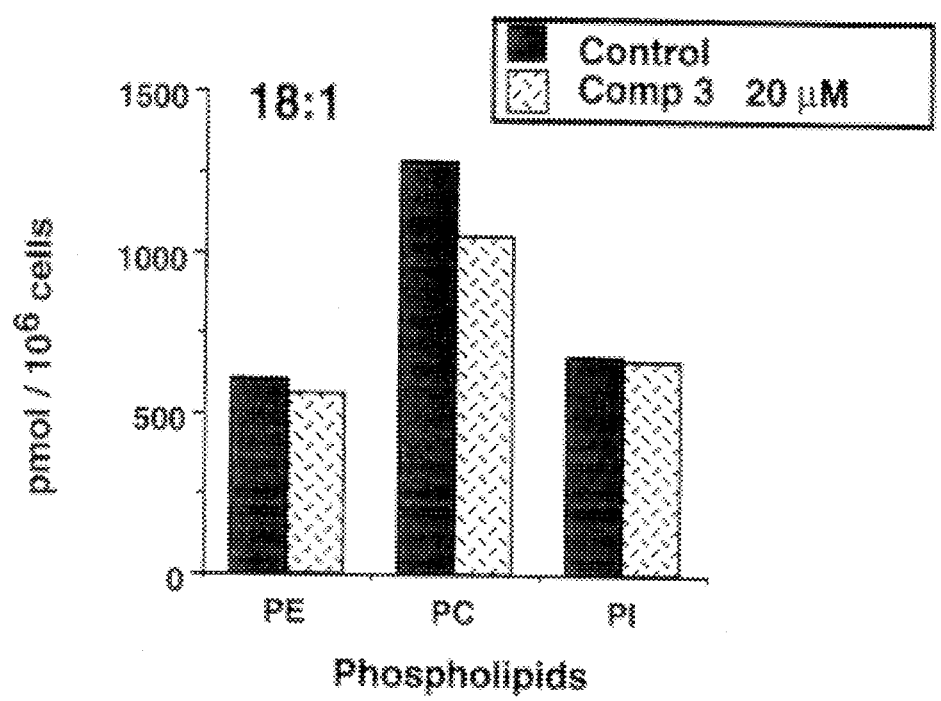
Figure 4D:
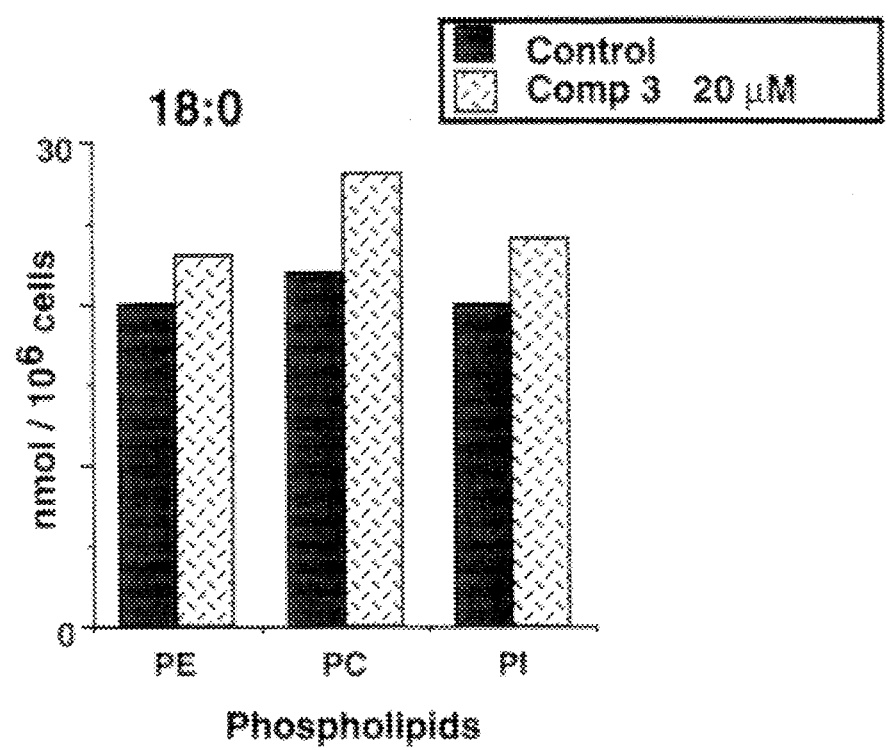

CoA-IT activity can also be measured in intact cells by following the movement of a pulse of [$^3$H]arachidonate as it moves into the "pool 2" phospholipids (1-alkyl and 1-alkenyl phospholipids) in inflammatory cells. These specific studies were performed in intact human neutrophils, which contain CoA-IT activity and transfer arachidonate into 1-alkyl and 1-alkenyl phospholipids. To determine the effects of Compound 3 on this transfer of arachidonate, neutrophils were exposed briefly to [$^3$H]arachidonic acid to allow incorporation of the label into 1-acyl phospholipids, treated with various concentrations of Compound 3 and the movement of [$^3$H]arachidonate between phospholipid subclasses assessed over the subsequent 2 hours in the absence of cellular stimulation. FIG. 3 shows that Compound 3 produced a concentration-dependent blockade in the movement of [$^3$H]arachidonate into 1-ether-linked phospholipids, 1-alkyl PC and 1-alkenyl PE, and at concentrations similar to those needed to block CoA-IT activity in a broken cell preparation. It is important to note that Compound 3 could completely block arachidonate movement, suggesting that not only can CoA-IT mediate this movement, but that CoA-IT activity is required for arachidonate transfer and that no other enzyme can substitute for CoA-IT.

As treatment of intact cells blocks the movement of arachidonate into specific cellular phospholipids, it followed that prolonged treatment of inflammatory cells with CoA-IT inhibitors could deplete their large endogenous pools of arachidonate within phospholipids. To determine that CoA-IT inhibition can alter the amount of arachidonate within cellular phospholipids, mouse bone marrow-derived mast cells were treated with Compound 3 for 24 hours and the mass of arachidonate within total cellular phospholipids was determined. Compound 3 induced a concentration-dependent reduction in the total cellular arachidonate within mast cells, with greater than 75% reduction apparent at 20 µM. As CoA-IT is specific for arachidonate and not other fatty acyl groups, it is critical to compare the effect CoA-IT inhibitors have on arachidonate with other polyunsaturated fatty acids. FIG. 4 illustrates that Compound 3 induced a concentration-dependent loss of arachidonate from all major phospholipid classes of the mast cell. In contrast, there was no loss in the mass of 18:0, 18:1, 18:2 from PI, PE and PC in response to Compound 3. These results show that CoA-IT inhibitors selectively deplete arachidonate, but not other polyunsaturated fatty acids, from inflammatory cells. The magnitude and rapidness of the loss of arachidonate is striking, and suggests a novel mechanism of action and unique therapeutic potential for CoA-IT inhibitors.

3. Role of CoA-IT in PAF Production and AA Release

The molecule 1-alkyl-2-arachidonoyl-GPC has been shown to be a necessary precursor for PAF production (Chilton et al., *J. Biol. Chem.* (1984) 259, 12014–12020). CoA-IT activity plays two pivotal roles in PAF production, centering on this molecule. First, CoA-IT activity is required for the specific movement of arachidonate into 1-alkyl-2-arachidonoyl-GPC to produce the necessary precursor molecule for PAF. Second, CoA-IT activity has been shown to promote the breakdown of the precursor of PAF, 1-alkyl-2-arachidonoyl-GPC into lyso PAF, to allow PAF production. This CoA-IT mediated production to lyso PAF can be differentiated from $PLA_2$ activity. CoA-IT activity plays a central and necessary role in the production of PAF.

There is strong evidence that, in activated inflammatory cells, arachidonate is released from specific phospholipid pools. For example, in neutrophils and mast cells the primary source of free arachidonic acid is 1-alkenyl-2-arachidonoyl-GPE. As shown in FIG. 1, CoA-IT activity, due to its unique properties, can replenish this pool with arachidonate to allow and maintain the release of free arachidonic acid. It has now been discovered that CoA-IT activity is necessary and essential for the release of free arachidonic acid and the subsequent formation of bioactive lipid mediators.

Figure 5:
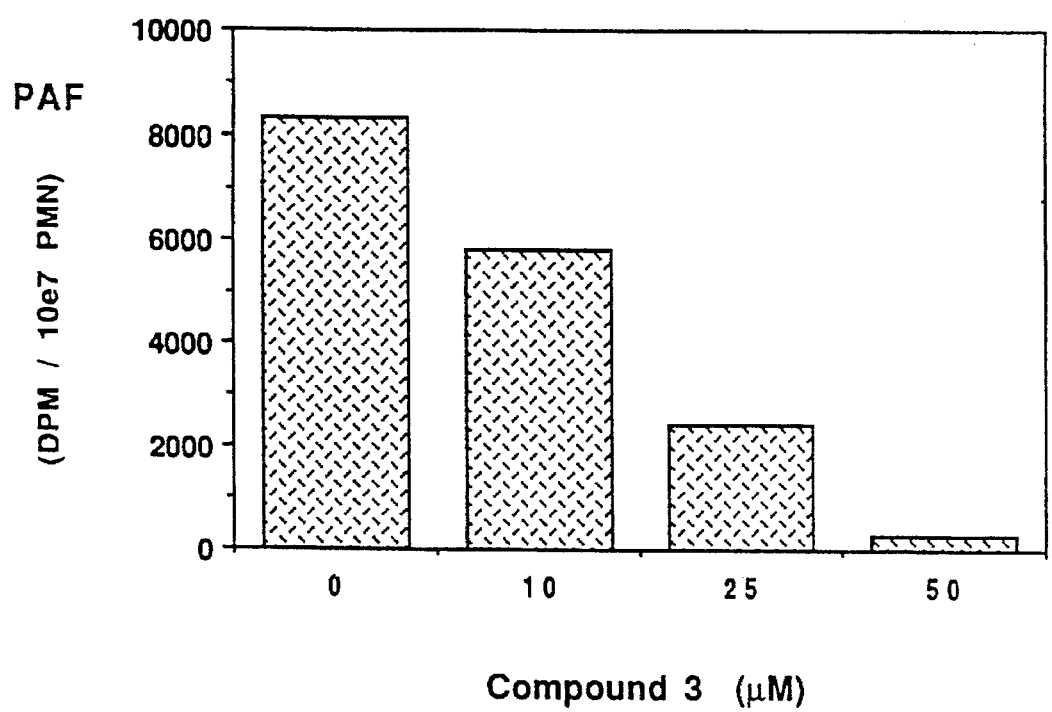
FIG. 5 illustrates the effects of the compound of Example 3, Diethyl 7-(3,4,5-triphenyl-2-oxo-2,3-dihydro-imidazol-1-yl)heptane-phosphonate on inhibition of the production of PAF in human neutrophils.
Figure 6:
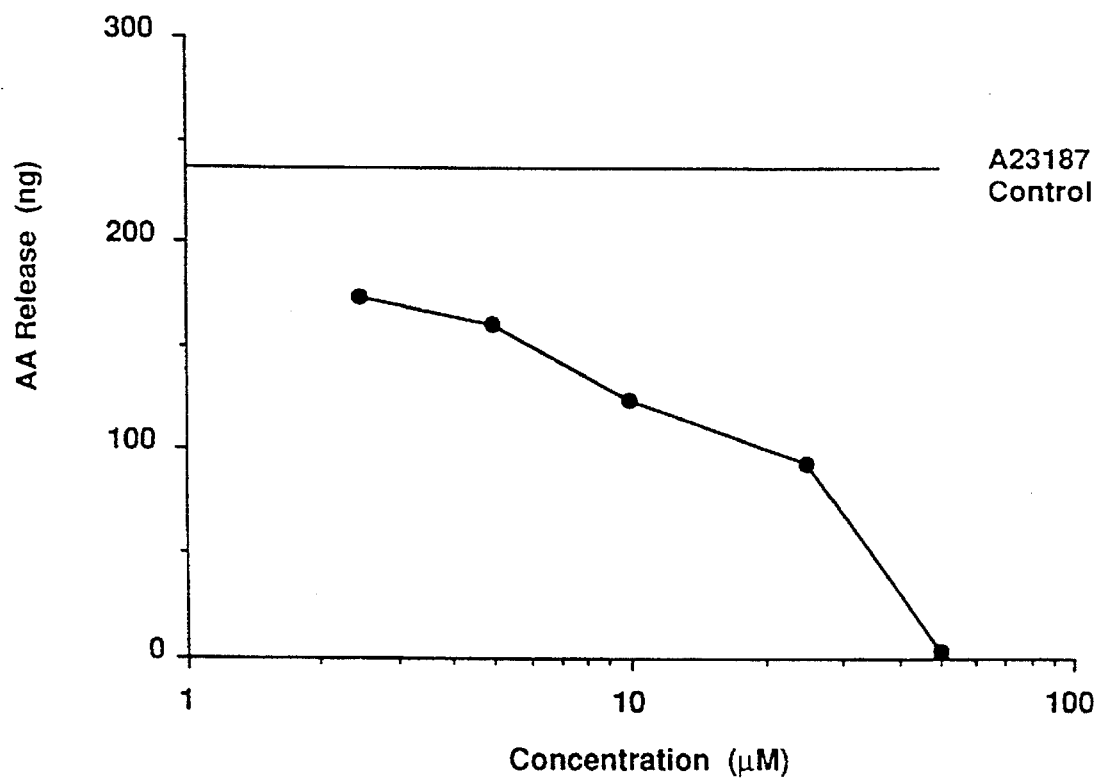
FIG. 6 illustrates the effects of the compound of Example 3, Diethyl 7-(3,4,5-triphenyl-2-oxo-2,3-dihydro-imidazol-1-yl)heptane-phosphonate on inhibition of free arachidonic acid release in a concentration dependent fashion.

To further demonstrate the utility of inhibiting CoA-IT, the compound of Example 3 was shown to inhibit the production of PAF (assay c) and the release of free arachidonic acid (assay b) from human neutrophils. The method of synthesis of this compound and its structural formula is set forth below. This compound inhibited PAF production (FIG. 5) and free arachidonic acid release (FIG. 6) completely and in a concentration dependent fashion. The specificity for inhibition of CoA-IT activity for these compounds and not the activity of other enzymes, such as PLA2 and PAF acetyl transferase, has been demonstrated. These data demonstrate that inhibition of CoA-IT can and will inhibit the production of PAF and the release of free arachidonic acid.

4. Role of CoA-IT in Inflammatory Responses in vivo

Figure 7A:
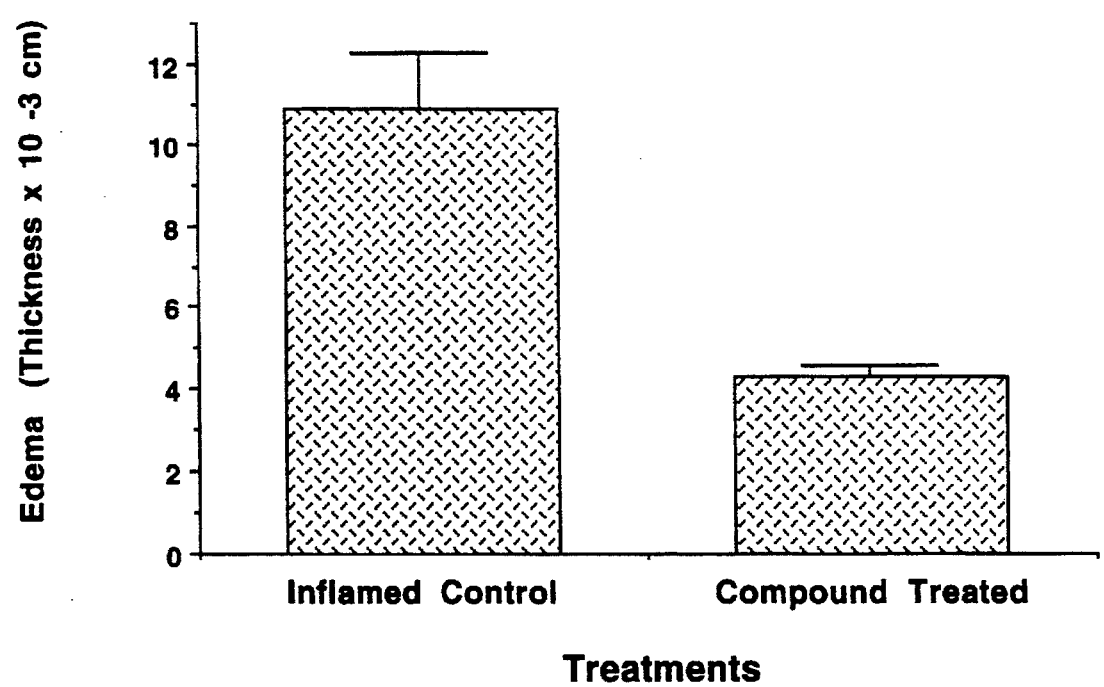
FIG. 7 illustrates the in vivo anti-inflammatory responses of the compound of Example 3, Diethyl 7-(3,4,5-triphenyl-2-oxo-2,3-dihydro-imidazol-1-yl)heptane-phosphonate in the mouse ear by the topical application of a pro-inflammatory agent, 12-0-tetradecanoylphorbol 13-acetate.
Figure 7B:
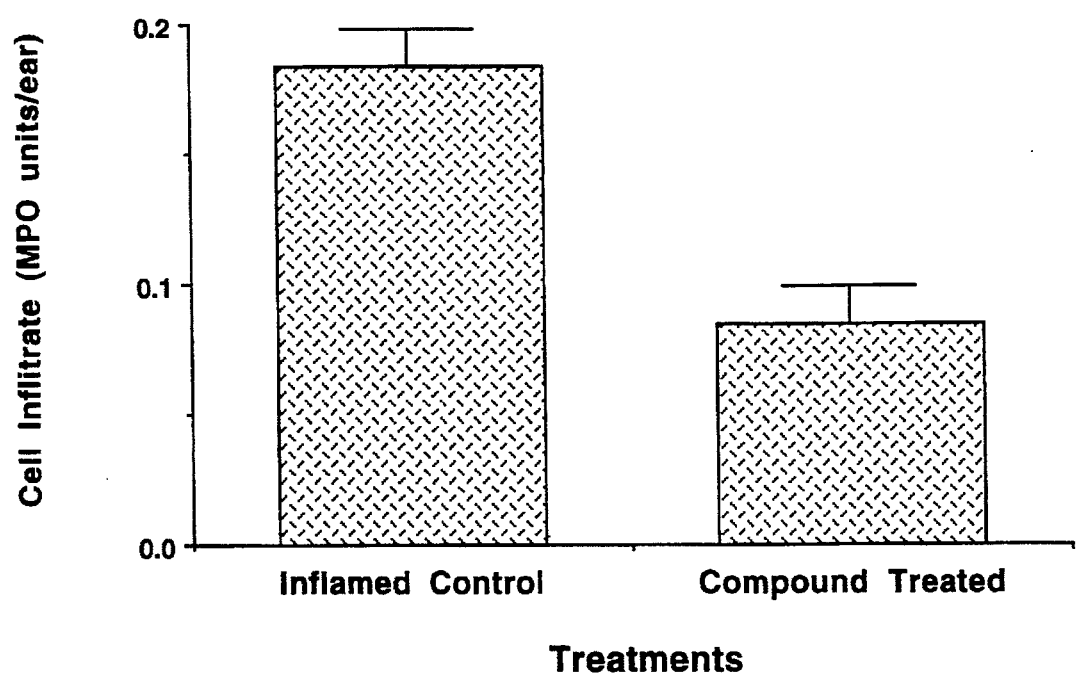

The ability of compounds that inhibit CoA-IT to affect in vivo inflammatory responses was assessed. Inflammatory responses were induced in the mouse ear by the topical application of a pro-inflammatory agent, such as 12-0-tetradecanoylphorbol 13-acetate. This produced an edematous response, as measured by increases in ear thickness, as well as increased inflammatory cellular infiltrate, as measured by increases in myeloperoxidase activity as described in the methods. Application of compounds that inhibit CoA-IT had an anti-inflammatory effect, as demonstrated for compound 3 in FIG. 7. This proven anti-inflammatory effect is predictive of therapeutic usefulness in a wide variety of inflammatory diseases and conditions.

5. Assays (a) Assay for CoA-IT Activity

The following is a method to measure CoA-IT activity and the effects of compounds on CoA-IT activity. The assay is based upon mixing cellular material containing CoA-IT activity with a stable lyso phospholipid such as 1-alkyl-2-acyl-GPC and measuring the production of phospholipid product such as 1-alkyl-2-acyl-GPC occurring in the absence of added CoA or CoA-fatty acids.

Cell Preparation

Any inflammatory cell that contains high levels of CoA-IT activity can be used, such as neutrophils, macrophages or cell lines such as U937 cells. U937 cells were obtained from American Type Culture Collection and grown in RPMI-1640 media (Gibco, Grand Island, N.Y.) supplemented with 10% fetal bovine serum (Hyclone, Logan, Utah) at 37° C., 5% $CO_2$. Cells were grown without differentiation (basal state) by any agent, such as dimethyl sulfoxide. As used herein, "inflammatory cells" include, but are not limited to neutrophils, macrophages, monocytes, lymphocytes, eosinophils, basophils, and mast cells.

Microsomal preparation

Microsomes were prepared using standard techniques. In this case, cells were washed with a buffer of 250 mM sucrose, 10 mM Tris, 1 mM EGTA, 1 mM $MgCl_2$, pH 7.4 and ruptured by $N_2$ cavitation (750 psi, 10 minutes). The ruptured cells were centrifuged 1000× g, 5 minutes. The resulting supernatant was centrifuged at 20,000×g,~20 minutes. Microsomes were prepared from this supernatant by centrifugation at 100,000× g, 60 minutes. The resulting pellet was washed once with assay buffer (150 mM NaCl, 10 mM $Na_2KPO_4$, 1 mM EGTA, pH 7.4), recentrifuged and the pellet resuspended in assay buffer (4–20 mg protein/ml) and was stored at –80° C. until assayed.

CoA-IT activity

CoA-IT activity was measured in 1.5 ml centrifuge tubes in a total volume of 100 ul. Microsomes were diluted in assay buffer to the desired protein concentration (6–20 ug/tube). The reaction was initiated by addition of [$^3$H]1-alkyl-2-lyso-sn-glycero-3-phosphocholine (GPC) (~0.1 uCi/tube) and 1 µM final cold 1-alkyl-2-lyso-GPC in assay buffer with 0.25 mg/ml fatty acid-poor bovine serumalbumin (BSA) (Calbiochem, La Jolla, Calif.). [$^3$H]1-alkyl-2-lyso-GPC, approximately 50 Ci/mmol, was from NEN-Dupont (Boston, Mass.) and cold 1-alkyl-2-lyso-GPC was from Biomol (Plymouth Meeting, Pa.). Microsomes were pretreated with desired agents for the desired time (10 minutes) before the addition of [$^3$H]1-alkyl-2-lyso-GPC. The reaction was run for the desired time (10 minutes) at 37° C. The reaction was stopped and the lipids extracted by addition of 100 ul of chloroform:methanol (1:2, v/v) followed by 100 ul of chloroform and 100 ul of 1M KCl. The samples were vortexed and centrifuged at high speed in a microfuge for 2–3 minutes. An aliquot of the chloroform-extracted materials were separated, usually by TLC in chloroform/methanol/acetic acid/water (50:25:8:4, v/v), visualized by radioscanning (Bioscan) and the product, [$^3$H]1-alkyl-2-acyl-GPC, was scraped and quantified by liquid scintillation spectroscopy. With this TLC system, the synthetic standards of 1-alkyl-2-lyso-GPC and 1-alkyl-2-acyl-GPC were well separated, with Rf values of approximately 0.25 and 0.65, respectively. Other methods can be used to separate substrate from product, including but not limited to column chromatography, affinity chromatography and post reaction derivitization.

Protein concentration were assessed using the protein assay reagents from Bio-Rad (Richmond, Calif.).

Results

A variety of compounds have been tested in this assay to determine its selectivity and inability to detect trivial, non-selective inhibitors. Inhibitors of 5-lipoxygenase (5-LO) and cyclooxygenase (CO), such as indomethicin, naproxen, 6-(4'-Fluorophenyl)-5-(4-pyridyl)-2,3-dihydroimidzo-[2,1-b]thiazole and 6-(4'-Fluorophenyl)-5-(4-pyridyl)2,3-dihydroimidzo-[2,1-b]thiazole-dioxide had no effect on CoA-IT activity at concentrations up to 100 µM. The antioxidant BHT also has no effect at concentrations up to 100 µM. Compounds which complex with phospholipids and inhibit $PLA_2$ activity, such as quinacrine and aristolochic acid have no effect on CoA-IT activity at concentrations up to 500 µM. Doxepine, a compound reported to inhibit PAF release did not inhibit CoA-IT at concentrations up to 100 µM. Sodiumdiclofenac, reported to decrease leukotriene production by altering arachidonic acid metabolism, had no effect on CoA-IT activity at concentrations up to 500 µM. These results show that the assay for CoA-IT activity is sensitive and selective.

Representative compounds which inhibit CoA-IT activity in a microsomal CoA-IT assay (assay a) at 50 µM are:

1. Ethyl 6-(3,4,5-triphenyl-2-oxo-2,3-dihydroimidazol-1-yl)hexanoate
2. Sodium7-(3,4,5-triphenyl-2-oxo-2,3-dihydroimldazol-1-yl)-heptanesulphone
3. Diethyl 7-(3-4-5-triphenyl-2-oxo-2–3-dihydroimidazol-1-yl)heptane phosphonate
4. 8-(1,4,5,-Triphenylimidazol-2-yl-oxy)octanoic acid
5. 8-(2-3-Diphenylmaleimido)octanic acid
6. 11-(2,3-Diphenylmaleimido)undecanoic acid
7. Ethyl 3-(3,4,5-triphenyl-2-oxo-2,3-dihydroimidazol-1-yl)propionate
8. Ethyl 5-(3,4,5-triphenyl-2-oxo-2,3-dihydroimidazol-1-yl)valerate
9. Ethyl 5-(1,4-5-triphenylimidazol-1-yl-oxy)valerate
10. 2-(7-Carboxyheptyl)-4,5-diphenyloxazole
11. Ethyl-6-(3-methyl-4,5-diphenyl-2-oxo-2,3-dihydroimidazol-1-yl-hexanoate
12. Ethyl-8-(4,5-diphenyl-2-oxo-2,3-dihydroimidazol-1-yl)octanoate
13. 8-[1-(1,4,5-Triphenylimidazol-2-yl-oxy)]octanoic acid, ammonium salt
14. 1-(7-Methoxycarbonylheptyl)-4,5-diphenyl-1,2,3-triazole
15. 8-(1,4,5-Triphenyllmidazol-2-yl-oxy)-octanamide
16. 1-(7-Carboxyheptyl)-2-3-4-triphenylimidazole
17. 8-(4,5-Diphenylimldazol-2-yl-thio)octanoic acid
18. 9-[1-(3,4,5-Triphenyl-2-oxo-2,3-dihydroimidazolyl)] nonanoic acid
19. 2-(9-Hydroxynonyl)-4,5-diphenyl-1,2,3-triazole
20. Diethyl 7-(1,4,5-triphenylimidazol-2-yl-oxy)heptane phosphanate
21. -(6-Ethoxycarbonylhexyl)-2,4,5-triphenylimidazole
22. Ethyl 8-(4,5-Diphenylimidazol-1-yl)octanoate
23. 11-(3,4,5-Triphenyl-2-oxo-1,2-dihydroimidazol-1-yl) undecanoic acid
24. 7-(3,4,5-Triphenyl-2-oxo-1,2-dihydroimidazol-1-yl) heptanitrile
25. 7-(3,4,5-Triphenylimidazol-1-yl-oxy)heptanitrile.
26. 1-(6-Carboxyhexyl)-2,4,5-triphenylimidazole
27. 2-(6-Carboxyheptyl)-4-5-diphenyl-1,2,3-triazole
28. 1-(8-Bromooctyl)-4,5-diphenyl-1,2,3-triazole
29. 1-(8-Carboxyoctyl)-2,4,5-triphenylimidazole
30. Ethyl [7-(3,4,5-triphenyl-2-oxo-2,3-dihydroimidazol-1-yl)methyl phosphonate
31. 2-(2-Methoxyethoxy)ethyl-8-(4,5-diphenylimidazol-1-yl)octanoate
32. 1-(8-Cyanooctyl)-4,5-diphenyl-1,2,3-triazole
33. 1-(7 Carboxyheptyl)-2-(4-methoxyphenyl)-4,5-diphenylimidazole
34. 1-(7-Ethoxycarbonylheptyl)-2-methyl-4,5-diphenylimidazole
35. Methyl 7-(3,4,5-triphenyl-2 oxo-2,3-dihydroimidazol-1-yl)-5-heptynoate
36. 2-Benzyl-1-(7-carboxyheptyl)-4,5-diphenylimidazole
37. Ethyl 8-(phenanthro[9,10-d)imidazol-1-yl)octanoate
38. 1-(7-Carboxyheptyl)-2-(4-hydroxyphenyl)-4,5-diphenylimidazole
39. Ethyl 7-(1,4,5-triphenylimidazol-2-yloxy)heptane methylphosphinate 40. 2-[4-(3-Carboxypropoxy)phenyl]-4,5 diphenylimidazole
41. 1-(7-Carboxyheptyl)-4,5,-bis(2-chlorophenyl)-2-phenylimidazole
42. 1-(7-Carboxyheptyl)-2-(4-hydroxy-3,5-diiodophenyl)-4,5-diphenylimidazole
43. 1-(7-Carboxyheptyl)-2-phenyl-4,5-bis(4-methoxyphenyl)imidazole
44. 1-(10-Carboxydecyl)-2,4,5-triphenylimidazole
45. 1-(7-Carboxyheptyl)-2-phenylimidazole
46. 1-(7-Ethoxycarbonyl)-4-phenylimidazole
47. 8-(3,4-Diphonylpyrazol-1-yl)octanoic acid
48. 1-(8-carboxy-8,8-dimethyloctyl)-2,4,5-triphenylimidazole
49. 1-(7 Carboxyheptyl)-2-octylthio-4,5-diphenylimidazole
50. 4-[4-(2,4,5-Triphenylimidazol-1-yl)butyloxy]benzoic acid
51. 1-(Carboxyheptyl)-2-heptyl-4,5-diphenylimidazole
52. 1-(7-(5-Tetrazolyl)heptyl]-2,4,5-triphenylimidazole
53. Sodium 7-(2,4,5-triphenylimidazole-1-yl)heptane sulphonate
54. 2-[5-(1,3-dioxalan-2-yl)pentylthio]-1-(7-ethoxycarbonylheptyl)-4,5-diphenylimidazole
56. 7-(2,4,5-Triphenylimidazol-1-yl)heptane phosphonic acid (b) Arachidonic Acid Release Assay
Preparation of human neutrophils Human neutrophils were obtained in the laboratory using three different methods. One method used leukophoresis packs from normal humans and neutrophils were isolated using the histopaque-1077 technique. The blood was centrifuged at 300× g for 10 minutes. The cell pellets were resuspended in PBS composed of 137 mM NaCI, 8.8 mM Na2HPO4, 1.5 mM KH2PO4, 2.7 mM KCI (Dulbecco's Gibco Laboratories, Long Island, N.Y.) and layered over histopaque-1077 (Sigma, St. Louis, Mo.). The pellets were collected after centrifugation (300× g for 30 minutes) and washed once in PBS. The cell pellets were exposed briefly to dionized water to lyse any erythrocytes. The remaining cells were collected by centrifugation, suspended in PBS, counted and identified after cytospinning and staining. The final leukocyte preparation was of greater than 95% purity and viability.

The second method isolated human neutrophils from fresh heparinized normal blood using the Histopaque-1077 technique. The blood was layered over Histopaque-1077 (Sigma, St. Louis Mo.) and centrifuged at 400× g for 30 minutes. The cell pellets were resuspended in 35 ml of PBS and 12 ml of 6% Dextran, followed by Dextran sedimentation at room temperature for 45 minutes. The upper layer was coLlected and further centrifuged for 10 minutes at 1000 rpm. The cell pellets were exposed briefly to deionized water to lyse erythrocytes. The remaining cells were collected by centrifugation, suspended in PBS, counted and identified after cytospinning and staining. The final leukocyte preparation was of greater than 95% purity and viability.

The third method isolated human neutrophils from freshly drawn heparinized normal blood using the Percoll technique. The blood was first treated with 6% Dextran at room temperature for a 1 hour sedmination. The upper layers of plasma were collected and centrifuged at 400× g for 10 minutes. The cell pellets were resuspended in Percoll 1.070 g/ml supplemented with 5% fetal bovine serumand layered on discontinuous gradients (1.080, 1.085, 1.090, 1.095 g/ml) followed by centrifugation at 400× g for 45 minutes. The neutrophils were collected from interfaces of 1;080 and 1.085 and the 1.085 and 1.090 Percoll densities, followed by a centrifugation at 400× g for 45 minutes. The neutrophils were suspended in PBS, counted and identified after cytospinning and staining. The final leukocyte preparation was of greater than 95% purity and viability.

There was no difference noted in the response of the neutrophils nor in the effects of test compounds in neutrophils isolated by the three different techniques.

Treatment of human neutrophils

Neutrophils were suspended in PBS with 1 mM $Ca^{2+}$ and 1.1 mM $Mg^{2+}$ at concentrations of 5 to 20×106 cells per ml. Cells were added to test tubes and treated with the desired compounds for 5 to 10 minutes, then challenged with calcium ionophere A23187, 2 µM, or vehicle control, PBS containing 0.25–1 mg/ml BSA. After 5 to 20 minutes, the reactions were terminated by addition of an equal volume of chloroform:methanol (1:2, v/v) to the samples. [$^2H_8$] Arachidonic acid (50, 100 or 200 ng) was added as an internal standard and the lipids were extracted by addition of equal volumes of chloroform and distilled water. The samples were vortexed and centrifuged at high speed and the chloroform layer removed to a clean tube.

Assay for free arachidonic acid

The chloroform extract for each sample was evaporated to dryness and the material resuspended in hexane. The hexane was passed through a Silica solid phase column (500 mg), washed 2× with hexane and a fatty acid enriched fraction eluted with hexane:ethyl ether (1:1, v/v). Solvents were removed from the samples under a stream of nitrogen then the samples were convened to pentafluorobenzyl esters using pentafluorobenzyl bromide and diisopropylethylamine in acetronitrile. Solvents were removed and samples were suspended in hexane. GC/MS analysis was performed on a suitable instrument, such as a Finnigan MAT TSQ 700 GC/MS/MS/DS (San Jose, Calif.) operated as a single stage quadruple system or a Hewlett-Packard 5890 with a 5989A M5 system.

The peaks corresponding to arachidonic acid and [$^2H_8$] Arachidonic acid were identified and the areas of those peaks compared and the released arachidonic acid calculated as ng of arachidonic acid for each sample.

Protein concentrations were assessed using the protein assay reagents from Bio-Rad (Richmond, Calif.).

(c) Assay for Production of Platelet-Activating Factor (PAF)

Preparation of human neutrophils:

Blood was obtained from normal humans and neutrophils were isolated as described for the arachidonic acid release assay, above. The final leukocyte preparation was of greater than 95% purity and viability.

Treatment of human neutrophils

Neutrophils were suspended in PBS at concentrations of 5 to 20×10$^6$ cells per ml. Cells were added to test tubes and treated with the desired compounds for 5 to 10 minutes, then challenged with calcium ionophore A23187, 2 µM and 20–30 µCi of [$^3$H]acetic acid (NEN-Dupont, Boston, Mass.), or the vehicle of PBS with 0.25–1 mg/ml of the. After 5 to 20 minutes, the reactions were terminated by addition of an equal volume of chloroform:methanol (1:2, v/v) to the samples and the lipids were extracted by addition of equal volumes of chloroform and distilled water. The samples were vortexed and centrifuged at high speed and the chloroform layer removed to a clean tube.

Assay for PAF

The chloroform from each tube was evaporated to dryness and the material suspended in a small volume of chloroform or chloroform:methanol (25–100 µl) and the total material spotted on a Silica TLC plate. The plates were developed in chloroform/methanol/acetic acid/water (50:25:8:4, v/v) visualized by radioscanning (Bioscan) and the product, [$^3$H]PAF, was scraped and quantified by liquid scintillation spectroscopy. With this TLC system, the Rf value for a synthetic standard of PAF was approximately 0.33.

(d) Assay (Method) for TPA-induced Inflammation
Animals:

Male Balb/c inbred mice were obtained from Charle River Breeding Laboratories (Kingston, N.Y.). Within a single experiment mice (22–25 g) were age-matched. These in vivo experiments typically involved use of 5–6 animals/group.

TPA-induced Inflammation:

TPA (12-0-tetradecanoylphorbol 13-acetate) (Sigma Chemical Company) in acetone (4 µg/20 µl) was applied to the inner and outer surfaces of the left ear of BALB/c male mice. The thickness of both ears was then measured with a dial micrometer (Mitutoyo, Japan) at both 2 and 4 hours after treatment, and the data expressed as the change in thickness ($10^{-3}$ cm) between treated and untreated ears. The application of acetone did not cause an edematous response; therefore, the difference in ear thickness represented the response to the TPA. After measuring the edema, the inflammed left ears were removed and stored at –70° C. until they were assayed for MPO (myeloperoxidase) activity where appropriate.

Assay of Myeloperoxidase (MPO) in Inflamed Ear Tissue:

On the day of the assay, partially thawed ear tissues were minced and then homogenized (10% w/v) with a Tissumizer homogenizer (Tekmar Co.) in 50 mM phosphate buffer (pH 6) containing 0.5% HTAB. The tissue homogenates were taken through three cycles of freeze-thaw, followed by brief sonication (10 sec). The method of Bradley et al. was used with modifications as described. The appearance of a colored product from the MPO-dependent reaction of o-dianisidine (0.167 mg/ml; Sigma) and hydrogen peroxide (0.0005%; Sigma) was measured spectrophotometrically at 460 nm. Supernatant MPO activity was quantified kinetically (change in absorbance measured over 3 min, sampled at 15-sec intervals) using a Beckman DU-7 spectrophotometer and a Kinetics Analysis package (Beckman Instruments, Inc.). One unit of MPO activity is defined as that degrading one micromole of peroxide per minute at 25° C.

Statistics:

Statistical analysis was done using Student's "t" test. The $ED_{35}$ and $ED_{50}$ are values which caused a 35% and 50% (respectively) inhibition of the inflammatory response and were calculated by regression analysis of the dose response data.

The compound of Example 3 demonstrated a positive inhibition in this animal model demonstrating a clear utility in the treatment of topically administered dieases associated with inflammation as noted herein such as, but not limited to, inflammatory bowel disease, contact dermatoses, actinic keratosis, psoriasis, or conjuctivitis.

Alternatively, a dosage of 50 µM/kg per os dose may be administered to the animals and the assay conducted accordingly. A positive in vivo response would similarly be indicative for use in disease states which require systemic treatments, as described herein, such as, but not limited to, asthma, adult respiratory distress syndrome or allergic responses.

(e) Methods for the evaluation of CoA-IT inhibitors in intact cells

Measurement of the effect of CoA-IT inhibitors on the transfer of [$^3$H]arachidonate into 1-ether phospholipids in non-stimulated inflammatory cells can be accomplished by general application of the following specific method. Human neutrophils were isolated and resuspended ($5 \times 10^7$/ml) in Hanks Balanced Salt Solution (HBSS; Gibco). [5,6,8,9,11,12,14,15-$^3$H]-Arachidonic acid (100 Ci/mmol; New England Nuclear) complexed to 200 µl HBSS containing 0.25 mg/ml HSA was added to the cell suspension (1 µCi/ml). The cells were incubated with gentle shaking at 37° C. for 5 min. The reaction was terminated by the addition of 40 ml ice-cold HBSS containing HSA (0.25 mg/ml). The cells were then removed from the supernatant fluid by centrifugation (225 g, 8 min). Unincorporated [$^3$H]-arachidonic acid was completely removed by two more washes of HBSS containing 0.25 mg/ml HSA. The neutrophils were resuspended in fresh buffer, exposed to various concentrations of a CoA-IT inhibitor or its vehicle and incubated without stimulation for 2 hrs. At that time, the tubes containing the cells and buffer were extracted (Bligh & Dyer [Can. J. Biochem. Physiol. (1959) 37, 911–917]) and the phospholipid classes separated and collected by normal phase HPLC, using a Ultrasphere Silica column (4.6 mm×250 mm; Rainin) eluted with hexane/2-propanol/ethanol/phosphate buffer (pH 7.4)/acetic acid (490:367:100:30:0.6 v/v) for 5 min at a flow rate of 1 ml/min. The amount of phosphate buffer in the eluting solvent was increased to 5% over 10 min and this solvent composition was maintained until all the phospholipid classes had eluted from the column (30–40 min) (Chilton, F. H. [Methods Enzymol. (1990) 187, 157–166]). The phospholipids were converted into diradylglycerols by addition of phospholipase C, 20 units-40 units of *Bacillus cereus* phospholipase C (Sigma Type XIII) in 100 mM Tris HCl buffer (pH 7.4) for 2.5–6 hr, then converted into 1,2-diradyl-3-acetylglycerols by incubation with acetic anhydride and pyridine (Chilton, F. H. [Methods Enzymol. (1990) 187, 157–166]). The phospholipid subclasses were separated by TLC in benzene/hexane/ethyl ether (50:45:4, v/v), located by image analysis (Bioscan) and the amount of radioactivity in each class was determined by zonal scraping and liquid scintillation counting.

The following is the method for assessing the ability of a compound to alter arachidonate content of cellular phospholipids, which can be generalized for any desired cell. Specifically, mouse bone marrow-derived mast cells are removed from culture and provided with exogenous [$^3$H] arachidonic acid for 30 minutes. The labeled arachidonic acid which had not been incorporated into the cells is then removed by washing the cells 2 times with an albumin-containing buffer. At that point, the cells are treated with various concentrations of CoA-IT inhibitors and then placed back in culture for 24–48 hours. The phospholipids are extracted by the method of Bligh and Dyer [Can. J. Biochem. Physiol. (1959) 37, 911–917] and phospholipids separated by normal phase HPLC by the method of Chilton [Methods Enzymol. (1990) 187, 157–166]. The radioactive and mole quantities of arachidonate in complex lipids are determined. At this point, cellular lipid extracts are treated with KOH (0.5M) to remove fatty acids from complex lipids (phospholipids) and the quantities of arachidonate in these extracts can then be determined by various methods, including gas chromatography and mass spectrometry (Chilton [Methods Enzymol. (1990) 187, 157–166]).

6. Assay for screening chemical compounds for potential anti-inflammatory action An assay method for determining the inhibitory activity of compounds for CoA-IT and the inhibition of PAF and free arachidonic acid production is also encompassed by the invention. The method comprises (1) measuring the inhibition of the CoA-independent acylation of lysophospholipids in broken cell preparations of said compounds; (2) measuring the inhibition of PAF production in activated inflammatory cells of said compounds; and/or (3) measuring the inhibition of free arachidonic acid release in activated inflammatory cells of said compounds; and/or (4) measuring deletion of arachidonate form phospholipds of inflammatory cells by said compounds; and/or (5) measuring the anti-inflammatory activity of said compounds in animal models of inflammation. The activity of the compound is determined by inhibition of at least 20% of the activities of CoA-IT, PAF or free arachidonic acid release. This assay method provides a means wherein chemical compounds can be easily screened for CoA-IT inhibiting activity.

As used herein, various abbreviations and explanations are as follows: [$^3$H], a molecule that contains tritium atoms, a radioactive isotope; A23187, a compound that allows free entry of calcium into a cell; AA, arachidonic acid; arachidonate, arachidonic acid contained within a phospholipid; free arachidonic acid, arachidonic acid that is not contained within a phospholipid; [$^2$H$_8$]arachidonic acid, the form of arachidonic acid labeled with 8 deuterium atoms, a stable isotope; 1-alkyl, 1-O-alkyl; 1-alkenyl, 1-O-alk-1'-enyl; BSA, bovine serum albumin; CoA, coenzyme A; CoA-IT, CoA-independent transacylase; DTT, dithiothreitol; EGTA, [ethylenebis(oxyethylenenitrilo)]tetra acetic acid, a calcium chelator; GPC, sn-glycero-3-phosphocholine; EDTA, a metal ion chelator; GPE, sn-glycero-3-phosphoethanolamine; GC/MS, gas chromatography and mass spectrometry; 5HETE, 5(S)-hydroxyeicosa- 6,8,11,14-tetraenoic acid; 15HETE, 15(S)-hydroxyeicosa-5,8,11,13-tetraenoic acid; HL-60, American Type Tissue Culture designated cell line similar to a monocyte; LTB$_4$, leukotriene B$_4$; LTC$_4$, leukotriene C$_4$; LTD$_4$, leukotriene D$_4$; lyso PAF, 1-alkyl-2-lyso-GPC, lyso platelet-activating factor; PLA$_2$, phospholipase A$_2$; PBS, phosphate buffered saline; PAF, platelet activating factor, 1-alkyl-2-acetyl-GPC; PL, phospholipid; PC, phosphatidylcholine; PE, phosphatidylethanolamine, PI, phosphatidylinositol; PMN, polymorphonuclear neutrophilic cell, neutrophil; PS phosphatidylserine; Rf, the distance a compound travels as a fraction of the solvent front; TLC, thin layer chromatography; U937, American Type Tissue Culture designated cell line similar to a monocyte.

Compounds

Illustrative of compounds useful in this inventions are the compounds of Formulas (I) to (VI), as noted below. Compounds which are also useful in the instant invention and which do not specifically fall within any of the structures herein are further described below. Another invention is the pharmaceutical compositions for use herein comprising the compounds as noted herein, and in particular the pharmacuetical compositions comprising a compounds of Formulas (I) to (VI), or a pharmacuetically acceptable salt thereof and a pharmacuetically acceptable carrier or diluent.

Compounds of Formula (I) are represented by the structure:

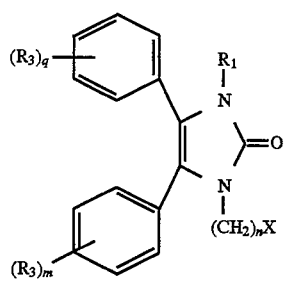

(I)

wherein

R$_1$ is hydrogen, C$_{1-4}$alkyl, optionally substituted phenyl or optionally substituted heteroaryl;

n is an integer having a value of 4 to 12;

X is 5-tetrazolyl, SO$_3$H, P(O)(OR$_2$)$_2$, P(O)(OH)$_2$, or P(O)(R$_2$)(OR$_2$);

R$_2$ is hydrogen or C$_{1-4}$alkyl;

R$_3$ is independently C$_{1-4}$ alkyl, halo substituted C$_{1-4}$ alkyl, halogen, hydroxy or C$_{1-4}$ alkoxy;

m is an integer having a value of 1 to 3;

q is an integer having a value of 1 to 3;

or a pharmaceutically acceptable salt thereof.

Suitably, R$_1$ is hydrogen, C$_{1-4}$alkyl, optionally substituted phenyl or optionally substituted heteroaryl. Preferably R$_1$ is optionally substituted phenyl; most preferably an unsubstituted phenyl.

Suitably, n is 4 to 12; preferably n is 4 to 8, most preferably n is 6 or 7.

Suitably m and p are 1 to 3, preferably 1.

Suitably, X is 5-tetrazolyl, SO$_3$H, P(O)(OR$_2$)$_2$, P(O)(OH)$_2$, or P(O)(R$_2$)(OR$_2$) in which R$_2$ is independently a C$_{1-4}$alkyl group. Preferably X is P(O)(OEt)$_2$ or P(O)(Me)(OEt).

Suitable R$_3$ substituent include, for example, 1 to 3 groups which may be the same or different and are selected from C$_{1-4}$alkyl, such as methyl or ethyl, haloC$_{1-4}$alkyl such as CF$_3$, halogen, such as F or Cl, hydroxy and C$_{1-4}$alkoxy, such as methoxy. Preferably R$_3$ is hydrogen.

Suitable heteroaryl groups include, for example, saturated or unsaturated 5- or 6- membered rings comprising 1 to 3 heteroatoms selected from nitrogen, oxygen and sulphur. Preferably such rings include, for example, thienyl and furyl rings.

Compounds of structure (I) include:

1. Diethyl-7-(3,4,5-triphenyl-2-oxo-2,3-dihydroimidazol-1-yl)heptane phosphonate;
2. Ethyl-7-(3,4,5-triphenyl-2-oxo-2,3-dihydroimidazol-1-yl)methyl-phosphinate;
3. 7-(3,4,5-triphenyl-2-oxo-2,3-dihydroimidazol-1-yl) heptane phosphonic acid;
4. Sodium 7-(3,4,5-triphenyl-2-oxo-2,3-dihydroimidazol-1-yl)heptane sulphonate;
5. Diisopropyl-7-(3,4,5-triphenyl-2-oxo-2,3-dihydroimidazol-1-yl)heptane phosphonate;
6. Dimethyl-7-(3,4,5-triphenyl-2-oxo-2,3-dihydroimidazol-1-yl)heptane phosphonate;
7. Diethyl-6-(3,4,5-triphenyl-2-oxo-2,3-dihydroimidazol-1-yl)hexane phosphonate; or
8. Diethyl-8-(3,4,5-triphenyl-2-oxo-2,3-dihydroimidazol-1-yl)octane phosphonate.

A preferred compound of Formula (I) is 7-(3,4,5-triphenyl-2-oxo-2,3-dihydroimidazol-1-yl)-heptanephosphonate.

Another aspect of the present invention is the novel compounds and their pharmaceutical compositions of Formula (I) which are:

Diisopropyl-7-(3,4,5-triphenyl-2-oxo-2,3-dihydroimidazol-1-yl)heptane phosphonate;

Dimethyl-7-(3,4,5-triphenyl-2-oxo-2,3-dihydroimidazol-1-yl)heptane phosphonate;

Diethyl-6-(3,4,5-triphenyl-2-oxo-2,3-dihydroimidazol-1-yl)hexane phosphonate;

Diethyl-8-(3,4,5-triphenyl-2-oxo-2,3-dihydroimidazol-1-yl)octane phosphonate; and the pharmaceutically acceptable salts thereof.

The compounds of structure (I) can be prepared using procedures analogous to those known in the art. The present invention therefore provides in a further aspect a process for the preparation of compounds of structure (I) in which X is other than 5-tetrazolyl which comprises reaction of a compound of structure (Ia):

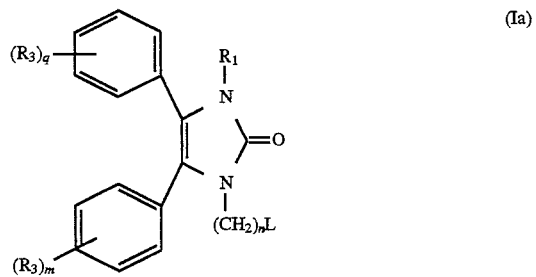

in which $R_1$, $R_3$, m, n, and p are as described for structure (I) and L is a leaving group, with a suitable source of the group X; and optionally thereafter forming a pharmaceutically acceptable salt thereof.

Compounds of structure (I) in which X is 5-tetrazolyl, can be prepared from compounds of structure (Ia) by standard techniques, for example, when L is bromine, by reaction with sodium cyanide in a suitable solvent such as dimethylsulphoxide, to form the intermediate compound in which L is cyano; followed by reaction with tri-n-butyl tin azide in, for example, tetrahydrofuran to form the desired compound of structure (I).

Suitable leaving groups L will be apparent to those skilled in the art and include, for example, halogen, such as bromine.

Suitable sources of the group X will again be apparent to those skilled in the art and include, for example, where X is $SO_3Na$, sodium sulphite.

The reaction between the compounds of structure (Ia) and the source of X is carried out in a solvent at elevated temperature. Preferably, for example where X is $SO_3Na$ the reaction is carried out in aqueous ethanol at reflux temperature for a suitable period to allow the reaction to go to completion; and where X is a phosphorus containing group the reaction is carried out in an organic solvent such as toluene or xylene.

The compounds of structure (Ia) can be prepared from compounds of structure (Ib):

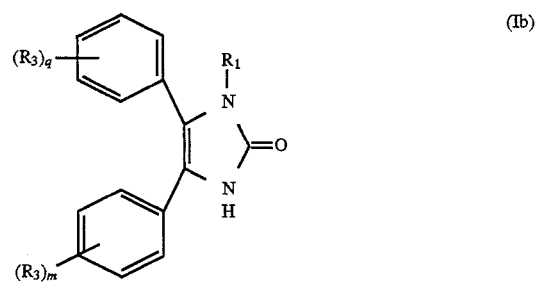

in which $R_1$, $R_3$, m, n, and p are as described for structure (I) by reaction with, for example, a compound of formula $L^1(CH_2)_nL$, in which L and $L^1$ are suitable leaving groups, in the presence of a base such as potassium carbonate and a suitable solvent such as butanone. Suitable groups L are as described for structure (Ia). Suitable groups $L^1$ will be apparent to those skilled in the art, and include halogen, in particular bromine.

Compounds of structure (Ib) are known or can be prepared by standard techniques.

The compounds of Examples 1 to 8 found in the Synthetic Chemistry section serve to illustrate the preparation of compounds representative of structure (I).

Compounds of Formula (II) are represented by the structure

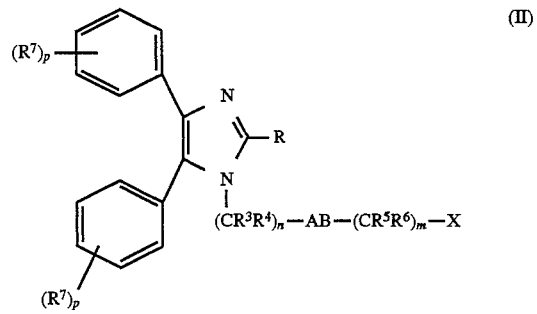

wherein

R is hydrogen, $C_{1-8}$alkyl, $C_{1-8}$alkoxy, $SC_{1-8}$alkyl, optionally substituted phenyl, phenyl $C_{1-4}$alkyl in which the phenyl group is optionally substituted, $C_{1-6}$alkylCHO or $C_{1-6}$alkylCH(OR$^1$)(OR$^2$) in which each group $R^1$ and $R^2$ is $C_{1-4}$alkyl, or together form an ethane 1,2-diyl or propane 1,3-diyl group;

n is 2 to 6 and m is 0 to 6;

$R^3$, $R^4$, $R^5$ and $R^6$ are independently hydrogen or $C_{1-4}$alkyl;

AB is a single bond, —CH=CH—, —S—, S-phenyl or O-phenyl;

X is $CO_2H$ or a group hydrolysable to $CO_2H$, 5-tetrazolyl, $SO_3H$, $P(O)(OR)_2$, $P(O)(OH)_2$, or $P(O)(R)(OR)$ in which R is hydrogen or $C_{1-4}$alkyl;

$R^7$ is independently selected from hydrogen, $C_{1-4}$alkyl, halo$C_{1-4}$alkyl, halogen, hydroxy, or $C_{1-4}$alkoxy;

p is an integer having a value of 1 to 3;

or a pharmaceutically acceptable salt thereof;

provided that:

a) when X is 5-tetrazolyl, $R^7$ is hydrogen, R is phenyl, and AB is a bond, then n+m are equal to a number greater than 6;

b) when X is $CO_2H$, AB is a bond, n+m is equal to 7, and ($R^7$)p is the same and is hydrogen, then R is not hydrogen;

c) when X is $CO_2H$, AB is a bond, n+m is equal to 7, and $(R^7)p$ is the same and is hydrogen, then R is not alkyl or hydrogen;

d) when X is $CO_2H$, AB is a bond, n+m is equal to 7, and $(R^7)p$ is the same and is 4-hydroxy, then R is not phenyl;

e) when X is $CO_2H$, AB is a bond, n+m is equal to 7, and $(R^7)p$ is the same and is 4-Methoxy or is 4-hydroxy, then R is not hydrogen;

f) when X is $CO_2H$, AB is a bond, n+m is equal to 7, and $(R^7)p$ is the same and is 2-chloro, then R is not hydrogen;

g) when $(R^7)p$ is the same and is hydrogen, R is phenyl, n is 4, m is 0, and AB is O-phenyl then X is not $CO_2$—$C_{1-6}$alkyl;

h) when R is hydrogen, $(R^7)p$ is the same and is hydrogen, AB is a bond, n+m is equal to 7, than X is not $CH_3O$—$(CH_2)_2$—O—$(CH_2)_2$—O—$C(O)$—;

i) when X is $CO_2$—$C_{1-6}$alkyl; AB is a bond, n+m is equal to 7, and $(R^7)p$ is the same and is hydrogen, then R is not phenyl or 4-methoxyphenyl;

j) when X is $CO_2$—$C_{1-6}$ alkyl, AB is a bond, n+m is equal to 7, and $(R^7)p$ is the same and is 4-bromo or 4-methoxy, then R is not hydrogen;

k) when X is $CO_2$—$C_{1-6}$alkyl, AB is a bond, n+m is equal to 7, and $(R^7)p$ is the same and is hydrogen, then R is not 2-(4-methoxybenzyl);

l) when $(R^7)p$ is the same and is hydrogen, R is phenyl, AB is a bond n+m is equal to 10, then X is not $CO_2$—$C_{1-6}$alkyl;

m) when $(R^7)p$ is the same and is hydrogen, R is phenyl, n is 4, m is 0 and AB is O-phenyl, then X is not $CO_2$—$C_{1-6}$alkyl;

n) when AB is —S—, n is 5 or 6, and m is 1 then X is $CO_2H$; or a pharmaceutically acceptable salt thereof.

Suitably, p is 1 to 3, and $R^7$ is independently selected from hydrogen, $C_{1-4}$alkyl, halo$C_{1-4}$alkyl, such as $CF_3$, halogen, hydroxy or $C_{1-4}$alkoxy. Preferably $R^7$ is hydrogen.

Suitably, R is hydrogen, $C_{1-8}$alkyl, $C_{1-8}$ alkoxy, $SC_{1-8}$alkyl, optionally substituted phenyl, phenyl $C_{1-4}$alkyl in which the phenyl group is optionally substituted, $C_{1-6}$alkylCHO or $C_{1-6}$alkylCH$(OR^1)(OR^2)$ in which each group $R^1$ and $R^2$ is $C_{1-4}$alkyl, or together form an ethane 1,2-diyl or propane 1,3-diyl group.

Preferably R is $C_{1-4}$alkyl or optionally substituted phenyl. When R is an optionally substituted phenyl the substituent include, for example, 1 to 3 groups which may be the same or different and are selected from $C_{1-4}$alkyl, halo$C_{1-4}$alkyl, such as $CF_3$, halogen, hydroxy and $C_{1-4}$alkoxy.

Suitably, n and m together are 4 to 12, preferably 4 to 8, and most preferably 6 or 7.

Suitably, $R^3$, $R^4$, $R^5$ and $R^6$ are the same or different and are each hydrogen or $C_{1-4}$alky; Preferably, $R^3$, $R^4$, $R^5$ and $R^6$ are the same and are each hydrogen.

Suitably, AB is a single bond, —CH═CH—, S-phenyl or O-phenyl. Preferably, AB is a single bond.

Suitably, X is $CO_2H$ or a group hydrolysable to $CO_2H$, 5-tetrazolyl, $SO_3H$, $P(O)(OR)_2$, $P(O)(OH)_2$, or $P(O)(R)(OR)$ in which R is hydrogen or $C_{1-4}$alkyl. Preferably X is $CO_2H$, a group hydrolysable to $CO_2H$ or 5-tetrazolyl.

Suitable heteroaryl groups include, for example, saturated or unsaturated 5- or 6-membered rings comprising 1 to 3 heteroatoms selected from nitrogen, oxygen and sulphur. Preferably such rings include, for example, thienyl and furyl rings.

Suitable groups X, hydrolysable to $CO_2H$ include for example, nitriles, amides and ester groups. Examples of ester groups are $C_{1-6}$alkyl esters and optionally substituted benzyl esters. Particular ester groups include mono-$C_{1-4}$alkoxycarbonyl groups such as ethoxycarbonyl and methoxycarbonyl, and tri-$C_{1-4}$alkoxy carbonyl groups such as methoxyethoxyethoxy carbonyl groups ($CH_3O(CH_2)_2O(CH_2)_2O$—$C(O)$—).

Compounds of Formula (II) include:

1-(7-Ethoxycarbonylheptyl)-2,4,5-triphenylimidazole;

1-(7-Carboxyheptyl)-2,4,5-triphenylimidazole;

1-(7-Methoxycarbonylheptyl)-2,4,5-triphenylimidazole;

1-(6-Ethoxycarbonylhexyl)-2,4,5-triphenylimidazole;

1-(6-Carboxyhexyl)-2,4,5-triphenylimidazole;

1-(8-Carboxyoctyl)-2,4,5-triphenylimidazole;

1-(10-Carboxydecyl)-2,4,5-triphenylimidazole;

1-(7-Ethoxycarbonylheptyl)-2-methyl-4,5-diphenylimidazole;

1-(7-Carboxyheptyl)-2-methyl-4,5-diphenylimidazole;

1-[7-(5-Tetrazolylheptyl]-2,4,5-triphenylimidazole;

2-(2-Methoxyethoxy)ethyl-8-(2,4,5-triphenylimidazol-1-yl)octanoate;

Ethyl 8-(4,5-diphenylimidazol-1-yl)octanoate;

8-(4,5-Diphenyl-imidazol-1-yl)octanoic acid;

2-(2-Methoxyethoxy)ethyl-8-(4,5-diphenylimidazole-1-yl)octanoate;

1-(7-Ethoxycarbonylheptyl)2-(4-methoxyphenyl)-4,5-diphenylimidazole;

1-(7-Carboxyheptyl)-2-(4-methoxyphenyl)-4,5-diphenylimidazole;

1-(7-Carboxyheptyl)-2-(4-hydroxyphenyl)-4,5-diphenylimidazole;

1-(7-Carboxyheptyl)-2-(4-hydroxy-3,5-diiodophenyl)-4,5-diphenylimidazole;

2-Benzyl-1-(7-ethoxycarbonylheptyl)-4,5-diphenylimidazole;

2-Benzyl-1-(7-carboxyheptyl)-4,5-diphenylimidazole;

1-(7-Ethoxycarbonylheptyl)-2-[4-octyloxyphenyl]-4,5-diphenylimidazole;

1-(7-Carboxyheptyl)-2-[4-octyloxyphenyl]-4,5-diphenylimidazole;

1-(7-Ethoxycarbonylheptyl)-2-octylthio-4,5-diphenylimidazole;

1-(7-Carboxyheptyl)-2 octylthio-4,5-diphenylimidazole;

1-(7-Ethoxycarbonylheptyl)-4,5-bis-4-hydroxyphenyl)-imidazole;

4,5-Bis(2-chlorophenyl)-1-(7-ethoxycarbonyl-heptyl) imidazole;

4,5-Bis(2-chloro-phenyl)-1-(7-ethoxycarbonylheptyl)-2-phenylimidazole;

1-(7-Carboxyheptyl)-4,5-bis-(2-chlorophenyl)-2-phenylimidazole;

1-(7-Ethoxy-carbonylheptyl)-4,5-bis-(4-methoxyphenyl)-2-phenylimidazole;

1-(7-Carboxyheptyl)-4,5-bis(4-methoxy-phenyl)-2-phenylimidazole;

1-(7-Ethoxycarbonylheptyl)-2-heptyl-4,5-diphenylimidazole;

1-(7-Carboxyheptyl)-2-heptyl-4,5-diphenylimidazole;

7-(1,2,4-Triphenylimidazolyl)-hept-5-ynoic acid;

9-(1,2,4-Triphenylimidazolyl)-2,2-dimethylnonanoic acid;

4-[4-(2,4,5-Triphenylimidazolyl)butyloxy]benzoic acid;

7-(2,4,5-Triphenylimidazol-1-yl)heptanesulphonate;
Sodium 7-(2,4,5-Triphenylimidazol-1-yl)heptanesulphonate;
7-(2,4,5-Triphenylimidazol-1-yl)heptanephosphonate;
7-(2,4,5-Triphenylimidazol-1-yl)heptanephosphonic acid;
Ethyl 8-(phenanthro[9,10-d]imidazol-1-yl)octanoate; or
1-(7-Carboxyheptyl)-2-(5-[1,3-dioxalan-2-yl]pentylthio)-4,5-diphenyl imidazole.

Preferred compounds of Formula (II) include:
1-(7-Carboxyheptyl)-2-heptyl-4,5-diphenylimidazole;
1-(7-(5-Tetrazolylheptyl)-2,4,5-triphenylimidazole;
1-(10-Carboxydecyl)-2,4,5-triphenylimidazole;
4-[4-(2,4,5-triphenylimidazolyl)butyloxy]benzoic acid;
9-(1,2,4-tri-phenylimidazolyl)-2,2-dimethylnonanoic acid;
1-(8-Carboxyoctyl)-2,4,5-triphenylimidazole;
1-(7-Carboxy-heptyl)-2-(4-hydroxy-3,5-diiodophenyl)-4,5-diphenylimidazole;
Ethyl 8-(4,5-diphenylimidazol-1-yl)octanoate;
1-(7-Ethoxycarbonyl-heptyl)-2-methyl-4,5-diphenylimidazole;
1-(7-Carboxyheptyl)-2-(4-hydroxyphenyl)-4,5-diphenylimidazole;
1-(7-carboxyheptyl)-2,4,5-triphenylimidazole;
1-(6-ethoxy-carbonylhexyl)-2,4,5-triphenylimidazole;
1-(6-carboxyhexyl)-2,4,5-triphenylimidazole;
2-(2-methoxyethoxy)ethyl 8-(4,5-diphenylimidazole-1-yl)octanoate;
1-(7-carboxyheptyl)-2-(4-methoxyphenyl)-4,5-diphenylimidazole;
2-benzyl-1-(7-carboxyheptyl)-4,5-diphenylimidazole;
1-(7-carboxyheptyl)-4,5-bis(2-chloro-phenyl)-2-phenylimidazole;
1-(7-carboxyheptyl)-4,5-bis(4-methoxy-phenyl)-2-phenylimidazole;
7-(2,4,5-tri-phenylimidazol-1-yl)heptane-sulphonate;
7-(2,4,5-triphenylimidazol-1-yl)heptanephosphonic acid; or
Ethyl 8-(phenanthrimidazol-1-yl)octanoate.

More preferred compounds of Formula (II) are:
1-(7-Carboxyheptyl)-2-heptyl-4,5-diphenylimidazole;
1-(7-(5-Tetrazolylheptyl)-2,4,5-triphenylimidazole;
1-(10-Carboxydecyl)-2,4,5-triphenylimidazole;
4-[4-(2,4,5-triphenylimidazolyl)butyloxy]benzoic acid;
9-(1,2,4-tri-phenylimidazolyl)-2,2-dimethylnonanoic acid;
1-(8-Carboxyoctyl)-2,4,5-triphenylimidazole;
1-(7-Carboxy-heptyl)-2-(4-hydroxy-3,5-diiodophenyl)-4,5-diphenylimidazole;
Ethyl 8-(4,5-diphenylimidazol-1-yl)octanoate;
1-(7-Ethoxycarbonyl-heptyl)-2-methyl-4,5-diphenylimidazole; or
1-(7-Carboxy-heptyl)-2-(4-hydroxyphenyl)-4,5-diphenylimidazole.

Most preferred compounds of Formula (II) are:
1-(7-Carboxyheptyl)-2-heptyl-4,5-diphenylimidazole;
1-(7-(5-Tetrazolylheptyl)-2,4,5-triphenylimidazole; or
1(10-Carboxydecyl)-2,4,5-triphenylimidazole.

The compounds of structure (II) can be prepared using procedures analogous to those known in the art. The present invention therefore provides in a further aspect a process for the preparation of compounds of structure (II) which comprises:

(a) for compounds other than those in which X is 5-tetrazolyl, reaction of a compound of structure (IIa):

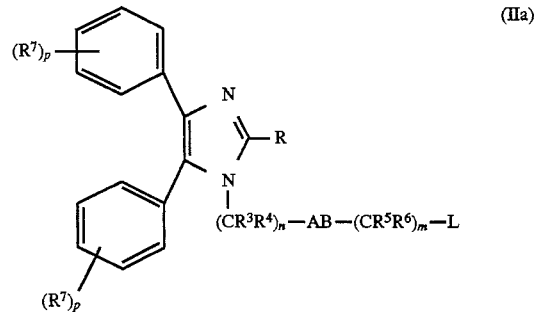

in which Ar, R, $R^3$, $R^4$, $R^5$, $R^6$, $R^7$, AB, n, p, and m are as described for structure (II) and L is a leaving group, with a suitable source of the group X;

(b) reaction of a compound of structure (IIb):

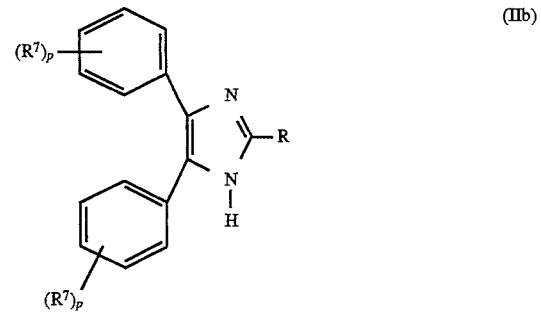

in which R and $R^7$ are as described for structure (II) with a compound of structure (IIc):

in which $R^3$, $R^4$, $R^5$, $R^6$, AB, n, m and X are as described for structure (II) and L is a leaving group; or (c) for compounds in which A is other than a bond or —CH=CH—, reaction of a compound of structure (IId):

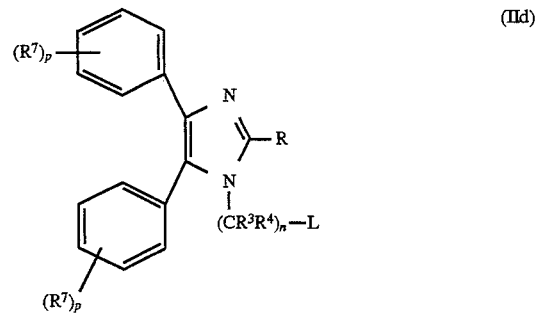

in which Ar, R, $R^3$, $R^4$ $R^7$, and n are as described for structure (II) and L is a leaving group, with a compound of structure (IIe):

in which $A^1B^1$ is —C≡C—, S, O, SPh or OPh, $R^5$, $R^6$, m and X are as described for structure (II) and L' is hydrogen or a metal;

(d) for compounds in which X is 5-tetrazolyl reaction of a compound of structure (IIa) in which L is CN, with tri-n-butyl tin azide, and optionally thereafter converting one group X into another group X, and optionally forming a salt.

Suitable leaving groups L will be apparent to those skilled in the art and include, for example, halogen, such as bromine, and sulphonic acid derivatives such as tosylate and mesylate.

Suitable metals include, for example, alkali metals such as sodium or lithium.

Suitable sources of the group X will again be apparent to those skilled in the art and include, for example, where X is $SO_3Na$, sodium sulphite.

The reaction between the compounds of structure (IIa) and the source of X is carried out in a solvent at elevated temperature. Preferably, for example where X is $SO_3Na$ the reaction is carried out in aqueous ethanol at reflux temperature for a suitable period to allow the reaction to go to completion; and where X is a phosphorus containing group the reaction is carried out in an organic solvent such as toluene or xylene.

The reaction between compounds of structure (IIb) and structure (IIc) can be carried out in an organic solvent in the presence of a base, at a temperature of between ambient and the reflux temperature of the solvent used. Suitable solvents include, for example, $C_{1-4}$alkanols such as methanol or ethanol, dimethyl formamide and butanone, and suitable bases include, for example, potassium carbonate, sodium hydroxide and sodium hydride.

The reaction between compounds of structure (IId) and structure (IIe) is carded out in a suitable solvent in the presence of a base at a temperature of between ambient and the reflux temperature of the solvent used.

Suitable solvents and reagents include, for example, potassium carbonate as the base in butanone as solvent, and sodium in methanol as a solvent.

Compounds of structure (II) in which X is 5-tetrazolyl, can be prepared from compounds of structure (IIa) by standard techniques, for example, when L is bromine, by reaction with sodium cyanide in a suitable solvent such as dimethylsulphoxide, to form the intermediate compound in which L is cyano; followed by reaction with tri-n-butyl tin azide in, for example, tetrahydrofuran to form the desired compound of structure (II).

The intermediate compounds of structures (IIa), (IIb), (IIc), (IId) and (IIe) are known or can be prepared by standard techniques.

Examples 9 to 49 found in the synthetic chemistry section serve to illustrate the preparation of compounds representative of structure (II).

The compounds of Formula (III) are represented by the structure

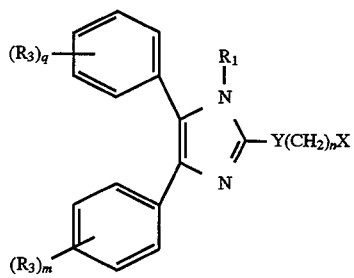

(III)

wherein $R_1$ is hydrogen, $C_{1-4}$alkyl, optionally substituted phenyl or optionally substituted heteroaryl;

n is 4 to 12;

Y is oxygen or sulfur;

X is 5-tetrazolyl, cyano, $SO_3H$, $P(O)(OR_2)_2$, $P(O)(OH)_2$, or $P(O)(R_2)(OR_2)$;

$R_2$ is hydrogen or $C_{1-4}$alkyl;

$R_3$ is independently hydrogen, $C_{1-4}$alkyl, halo substituted $C_{1-4}$alkyl, halogen, hydroxy or $C_{1-4}$alkoxy;

m is an integer having a value of 1 to 3;

q is an integer having a value of 1 to 3;

provided that when X is cyano, $R_1$ is an optionally substituted phenyl;

or a pharmaceutically acceptable salt thereof.

Suitably, $R_1$ is hydrogen, $C_{1-4}$alkyl, optionally substituted phenyl or optionally substituted heteroaryl. Preferably $R_1$ is optionally substituted phenyl; most preferably an unsubstituted phenyl.

Suitably, n is 4 to 12; preferably n is 4 to 8, most preferably n is 6 or 7.

Suitably Y is oxygen or sulphur; preferably Y is oxygen.

Suitably m and p are 1 to 3, preferably 1.

Suitably, X is 5-tetrazolyl, $SO_3H$, $P(O)(OR_2)_2$, $P(O)(OH)_2$, or $P(O)(R_2)(OR_2)$ in which $R_2$ is independently a $C_{1-4}$alkyl group. Preferably X is $P(O)(OEt)_2$ or $P(O)(Me)(OEt)$.

Suitable $R_3$ substituent include, for example, 1 to 3 groups which may be the same or different and are selected from $C_{1-4}$alkyl, such as methyl or ethyl, halo$C_{1-4}$alkyl such as $CF_3$, halogen, such as F or Cl, hydroxy and $C_{1-4}$alkoxy, such as methoxy.

Suitable heteroaryl groups include, for example, saturated or unsaturated 5- or 6-membered rings comprising 1 to 3 heteroatoms selected from nitrogen, oxygen and sulphur.

Preferably such rings include, for example, thienyl and furyl rings.

Compounds of structure (III) include:

Sodium 6-(1,4,5-triphenylimidazol-2-yloxy) hexanesulphonate;

Sodium 7-(1,4,5-triphenylimidazol-2-yloxy) heptanesulphonate;

7-(1,4,5-Triphenylimidazol-2-yl-oxy) heptanemethylphosphinate;

7-(1,4,5-Triphenylimidazol-2-yl-oxy) heptanephosphonate;

Ethyl-7-(1,4,5-triphenyl-imidazol-2-yl-oxy)heptane methylphosphinate;

Diethyl-7-(1,4,5-triphenyl-imidazol-2-yl-oxy)heptane phosphonate; and 7-(3,4,5-Triphenylimidazol-1-yl-oxy)heptanitrile.

Preferred compounds of Formula (III) include:

Ethyl-7-(1,4,5-triphenyl-imidazol-2-yl-oxy)heptane methylphosphinate; and

Diethyl-7-(1,4,5-triphenyl-imidazol-2-yl-oxy)heptane phosphonate.

The compounds of structure (III) can be prepared using procedures analogous to those known in the art. The present invention therefore provides in a further aspect a process for the preparation of compounds of structure (III) in which X is other than 5-tetrazolyl which comprises reaction of a compound of structure (IIIa):

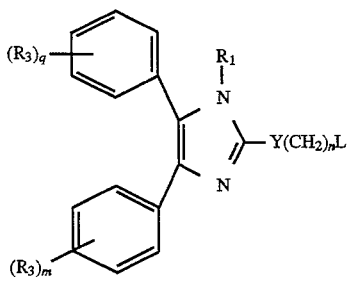

(IIIa)

in which

R$_1$, R$_3$, m, n, and p are as described for structure (III) and L is a leaving group, with a suitable source of the group X; and optionally thereafter forming a pharmaceutically acceptable salt thereof.

Compounds of structure (III) in which X is 5-tetrazolyl, can be prepared from compounds of structure (IIIa) by standard techniques, for example, when L is bromine, by reaction with sodium cyanide in a suitable solvent such as dimethylsulphoxide, to form the intermediate compound in which L is cyano; followed by reaction with tri-n-butyl tin azide in, for example, tetrahydrofuran to form the desired compound of structure (III).

Suitable leaving groups L will be apparent to those skilled in the art and include, for example, halogen, such as bromine.

Suitable sources of the group X will again be apparent to those skilled in the art and include, for example, where X is SO$_3$Na, sodium sulphite.

The reaction between the compounds of structure (IIIa) and the source of X is carried out in a solvent at elevated temperature. Preferably, for example where X is SO$_3$Na the reaction is carried out in aqueous ethanol at reflux temperature for a suitable period to allow the reaction to go to completion; and where X is a phosphorus containing group the reaction is carried out in an organic solvent such as toluene or xylene.

The compounds of structure (IIIa) can be prepared from compounds of structure (IIIb):

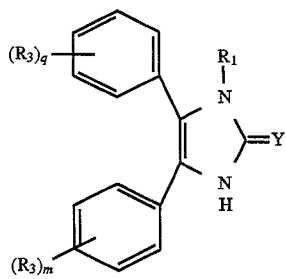

(IIIb)

in which

R$_1$, R$_3$, Y, m, n, and p are as described for structure (III) by reaction with, for example, a compound of formula L$^1$(CH$_2$)$_n$L, in which L and L$^1$ are suitable leaving groups, in the presence of a base such as potassium carbonate and a suitable solvent such as butanone. Suitable groups L are as described for structure (IIIa). Suitable groups L$^1$ will be apparent to those skilled in the art, and include halogen, in particular bromine.

Compounds of structure (IIIb) are known or can be prepared by standard techniques.

Examples 50 to 55 found in the synthetic chemistry section serve to illustrate the preparation of compounds represented by structure (III).

The compounds of Formula (IV) are represented by the structure

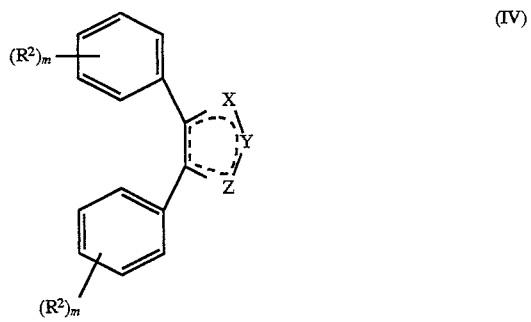

(IV)

wherein

X is nitrogen or CR$^1$;

R$^1$ is hydrogen, C$_{1-4}$alkyl, optionally substituted phenyl or optionally substituted heteroaryl;

Y is nitrogen, N(CH$_2$)$_n$A or C(CH$_2$)$_n$A

Z is nitrogen, oxygen or N(CH$_2$)$_n$A', and the dotted line indicates the optional presence of a double bond so as to form a fully unsaturated heterocyclic ring;

n is 4 to 12;

A is CO$_2$H or a group hydrolysable to CO$_2$H, OH, Br, Cyano, 5-tetrazolyl, SO$_3$H, P(O)(OR)$_2$, P(O)(OH)$_2$, or P(O)(R)(OR) in which R is hydrogen or C$_{1-4}$alkyl;

A' is CO$_2$H or a group hydrolysable to CO$_2$H, 5-tetrazolyl, SO$_3$H, P(O)(OR)$_2$, P(O)(OH)$_2$, or P(O)(R)(OR) in which R is hydrogen or C$_{1-4}$alkyl;

R$^2$ is independently C$_{1-4}$alkyl, halo substituted C$_{1-4}$alkyl, halogen, hydroxy or C$_{1-4}$alkoxy;

m is a number having a value of 1 to 3; provided that
a) X, Y and Z are not all at the same time, nitrogen;
b) when X is CR$^1$, Y and Z are not both nitrogen;
c) when Y is N(CH$_2$)$_n$A, Z is nitrogen; and
d) when Z is oxygen, Y is C(CH$_2$)$_n$A;
e) when Y is N(CH$_2$)$_n$A, X and Z are nitrogen, (R$_2$)$_m$ is the same and is hydrogen, and n is 6,7, or 8 then X is not —CO$_2$—C$_{1-6}$alkyl;
f) when Z is oxygen, Y is C(CH$_2$)$_n$A, n is 8, and (R$^2$)$_m$ is the same and is hydrogen, then X is not cyano;
g) when Z is N(CH$_2$)$_n$A', X is nitrogen, Y is nitrogen, (R$_2$)$_m$ is the same and is hydrogen, and n is 7, then X is not CO$_2$H;
h) when Y is N(CH$_2$)$_n$A, X and Z are nitrogen, (R$_2$)$_m$ is the same and is hydrogen, and n is 8 then X is not cyano; or a pharmaceutically acceptable salt thereof.

Suitably, X is nitrogen or CR$^1$; preferably X is nitrogen.

Suitably, Y is nitrogen, N(CH$_2$)$_n$A or C(CH$_2$)$_n$A; preferably, Y is nitrogen or N(CH$_2$)$_n$A; most preferably Y is N(CH$_2$)$_n$A.

Suitably, Z is nitrogen, N(CH$_2$)$_n$A or oxygen; preferably Z is nitrogen or N(CH$_2$)$_n$A; most preferably Z is nitrogen.

Suitably, n is 4 to 12, preferably 4 to 8 and most preferably 7 or 8.

Suitably, A is CO$_2$H or a group hydrolysable to CO$_2$H, OH, Br, cyano, 5-tetrazolyl, SO$_3$H, P(O)(OR)$_2$, P(O)(OH)$_2$, or P(O)(R)(OR) in which R is hydrogen or C$_{1-4}$alkyl; preferably A is CO$_2$H or a group hydrolysable to CO$_2$H, for example CO$_2$C$_{1-4}$alkyl such as CO$_2$CH$_3$ or CO$_2$C$_2$H$_5$.

Suitably, A' is CO$_2$H or a group hydrolysable to CO$_2$H, 5-tetrazolyl, SO$_3$H, P(O)(OR)$_2$, P(O)(OH)$_2$, or P(O)(R)(OR) in which R is hydrogen or C$_{1-4}$alkyl; preferably A is CO$_2$H or a group hydrolysable to CO$_2$H, for example CO$_2$C$_{1-4}$alkyl such as CO$_2$CH$_3$ or CO$_2$C$_2$H$_5$.

Suitably, R$_1$ is hydrogen, C$_{1-4}$alkyl, optionally substituted phenyl or optionally substituted heteroaryl. Preferably R$^1$ is hydrogen.

Suitable $R^2$ substituent or substituent for $R^1$ as an optionally substituted phenyl groups Ar and $R^1$ include, for example, 1 to 3 groups which may be the same or different and are selected from $C_{1-4}$alkyl, halo$C_{1-4}$alkyl, such as $CF_3$, halogen, hydroxy and $C_{1-4}$alkoxy.

Suitable heteroaryl groups include, for example, saturated or unsaturated 5- or 6-membered rings comprising 1 to 3 heteroatoms selected from nitrogen, oxygen and sulphur. Preferably such rings include, for example, thienyl and furyl rings.

Particularly preferred compounds of structure (IV) include:

1-(8-Bromooctyl)-4,5-diphenyl-1,2,3-triazole;

2-(8-Bromooctyl)-4,5-diphenyl-1,2,3-triazole;

1-(8-cyanooctyl)-4,5-diphenyl-1,2,3-triazole;

2-(8-cyanooctyl)-4,5-diphenyl-1,2,3-triazole;

2-(8-carboxyoctyl)-4,5-diphenyl-1,2,3triazole;

1-(8-carboxyoctyl)-4,5-diphenyl-1,2,3triazole;

2-(8-ethoxycarbonyloctyl)-4,5-diphenyl-1,2,3-triazole;

2-(6-Ethoxycarbonylhexyl)-4,5-diphenyl-1,2,3-triazole;

2-(6-Carboxyheptyl)-2,4,5-triphenyl-1,2,3-triazole;

2-(7-Carboxyheptyl)-4,5-diphenyloxazole;

1-(7-bromoheptyl) -4,5-diphenyloxazole;

2-(7-cyanoheptyl)-4,5-diphenyloxazole;

8-(3,4-Diphenylpyrazol-1-yl)octanoic acid;

8-(4,5-Diphenylpyrazol-1-yl)octanoic acid;

1-(7-Methoxycarbonylheptyl)-4,5-diphenyl-1,2,3-triazole;

2-(7-Methoxycarbonylheptyl)-4,5-diphenyl-1,2,3-triazole;

1-(7-Carboxyheptyl)-4,5-diphenyl-1,2,3-triazole;

8-(3,4-diphenylpyrazol-1-yl)octanoic acid;

8-(4,5-diphenylpyrazol-1-yl)octanoic acid; and 2-(9-Hydroxynonyl)-4,5-diphenyl-1,2,3-triazole.

Preferred compounds of structure (IV) include:

1-(8-Bromooctyl)-4,5-diphenyl-1,2,3-triazole;

2-(8-cyanooctyl)-4,5-diphenyl-1,2,3-triazole;

8-(3,4-diphenylpyrazol-1-yl)octanoic acid;

2-(9-Hydroxynonyl)-4,5-diphenyl-1,2,3-triazole;

2-(7-Methoxycarbonylheptyl)-4,5-diphenyltriazole;

8-(3,4-Diphenylpyrazol-1-yl)octanoic acid;

8-(4,5-Diphenylpyrazol-1-yl)octanoic acid;

2-(6-Carboxyheptyl)-2,4,5-triphenyl-1,2,3-triazole; and 2-(7-Carboxyheptyl)-4,5-diphenyloxazole.

Most preferred compounds of structure (IV) include:

2-(9-Hydroxynonyl)-4,5-diphenyl-1,2,3-triazole;

2-(7-Methoxycarbonylheptyl)-4,5-diphenyltriazole; and 1-(8-Bromooctyl)-4,5-diphenyl-1,2,3-triazole.

The compounds of structure (IV) can be prepared using procedures analogous to those known in the art. The present invention therefore provides in a further aspect a process for the preparation of compoundsofstructure(IV)whichcomprises:

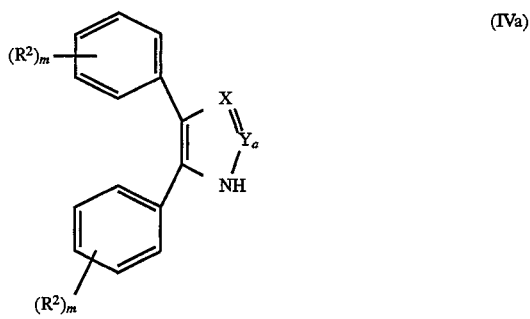

in which
$R^2$, X, m are as described for structure (IV) and $Y_a$ is N or $C(CH_2)_nA$; with a compound of structure:

$$L(CH_2)_nA \qquad (IVb)$$

in which n and A are as described for structure (IV) and L is a leaving group, or (b) reaction of a compound of structure (IVc):

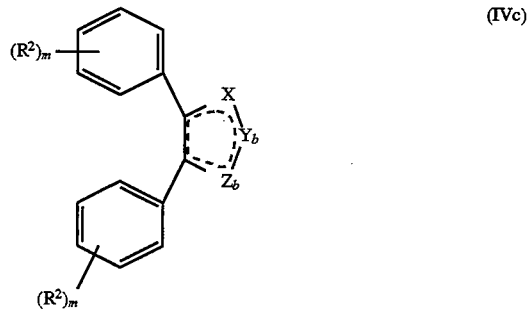

in which $R^2$, m and X are as described in structure (IV), $Y_b$ is N, $N(CH_2)_nA_b$ or $C(CH_2)_nA_b$, $Z_b$ is N, O or $N(CH_2)_nA_b$ provided that:

X, $Y_b$ and $Z_b$ are not all nitrogen,
when X is $CR^1$, $Y_b$ and $Z_b$ are not both nitrogen,
when $Y_b$ is $N(CH2)_nA_b$, $Z_b$ is nitrogen, and
when $Z_b$ is O, $Y_b$ is —$C(CH_2)_nA_b$;

$A_b$ is a group convertible to a group A as described in structure (IV), with a reagent suitable to convert the group $A_b$ into a group A and, optionally thereafter, converting one group A into another group A, and optionally forming a salt.

Suitable leaving groups L will be apparent to those skilled in the art and include, for example, halogen, such as bromine.

Suitable groups $A_b$ convertible to a group A include, for example, where A is $CO_2H$, CN groups, which can be converted into $CO_2H$ groups by reaction with, for example, sulphuric acid. Other groups and suitable reagents will be apparent to those skilled in the art.

The reaction between compounds of structures (IVa) and (IVb) can be carried out in a suitable solvent in the presence of a base at a temperature of between ambient and the reflux temperature of the solvent used. For example, compounds of structure (IV) in which X and Y are both nitrogen and Z is $N(CH_2)_nCO_2R$, can be prepared by reacting a compound of structure (IVa) in which X and $Y_a$ are both nitrogen with a compound of structure (IVb) in which L is bromine and A is $CO_2H$, in aqueous solution in the presence of sodium hydroxide as base. Further reaction of said compound of structure (IV) with, for example, p-toluene sulphonic acid in methanol gives the corresponding compound in which A is $CO_2CH_3$. The compounds of structures (IVa) and (IVb) are available commercially, or can be prepared by standard techniques.

The reaction between compounds of structure (IVc) and a reagent suitable to convert the group $A_b$ to a group A will, of course, take place under conditions which will depend on the nature of the group $A_b$. As already described, for example when $A_b$ is CN, reaction with sulphuric acid under aqueous conditions affords the desired compounds of structure (IV) in which A is $CO_2H$.

Other suitable groups and conditions will be apparent to those skilled in the art. Compounds of structure (IVc) are available commercially or can be prepared by standard procedures. For example, compounds of structure (IVc) in which X is nitrogen, $Y_b$ is $C(CH_2)_nCN$ and $Z_b$ is oxygen can be prepared via the following reaction sequence:

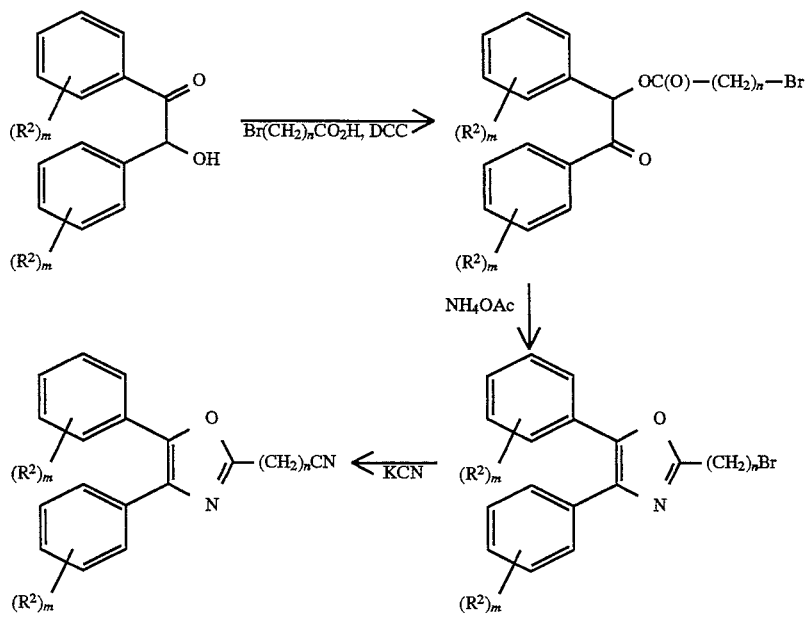

Examples 56 to 68 in the Synthetic Chemistry section serve to illustrate the preparation of compounds representative of structure (IV).

Compounds of Formula (V) are represented by the structure:

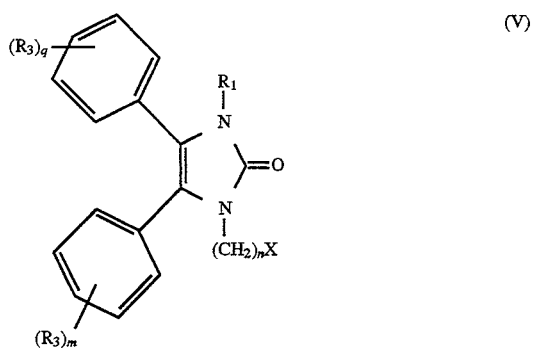

(V)

wherein $R_1$ is hydrogen, $C_{1-4}$alkyl, or optionally substituted phenyl;

n is 2 or 4 to 12;

X is cyano, $CO_2H$ or a group hydrolysable to $CO_2H$;

$R_3$ is independently $C_{1-4}$alkyl, halo substituted $C_{1-4}$alkyl, halogen, hydroxy or $C_{1-4}$ alkoxy;

q is an integer having a value of 1 to 3;

or a pharmaceutically acceptable salt thereof.

Suitably, p is 1 to 3, and $R_3$ is independently selected from hydrogen, $C_{1-4}$alkyl, halo$C_{1-4}$alkyl, such as $CF_3$, halogen, hydroxy or $C_{1-4}$alkoxy. Preferably $R_3$ is hydrogen.

Suitable when n is 2 then X is not cyano.

Suitably, $R_1$ is hydrogen, $C_{1-8}$alkyl, $C_{1-8}$ alkoxy, $SC_{1-8}$alkyl, optionally substituted phenyl, or phenyl $C_{1-4}$alkyl in which the phenyl group is optionally substituted. Preferably $R_1$ is $C_{1-4}$alkyl or optionally substituted phenyl. When $R_1$ is an optionally substituted phenyl the substituent include, for example, 1 to 3 groups which may be the same or different and are selected from $C_{1-4}$alkyl, halo$C_{1-4}$alkyl, such as $CF_3$, halogen, hydroxy and $C_{1-4}$alkoxy.

Suitably, n and m together are 4 to 12, preferably 4 to 8, and most preferably 6 or 7.

Suitable groups X, hydrolysable to $CO_2H$ include for example, nitriles, amides and ester groups. Examples of ester groups are $C_{1-6}$alkyl esters and optionally substituted benzyl esters. Particular ester groups include mono-$C_{1-4}$alkoxycarbonyl groups such as ethoxycarbonyl and methoxycarbonyl, and tri-$C_{1-4}$alkoxy carbonyl groups such as methoxyethoxyethoxy carbonyl groups ($CH_3O(CH_2)_2O(CH_2)_2O$—$C(O)$—).

Compounds of Formula (V) include:

Ethyl 3-(3,4,5-triphenyl-2-oxo-2,3-dihydroimidazol-1-yl) propionate;

Ethyl 6-(3,4,5-triphenyl-2-oxo-2,3-dihydroimidazol-1-yl) hexanoate;

Ethyl 5-(3,4,5-triphenyl-2-oxo-2,3-dihydroimidazol-1-yl) valerate;

9-[1-(3,4,5-Triphenyl-2-oxo-2,3-dihydroimidazolyl)] nonanoic acid;

7-(3,4,5-Triphenyl-2-oxo-1,2-dihydroimidazol-1-yl) heptanitrile;

Ethyl 6-(3-methyl-4,5-diphenyl-2-oxo-2,3-dihydroimidazol-1-yl)hexanoate;

11-(3,4,5-Triphenyl-2-oxo-1,2-dihydroimidazol-1-yl) undecanoic acid; or

Ethyl-8-(4,5-diphenyl-2-oxo-2,3-dihydroimidazol-1-yl) octanoate.

Compounds of Formula (VI) are represented by the structure:

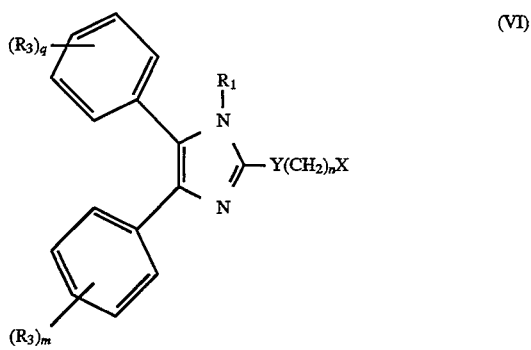

(VI)

wherein $R_1$ is hydrogen, $C_{1-4}$alkyl, or optionally substituted phenyl;

n is 4 to 12;

Y is oxygen or sulfur;

X is $CO_2H$ or a group hydrolysable to $CO_2H$;

$R_3$ is independently $C_{1-4}$alkyl, halo substituted $C_{1-4}$alkyl, halogen, hydroxy or $C_{1-4}$alkoxy;

q is an integer having a value of 1 to 3;

or a pharmaceutically acceptable salt thereof.

Suitably the variables $R_1$, $R_3$, p, n, and X as described in Formula (V) are the same for Formula (VI).

Compounds of Formula (VI) include:

Ethyl 5-(1,4,5-triphenylimidazol-1-yl-oxy)valerate;

8-(1,4,5-Triphenylimidazol-2-yl-oxy)octanamide;

8-[1,4,5-Triphenylimidazol-2-yl-oxy]octanoic acid; or

8-[1,4,5-triphenylimidazol-2-yl-oxy]octanoic acid ammonium salt.

Additional compounds which are not encompassed by Formula(s) (I) to (VI) but are useful in this invention are listed below:

7-(3,4,5-Triphenylimidazol-1-yl-oxy)heptanitrile;

8-(2,3-Diphenylmaleimido)octanoic acid;

11-(2,3-Diphenylmaleimido)undecanoic acid;

1-(7-Ethoxycarbonyl)-4-phenylimidazole;

Methyl-7-(3,4,5-triphenyl)-2-oxo-1,2-dihydroimidazol-1-yl)-5-heptynoate;

2-[4-(3-Carboxypropoxy)phenyl]-4,5-diphenylimidazole;

1-(7-Carboxyheptyl)-2-phenylimidazole;

1-(7-Ethoxycarbonyl)-4-phenylimidazole;

1-(7-Carboxyheptyl )-2-octylthio-4,5,-diphenylimidazole;

8-(1,4,5-Triphenylimidazol-2-yl-oxy)octanamide; and the pharmaceutically acceptable salts thereof.

Preferred compounds of the Formula (V), (VI) and the additional compounds noted above are:

1-(7-Carboxyheptyl)-2-octylthio-4,5,-diphenylimidazole;

8-[1,4,5-Triphenylimidazol-2-yl-oxy]octanoic acid;

Ethyl 5-(3,4,5-triphenyl-2-oxo-2,3-dihydroimidazol-1-yl) valerate;

Ethyl 3-(3,4,5-triphenyl-2-oxo-2,3-dihydroimidazol-1-yl) propionate;

Ethyl 6-(3,4,5-triphenyl-2-oxo-2,3-dihydroimidazol-1-yl) hexanoate;

7-(3,4,5-Triphenylimidazol-2-oxo-2,3-dihydroimidazol-1-yl)heptanonitrile;

Ethyl 6-(3-methyl-4,5-diphenyl-2-oxo-2,3-dihydroimidazol-1-yl)hexanoate;

1-(7-Ethoxycarbonyl)-4-phenylimidazole; and

Methyl-7-(3,4,5-triphenyl)-2-oxo-1,2-dihydroimidazol-1-yl)-5-heptynoate.

More preferred compounds for use herein are:

1-(7-Carboxyheptyl)-2-octylthio-4,5,-diphenylimidazole;

8-[1,4,5-Triphenylimidazol-2-yl-oxy]octanoic acid;

Ethyl 5-(3,4,5-triphenyl-2-oxo-2,3-dihydroimidazol-1-yl) valerate;

Ethyl 3-(3,4,5-triphenyl-2-oxo-2,3-dihydroimidazol-1-yl) propionate; and 7-(3,4,5,-Triphenylimidazol-2-oxo-2,3-dihydroimidazol-1-yl)heptanonitrile.

Examples 69 to 83 in the Synthetic Chemistry section serve to illustrate the preparation of compounds representative of structure (V), (VI) and the additional compounds noted above.

Methods of Treatment

Inhibition of CoA-IT and the simultaneous reduction of PAF and free arachidonic acid and eicosanoid release from inflammatory cells according to this invention is of therapeutic benefit in a broad range of diseases or disorders. The invention is useful to treat disease states both in humans and in other mammals.

This invention reveals that inhibition of CoA-IT is an effective means for simultaneously reducing PAF, free arachidonic acid and eicosanoids produced in inflammatory cells. Since PAF, free arachidonic acid and eicosanoids mediate a broad range of diseases and disorders in human and other mammals, blockage of CoA-IT will be a useful way to treat these disease states. The therapeutic utility of blocking lipid mediator generation has been recognized for many years. For example, inhibitors of cyclooxygenase, such as aspirin, indomethacin, acetaminophen and ibuprofen, have demonstrated broad therapeutic utilities. CoA-IT inhibitors inhibit cyclooxygenase products. Another class of inhibitors which are used in a broad range of inflammatory disorders are the corticosteroids. Corticosteroids induce inflammatory cells to produce proteins which inhibit free arachidonic acid release. CoA-IT inhibitors block the release of free arachidonic acid. Inhibitors of 5-lipoxygenase block the production of leukotrienes and leukotriene antagonists prevent the bioactions of leukotrienes. Recent studies indicate that both will have broad therapeutic utilities, and CoA-IT inhibitors block the production of leukotrienes. Inhibitors of phospholipase $A_2$ block the release of free arachidonic acid and the formation of lyso PAF (the immediate precursor of PAF). $PLA_2$ inhibitors are proposed to have broad therapeutic utilities. CoA-IT inhibitors block the release of free arachidonic acid and PAF generation. Taken together with the in vivo data presented in FIG. 5, inhibition of CoA-IT will have broad therapeutic utility by virtue of its capacity to block lipid mediator generation. Compounds that inhibit CoA-IT activity will thus be useful in many disease states. However, it does not follow that these disease states are in fact caused by altered CoA-IT activity. Thus, the disease may not be directly mediated by CoA-IT activity. It only follows that CoA-IT activity is required for the continued expression of symptoms of the disease state and that CoA-IT inhibitors will be beneficial against the symptoms of these disease states.

This invention reveals that inhibition of CoA-IT, an enzyme that affects arachidonate movement, blocks PAF production. This is an expected result because PAF metabolism and arachidonic acid metabolism are closely linked, in that 1-alkyl-2-arachidononyl-GPC is a major precurser for PAF [Chilton et al.,*J. Biol. Chem.* 259:12014–12019, (1984)] and arachidonate in the sn-2 position of this molecule appears to play a role in its recognition by PLA2 enzymes specific for arachidonic acid [Bonelli et al., *J. Biol. Chem.,* 264:14723–14728 (1989); Channon et al.,*J. Biol. Chem.,* 265:5409–5413 (1990); Diez et al., *J. Biol. Chem.,* 265:14654–14661 (1990)]. Arachidonate depletion in cells has further been coupled to a loss of PAF production and refeeding of arachidonate to those cells restored PAF production. These data sugest that maintenance of arachidonate containing alkyl-and alkenyl-linked phospholipid pools, a process mediated by CoA-IT, may in effect prime inflammatory cells for the coordinated production of prostaglandins, leukotrienes and PAF.

Interruption of CoA-IT activity would therefore inhibit arachidonate reincorporation into the alkyl and alkenyl-linked phospholipids pools (FIG. 1, pool 2). Further inhibition of CoA-IT could also lead to depletion of arachidonate in the alkyl and alkenyl phospholipid pools and consequently decrease both free arachidonic acid release and PAF production. Finally, CoA-IT may also be important in the initial mobilization of precursors to PAF (lysoPAF) and arachidonic acid metabolites (free arachidonic acid). Inhibitors of CoA-IT have now been shown to block the formation of these intermediates.

This invention reveals that inhibition of CoA-IT reduces PAF production and this finding has a number of therapeutic implications. PAF itself has been implicated as being involved in a number of medical conditions. Thus in circulatory shock, which is characterised by systemic hypotension, pulmonary hypertension and increased lung vascular permeability, the symptoms can be mimicked by infusion of PAF. This coupled with evidence showing that circulating PAF levels are increased by endotoxin infusion indicate that PAF is a prime mediator in certain forms of shock.

Intravenous infusion of PAF at doses of 20–200 pmol kg<–1>min<–1>into rats has been reported to result in the formation of extensive haemorrhagic erosions in the gastric mucosa. Thus PAF is the most potent gastric ulcerogen yet described whose endogenous release may underlie or contribute to certain forms of gastric ulceration. Psoriasis is an inflammatory and proliferative disease characterised by skin lesions. PAF is pro- inflammatory and has been isolated from lesioned scale of psoriatic patients indicating PAF has a role is the disease of psoriasis. And finally, increasing evidence supports a potential patho-physiological role for PAF in cardiovascular disease. Thus recent studies in angina patients show PAF is released during atrial pacing. Intracoronary injection of PAF in pigs induces a prolonged decrease in coronary flow and, in guines pig hearts, it induces regional shunting and ischaemia. In addition PAF has been shown to initiate thrombus formation in a mesenteric artery preparation, both when administered exogenously and when released endogenously. More recently PAF has been shown to play a role in brain ischaemia induced in animal models of stroke.

Thus the compounds of the invention, by virtue of their ability to antagonise CoA-IT and thus block the production of PAF, free arachidonic acid and its metabolites, are likely to be of value in the treatment of any of the above conditions.

For therapeutic use the compounds of the present invention will generally be administered in a standard pharmaceutical composition obtained by admixture with a pharmaceutical carrier selected with regard to the intended route of administration and standard pharmaceutical practice. For example, they may be administered orally in the form of tablets containing such excipients as starch or lactose, or in capsule, ovules or lozenges either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood. The choice of form for administration as well as effective dosages will vary depending, inter alia, on the condition being treated. The choice of mode of administration and dosage is within the skill of the art.

The compounds of structures (I) to (VI) and any others noted herein or their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of structure (I) or a pharmaceutically acceptable salt thereof which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule.

Each dosage unit for oral administration contains preferably from 1 to 250 mg (and for parenteral administration contains preferably from 0.1 to 25 mg) of a compound of the structure (I) or a pharmaceutically acceptable salt thereof calculated as the free base.

The pharmaceutically acceptable compounds of the invention will normally be administered to a subject in a daily dosage regimen. For an adult patient this may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of the structure (I) or a pharmaceutically acceptable salt thereof calculated as the free base, the compound being administered 1 to 4 times per day.

Disease states which could benefit from the inhibition of CoA-IT include, but are not limited to, adult respiratory distress syndrome, asthma, arthritis, reperfusion injury, endotoxic shock, inflammatory bowel disease, allergic rhinitis and various inflammatory skin disorders. Each of these disorders is mediated in some pan by lipid mediators of inflammation. Compounds which inhibit CoA-IT, by virtue of their ability to block the generation of lipid mediators of inflammation, are of value in the treatment of any of these conditions.

SYNTHETIC CHEMISTRY

Without further elaboration, it is believed that one skilled in the art can, using the preceding descriptions, utilize the present invention to its fullest extent. The following examples further illustrate the synthesis of compounds of this invention. The following examples are, therefore, to be construed as merely illustrative and not a limitation of the scope of the present invention in any way.

Temperatures are recorded in degrees centigrade unles otherwise noted.

EXAMPLE 1

Sodium 7-(3,4,5-triphenyl-2-oxo-2,3-dihydroimidazol-1-yl)-heptane-sulphonate

A mixture of 1,4,5-triphenylimidazol-2-one (15.3 g), dibromoheptane (50.6 g) and potassium carbonate (13.8 g) was heated at reflux temperature in dry butanone (750 ml) for 20 hours. The mixture was cooled, filtered and the filtrate evaporated to an oil which was chromatographed on silica gel (hexane/ethyl acetate) to give 1,4,5-triphenyl-3-(7-bromoheptyl)imidazole-2-one (11.1 g, 46%) as an oil.

NMR $\delta(CDCl_3)$ 1.2–1.9 (10H, m, 5×$CH_2$), 3.4 (2H, t, —$CH_2Br$), 3.7 (2H, t, —$CH_2N$), 6.8–7.4 (15H, m, 3×Ph) ppm.

A solution of 1,4,5-triphenyl-3-(7-bromoheptyl)imidazol-2-one (2.0 g) in ethanol (10 ml) was refluxed with a solution of sodium sulphite (0.55 g) in water (5 ml) for 20 hours. More sodium sulphite (0.2 g) was added and refluxing continued for a further 20 hours. The mixture was evaporated to dryness, boiled in ethanol, filtered hot and evaporated to an oil. This was taken up in a small volume of ethanol, excess diethyl ether added and the precipitated solid filtered off and chromatographed on silica gel (dichloromethane/methanol 5:1). The resulting oil in methanol/water 1:1 was passed down an Amberlyst 15 ion exchange resin (Na form) and evaporated to a solid. This was taken up in ethanol and precipitated with diethyl ether giving sodium 7-(3,4,5-triphenyl-2-oxo-2,3-dihydroimidazol-1-yl) heptane-sulphonate (0.49 g), 23%) as a white solid, m.p. 160° C.

Found: C, 63.47; H, 5.69; N, 5.04; S, 5.63%; $C_{28}H_{29}N_2NaO_4S$+3.5% water; Requires: C, 63.31; H, 5.89; N, 5.28; S, 6.04%

EXAMPLE 2

7-(3,4,5-Triphenyl-2-oxo-2,3-dihydroimidazol-1-yl)-heptanephosphonic acid

Diethyl 7-(3,4,5-triphenyl-2-oxo-2,3-dihydroimidazol-1-yl)heptane-phosphonate (0.58 g) was dissolved in dry chloroform, cooled to −40° C. and to it was added trimethylsilyl iodide (1.05 g) over 2 mins under an atmosphere of nitrogen. The cooling bath was removed and the reaction mixture was stirred for 2.5 hours at room temperature then evaporated to an oil and re-evaporated from methanol, treated with excess aqueous sodium bicarbonate, evaporated to an oil and re-evaporated from methanol, water adn ethanol respectively. The oil was taken up in ethanol, treated with excess aqueous sodium bicarbonate, evaporated to dryness then taken up in ethanol, filtered and the filtrate evaporated to an oil which solidified under ether. The solid was dissolved in water and passed down a Dowex 1×2-200 ion exchange resin in the formate form.

Elution with aqueous formic acid gave on evaporation of the solvent 7-(3,4,5-triphenyl-2-oxo-2,3-dihydroimidazol-1-yl)heptane-phosphonic acid (0.078 g, 15%) as a light brown foam.

Found: C, 66.50; H, 6.08; N, 5.39%; $C_{28}H_{31}N_2O_4P$+3% water Requires: C, 66.50; H, 6.52; N, 5.54%

EXAMPLE 3

Diethyl 7-(3,4,5-triphenyl-2-oxo-2,3-dihydroimidazol-1-yl)heptane-phosphonate

A solution of 1,4,5-triphenyl-3-(7-bromoheptyl)imidazol-2-one (1.0 g) and triethylphosphite (1.66 g) in xylene (5 ml) was heated at reflux temperature for 40 hours. The solution was evaporated to an oil and chromatographed on silica gel (ethyl acetate/ethanol).

The resulting oil was taken up in diethyl ether, filtered and evaporated to give diethyl 7-(3,4,5-triphenyl-2-oxo-2,3-dihydroimidazol-1-yl)heptanephosphonate as a clear oil (0.84 g, 75%).

Found: C, 70.11; H, 7.37; N, 4.94%; $C_{32}H_{39}N_2O_4P$; Requires: C, 70.31; H, 7.19; N, 5.12%

EXAMPLE 4

Ethyl 7-(3,4,5-triphenyl-2-oxo-2,3-dihydroimidazol-1-yl)methyl-phosphinate

A solution of 1,4,5-triphenyl-3-(7-bromoheptyl)-imidazol-2-one (2.0 g) and diethyl methylphosphonite (2.17 g) in toluene (15 ml) was heated at reflux temperature for 48 hours with the addition of more diethyl methyl-phosphonite (0.5 g) after 24 hours. Water (5 ml) was added and the solution was evaporated to an oil which was chromatographed on silica gel (ethyl acetate/ethanol). The resulting oil was taken up in diethyl ether, filtered and evaporated to give ethyl 7-(3,4,5-triphenyl-2-oxo-2,3-dihydroimidazol-1-yl)methyl-phosphinate (1.34 g), 65%) as a clear oil.

Found: C, 70.70; H, 7.53; N, 5.35%; $C_{31}H_{37}N_2O_3P$+0.9% $Et_2O$+2% $H_2O$; Requires: C, 70.56; H, 7.36; N, 5.26%.

EXAMPLE 5

Diisopropyl-7-(3,4,5-triphenyl-2-oxo-2,3-dihydroimidazol-1-yl)heptane phosphonate A solution of 1,4,5-triphenyl-3-(7-bromoheptyl)-imidazol-2-one (1.47 g) and triisopropyl phosphite (3.12 g) in xylene (15 ml) was heated at reflux temperature for 48 hours. The solution was evaporated to an oil and chromatographed on silica gel (ethyl acetate/ethanol). The resulting oil was taken up in diethyl ether, filtered and evaporated to the titled compound as a clear oil (0.33 g; 19%) Found: C, 70.02; H, 7.53; N, 5.19%; $C_{34}H_{43}N_2O_4P$+1.5% $H_2O$; Requires: C, 69.99; H, 7.60; N, 4.80%.

EXAMPLE 6

Dimethyl-7-(3,4,5-triphenyl-2-oxo-2,3-dihydroimidazol-1-yl)heptane phosphonate

A solution of 1,4,5-triphenyl-3-(7-bromoheptyl)-imidazol-2-one (1.47 g) and trimethyl phosphite (1.89 g) in xylene (10 ml) was heated at reflux temperature for 6 days. The solution was evaporated to an oil and chromatographed on silica gel (ethyl acetate/ethanol). The resulting oil was taken up in diethyl ether, filtered and evaporated to the titled compound as a clear oil (0.30 g; 19%)

NMR $\delta$(CDCl$_3$) 1.2–1.9 (10H, m, 5×CH$_2$), 3.6–3.8 (8H, m, —CH$_2$N+2×—OCH$_3$), 6.8–7.4 (15H, m, 3×Ph) ppm.

EXAMPLE 7

Diethyl-6-(3,4,5-triphenyl-2-oxo-2,3-dihydroimidazol-1-yl)hexane phosphonate

A solution of 1,4,5-triphenyl-3-(6-bromoheptyl)-imidazol-2-one (1.43 g) and triethyl phosphite (2.49 g) in xylene (8 ml) was heated at reflux temperature for 65 hours. The solution was evaporated to an oil and chromatographed on silica gel (ethyl acetate/ethanol). The resulting oil was taken up in diethyl ether, filtered and evaporated to the titled compound as a clear oil (1.15 g; 72%) Found: C, 69.67; H, 7.13; N, 5.43%; C$_{31}$H$_{37}$N$_2$O$_4$P; Requires: C, 69.91; H, 7.00; N, 5.26%.

EXAMPLE 8

Diethyl-8-(3,4,5-triphenyl-2-oxo-2,3-dihydroimidazol-1-yl)octane phosphonate

A solution of 1,4,5-triphenyl-3-(8-bromoheptyl)-imidazol-2-one (1.52 g) and triethyl phosphite (2.49 g) in xylene (10 ml) was heated at reflux temperature for 65 hours. The solution was evaporated to an oil and chromatographed on silica gel (ethyl acetate/ethanol). The resulting oil was taken up in diethyl ether, filtered and evaporated to the titled compound as a clear oil (1.28 g; 76%) Found: C, 70.15; H, 7.41; N, 5.06%; C$_{33}$H$_{41}$N$_2$O$_4$P+1% H$_2$O; Requires: C, 69.99; H, 7.41; N, 4.85%.

EXAMPLE 9

1-(7-ethoxycarbonylheptyl)-2,4,5-triphenylimidazole

A mixture of 2,4,5-triphenylimidazole (11 g), ethyl 8-bromooctanoate (18.64 g), anhydrous potassium carbonate (51.3 g) and dry butanone (350 ml) was heated at reflux for 26 h. The cooled reaction mixture was filtered to remove inorganics and the filtrate was evaporated to dryness in vacuo. The residue was stirred in hexane and unreacted 2,4,5-triphenylimidazole was collected by filtration (3.1 g). The filtrate was cooled and a white precipitate was collected. Recrystallisation from hexane gave 1-(7-ethoxy-carbonyl-heptyl)-2,4,5-triphenylimidazole (8.37 g, 48.4%) as a white solid, m.p. 65°–7°.

Found C, 79.97; H, 7.32; N, 6.39%; C$_{31}$H$_{34}$N$_2$O$_2$ requires: C, 79.79; H, 7.34; N, 6.00%.

EXAMPLE 10

1-(7-carboxyheptyl)-2,4,5-triphenylimidazole

A mixture of 1-(7-ethoxycarbonylheptyl)-2,4,5-triphenylimidazole (13.6 g), 2N aqueous sodium hydroxide (300 ml) and ethanol (200 ml) was heated at reflux for 2.5 h. The ethanol was removed in vacuo and the reaction mixture was acidified with 2N aqueous hydrochloric acid. The aqueous solution was extracted with ethyl acetate (4×200 ml) and the organic extracts were combined, dried over anhydrous magnesium sulphate and evaporated to dryness in vacuo. Recrystallisation from ethanol gave 1-(7-carboxyheptyl)-2,4,5-triphenylimidazole (9.77 g, 76.4%) as a white solid, m.p. 162°; Found C, 79.43; H, 6.93; N, 6.36%; C$_{29}$H$_{30}$N$_2$O$_2$ requires: C, 79.42; H, 6.90; N, 6.39%.

EXAMPLE 11

1-(7-methoxycarbonylheptyl)-2,4,5-triphenylimidazole

A mixture of 1-(7-carboxyheptyl)-2,4,5-triphenylimidazole (0.5 g), concentrated sulphuric acid (2 ml) and methanol (100 ml) was heated at reflux for 24 h. The solvent was removed in vacuo and the residue was dissolved in ethyl acetate (50 ml), washed with water (50 ml), saturated NaHCO$_3$ solution (50 ml), water (50 ml), dried over anhydrous magnesium sulphate and evaporated to dryness in vacuo. Column chromatography on silica gel eluted with a dichloromethane:methanol gradient gave 1-(7-methoxycarbonylheptyl)-2,4,5-triphenylimidazole (0.28 g, 54%) as an oil.

Found: C, 79.74; H, 7.55; N, 5.99%; C$_{30}$H$_{42}$N$_2$O$_2$ requires: C, 79.61; H, 7.13; N, 6.19%.

EXAMPLE 12

1-(6-ethoxy-carbonylhexyl)-2,4,5-triphenylimidazole 2,4,5-Triphenylimidazole (1.3 g) was added to a suspension of sodium hydride (0.23 g) (50% dispersion in oil, washed with hexane) in dry dimethylformamide (40 ml) under nitrogen. The reaction was stirred at 45° C. for 1.5 h, cooled and ethyl 7-bromoheptanoate (1.1 g) in dry dimethylformamide (10 ml) was added. The reaction was stirred at 50° C. for 5 h, cooled and water was carefully added. The solvent was removed in vacuo and the residue was dissolved in ethyl acetate (100 ml). The organic solution was washed with saturated sodium chloride solution (150 ml), water (100 ml), dried over anhydrous magnesium sulphate and evaporated to dryness in vacuo. The residue was chromatographed on silica gel eluted with a dichloro-methane:ethanol gradient to give 1-(6-ethoxy-carbonylhexyl)-2,4,5-triphenylimidazole (0.81 g, 41%) as an oil. Found: C, 79.74; H, 7.32; N, 6.12%; C$_{30}$H$_{32}$N$_2$O$_2$ requires: C, 79.61; H, 7.13; N, 6.19%.

EXAMPLE 13

1-(6-carboxyhexyl)-2,4,5-triphenylimidazole

Reaction of 1-(6-ethoxycarbonylhexyl)-2,4,5-triphenylimidazole (0.4 g) with sodium hydroxide in a method similar to Example 10 gave, after recrystallisations from ethanol and isopropanol, 1-(6-carboxyhexyl)-2,4,5-triphenylimidazole (0.19 g, 51%) as a white solid, m.p. 149°–150°; Found: C, 79.34; H, 6.65; N, 6.48%; C$_{28}$H$_{28}$N$_2$O$_2$ requires: C, 79.22; H, 6.65; N, 6.60%.

EXAMPLE 14

1-[6-(5-tetrazolyhexyl)-2,4,5-triphenylimidazole a) A mixture of 2,4,5-triphenylimidazole (52.5 g), dibromohexane (174 g) and potassium carbonate (48.4 g) in dry butanone (400 ml) were heated at reflux temperature for 20 hours. The mixture was filtered and the filtrate evaporated to an oil. Approximately half of the excess dibromohexane was removed by distillation and the remaining oil was chromatographed on silica gel (hexane/ethyl acetate) giving, after recrystallisation from ethyl acetate, 1-(6-bromohexyl)-2,4,5-triphenyl-imidazole (35.0 g, 43%) as a colourless solid, m.p. 106°–7°; NMR d (CDCl$_3$) 0.9–1.7 (8H, m, 4×CH$_2$), 3.2 (2H, t, CH$_2$Br), 3.9 (2H, t, CH$_2$N), 7.1–7.7 (15H, m, 3×Ph) ppm.

b) 1-(6-Bromohexyl)-2,4,5-triphenylimidazole (27.6 g) in dry dimethylsulphoxide (70 ml) was added over 10 minutes to a mixture of sodium cyanide (3.68 g) in dimethylsulphoxide (50 ml) and the reaction was stirred at room temperature for 20 h. The reaction mixture was poured into water (300 ml) and extracted with dichloromethane (3×150 ml). The extracts were combined, washed with water, dried over anhydrous magnesium sulphate and evaporated to dryness in vacuo. Recrystallisation from diethyl ether and hexane gave 1-(6-cyanohexyl)-2,4,5-triphenylimidazole (24.19 g, 99%) as a white solid, m.p. 104°–6°.

NMR d (CDCl$_3$) 0.8–1.1 (4H, m, 2×CH$_2$), 1.1–1.4 (4H, m, 2×CH$_2$), 2.1 (2H, t, CH$_2$CN), 3.90 (2H, t, NCH$_2$),7.0–7.8 (15H, m, 3×Ph) ppm c) A mixture of 1-(6-cyanohexyl)-2,4,5-triphenyl-imidazole (2 g), tri-n-butyl tin azide (5 g) (Kricheldorf, H, Leppert, E, Synthesis, (1976) 329) and dry tetrahydrofuran (10 ml), under nitrogen, was heated at reflux for 20 h. Tri-n-butyl tin azide (5 g) in dry tetrahydrofuran (10 ml) was added and the reaction was heated at reflux for 24 h. The cooled reaction mixture was poured into 2N aqueous hydrochloric acid (100 ml) and water (100 ml) was added. The aqueous mixture was extracted with dichloromethane (2×50 ml). The organic extracts were combined, washed with saturated sodium chloride solution (50 ml) dried over anhydrous magnesium sulphate and evaporated to dryness in vacuo. Chromatography on silica gel eluted with a dichloromethane:methanol gradient and recrystallisation from ethanol/water gave 1-[6-(5-tetrazolyhexyl)-2,4,5-triphenylimidazole (0.25 g, 11.4%) as a white solid, m.p. 196°–7°; Found: C, 75.07; H, 6.40; N, 18.61%; C$_{28}$H$_{28}$N$_6$ requires: C, 74.97; H, 6.29; N, 18.74%.

EXAMPLE 15

1-(8-carboxyoctyl)-2,4,5-triphenylimidazole a) 2,4,5-Triphenylimidazole (5 g) was added to a suspension of sodium hydride (1.0 g) (50% dispersion in oil, washed with hexane) in dry dimethylformamide (80 ml) under nitrogen. The reaction was stirred at 45° C. for 1 h, cooled and added, over 1 h to a solution of 1,8-dibromooctane (30 g) in dry dimethylformamide (100 ml) under nitrogen. The reaction was stirred at room temperature for 24 h, water was carefully added and the solvent was removed in vacuo. The residue was dissolved in ethyl acetate (500 ml), washed with water (250 ml), 2N aqueous hydrochloric acid (250 ml), saturated sodium chloride solution (250 ml), dried over anhydrous magnesium sulphate and evaporated to dryness in vacuo. Distillation to remove 1,8-dibromooctane and chromatography on silica gel eluted with dichloromethane gave 1-(8-bromooctyl)-2,4,5-triphenylimidazole (4.1 g, 50%) as an oil; NMR d (CDCl$_3$) 0.9–1.7 (12H, m, 6×CH$_2$), 3.3 (2H, t, BrCH$_2$), 3.9 (2H, t, N—CH$_2$), 7.1–7.7(15H, m, 3×Ph) ppm.

b) 1-(8-Bromooctyl)-2,4,5-triphenylimidazole (4 g) in dimethylsulphoxide (30 ml) was added dropwise to a mixture of sodium cyanide (0.5 g) in dry dimethylsulphoxide (30 ml). The reaction mixture was stirred at 50° C. for 2 h, cooled and poured into water (400 ml). The aqueous was extracted with diethyl ether (4×100 ml), the extracts were combined, washed with water (100 ml), dried over anhydrous magnesium sulphate and evaporated to dryness in vacuo. Chromatography on silica gel eluted with a dichloromethane:methanol gradient and recrystallisation from ether gave 1-(8-cyanooctyl)-2,4,5-triphenylimidazole (1.1 g, 31%) as a white solid, m.p. 72°–73°. Found: C, 83.10; H, 7.21; N, 9.69%; C$_{30}$H$_{31}$N$_3$ requires: C, 82.90; H, 7.19; N, 9.57%.

c) A mixture of 1-(8-cyanooctyl)-2,4,5-triphenyl-imidazole (0.8 g), concentrated sulphuric acid (10 ml) and water (10 ml) was stirred at reflux for 4 h. Water (50 ml) was added to the cooled mixture and the mixture was extracted with ethyl acetate (2×25 ml). The organic extracts were combined, washed with water (25 ml), dried over anhydrous magnesium sulphate and evaporated to dryness in vacuo. Recrystallisation from ethanol/water gave 1-(8-carboxyoctyl)-2,4,5-triphenylimidazole (0.22 g, 26%) as a cream solid, m.p. 149°–150° C.; Found C: 79.32; H, 7.17; N, 5.95%; C$_{30}$H$_{32}$N$_2$ requires: C, 79.61; H, 7.13; N, 6.19%.

EXAMPLE 16

1-(10-carboxydecyl)-2,4,5-triphenylimidazole (a) 2,4,5-Triphenylimidazole (2.5 g) and ethyl 11-bromoundecanoate (4.94 g) were reacted in a method similar to Example 9. Work-up and column chromatography on silica gel eluted with 30:1 dichloromethane:ethanol gave 1-(10-ethoxy-carbonyldecyl)-2,4,5-triphenylimidazole (1.95 g, 45%) as an oil.

(b) 1-(10-Ethoxycarbonyldecyl)-2,4,5-triphenylimidazole (1.3 g) was reacted with 2N sodium hydroxide in a method similar to Example 10 to give, after column chromatography on silica gel eluted with a dichloro-methane:methanol gradient and recrystallisation from ethyl acetate/hexane, 1-(10-carboxydecyl)-2,4,5-triphenylimidazole (0.25 g, 19.2%) as a cream solid, m.p. 76°–78°; Found: C, 79.68%; H, 7.56%; N, 5.78%; C$_{32}$H$_{36}$N$_2$O$_2$ requires: C, 79.96%; H, 7.55; N, 5.83%.

EXAMPLE 17

1-(7-carboxyheptyl)-2-methyl-4,5-diphenylimidazole a) 2-Methyl-4,5-diphenylimidazole (2.5 g) (J. Org. Chem., 1937, 2, 328) was reacted with sodium hydride (0.62 g) and ethyl 8-bromooctanoate (3.36 g) in a method similar to Example 12. Chromatography on silica gel eluted with a dichloromethane:ethanol gradient gave 1-(7-ethoxycarbonyl-heptyl)-2-methyl-4,5-diphenylimidazole (3.1 g, 72.1%) as an oil.

NMR d (CDCl$_3$) 1.15 (6H, m, 3×CH$_2$), 1.25 (3H, t, CH$_2$CH$_3$), 1.50 (4H, m, NCH$_2$CH$_2$, O=CCH$_2$CH$_2$), 2.23 (2H, t, CH$_2$CO$_2$), 2.50 (3H, s, CH$_3$), 3.69 (2H, t, NCH$_2$), 4.10 (2H, q, O=C—OCH$_2$), 7.10–7.50 (10H, m, 2×Ph) ppm 1-(7-Ethoxycarbonylheptyl)-2-methyl-4,5-diphenyl-imidazole b) 1-(7-Ethoxycarbonylheptyl)-2-methyl-4,5-diphenyl-imidazole (3.0 g) was reacted with 2N sodium hydroxide in a method similar to Example 10 to give, after recrystallisation from acetonitrile, 1-(7-carboxyheptyl)-2-methyl-4,5-diphenylimidazole (1.19 g, 42.5%) as white needles, m.p. 135°–6°; Found: C, 75.37; H, 7.39; N, 7.27%; C$_{24}$H$_{28}$N$_2$O$_2$1.9% H$_2$O requires: C, 75.14; H, 7.57; N, 7.30%.

EXAMPLE 18

1-(7-ethoxycarbonylheptyl)-2-methyl-4,5-diphenyl-imidazole

A mixture of 1-(7-carboxyheptyl)-2-methyl-4,5-diphenyl-imidazole (0.5 g), concentrated sulphuric acid (0.5 ml) and absolute alcohol (50 ml) was heated at reflux for 3 h. The solvent was removed in vacuo, the residue dissolved in ethyl acetate (50 ml), washed with water (25 ml), dried over anhydrous magnesium sulphate and evaporated to dryness in vacuo. Column chromatography on silica gel eluted with a dichloro-methane:ethanol gradient gave 1-(7-ethoxycarbonylheptyl)-2-methyl-4,5-diphenyl-imidazole (0.22 g, 41%) as an oil.

Found: C, 75.70; H, 7.88; N, 7.01%; $C_{26}H_{32}N_2O_2$ 1.7 $H_2O$ requires: C, 75.90; H, 8.03; N, 6.89%.

EXAMPLE 19

1-(7-(5-tetrazolylheptyl)-2,4,5-triphenylimidazole a) A mixture of 2,4,5-triphenylimidazole (11.5 g), 1,7-dibromo-heptane (50 g) and potassium carbonate (27 g) in dry butanone (250 ml) was heated at reflux for 20 hours. The mixture was filtered and the filtrate evaporated to an oil. Chromatography on silica gel (hexane/ethyl acetate) and recrystallisation from hexane gave 1-(7-bromoheptyl)-2,4,5-triphenylimidazole (11.3 g, 61.4%) as a colourless solid, m.p. 69°–71°.

Found: C, 71.18; H, 6.22; N, 5.99; Br, 16.95%; $C_{28}H_{29}BrN2$ requires: C, 71.03; H, 6.17; N, 5.92; Br, 16.88%;

b) 1-(7-Bromoheptyl)-2,4,5-triphenylimidazole (7 g) in dry dimethylsulphoxide (15 ml) was added over 20 minutes to a mixture of sodium cyanide (0.87 g) in dimethyl-sulphoxide (25 ml). The reaction was stirred at 40° C. for 1 hour. The cooled reaction mixture was poured into water (800 ml) and extracted with diethyl ether (4×100 ml). The extracts were combined, washed with water, dried over anhydrous magnesium sulphate and evaporated to dryness in vacuo. Recrystallisation from dichloro-methane/hexane gave 1-(7-cyanoheptyl)-2,4,5-triphenylimidazole (3.7 g,60%) as a white solid, m.p. 93°–94°; Found: C, 82.35; H, 6.90; N, 9.96%; $C_{29}H_{29}N_3$ 1% $CH_2Cl_2$ requires C, 82.43; H, 6.91; N, 9.91%.

c) A mixture of 1-(7-cyanoheptyl)-2,4,5-triphenyl-imidazole (2 g), tri-n-butyl tin azide (5 g) and dry tetrahydrofuran (30 ml), under nitrogen, was heated at reflux for 8 hours. Tri-n-butyl tin azide (4.9 g) in dry tetrahydrofuran (5 ml) was added and the reaction was heated at reflux for 48 hours. The cooled reaction mixture was poured into 2N hydrochloric acid (100 ml) and water (100 ml) was added. The aqueous mixture was extracted with dichloromethane (2×50 ml). The organic extracts were combined, washed with saturated sodium chloride solution (50 ml), dried over anhydrous magnesium sulphate and evaporated to dryness in vacuo. Chromatography on silica gel (dichloromethane/methanol) gave 1-(7-(5-tetrazolylheptyl)-2,4,5-triphenylimidazole (0.2 g, 9%) as a foam.

Found: C, 74.08; H, 6.63; N, 17.30%; $C_{29}H_{30}N_6$ 0.5% W/N $C_2H_5OH$ requires C, 74.14; H, 6.87; N, 17.26%.

EXAMPLE 20

2-(2-methoxyethoxy)ethyl 8-(2,4,5-triphenylimidazol-1-yl)octanoate a) 8-Bromooctanoic acid (22.3 g), 2-(2-methoxyethoxy)-ethanol (14.08 g) and p-toluenesulphonic acid (0.1 g) were added to toluene (250 ml) and the resulting solution heated at reflux temperature for 16 hours. Ethyl acetate (500 ml) was then added and the solution washed with aqueous $K_2CO_3$ solution and water, dried and evaporated. The residual oil was distilled to give 2-(2-methoxyethoxy)-ethyl 8-bromooctanoate (25.5 g), 77%) as a colourless oil, b.p. 126°–128° C./0.08 mm Hg.

b) The above alkyl bromide (7.5 g) and 2,4,5-triphenyl-imidazole (4.44 g) were treated with $K_2CO_3$ (3.1 g) in refluxing 2-butanone (60 ml) for 18 hours. The solvent was evaporated and the resulting solid chromatographed on silica gel to give 2-(2-methoxyethoxy)-ethyl 8-(2,4,5-triphenylimidazol-1-yl)octanoate (1.5 g, 42%) as a colourless oil. Found: C, 75.13; H, 7.47; N, 5–18%; $C_{34}H_{40}N_2O_4$ requires: C, 75.53; H, 7.46; N, 5.18%

EXAMPLE 21

Ethyl 8-(4,5-diphenylimidazol-1-yl)octanoate 4,5-Triphenylimidazole (5.5 g) was treated with ethyl 8-bromooctanoate (12.55 g) by the method described in example 5 to give, after work-up and chromatography, ethyl 8-(4,5-diphenylimidazol-1-yl)octanoate (7.8 g, 80%) as a pale yellow oil. Found: C, 76.67; H, 7.85; N, 7.07%; $C_{25}H_{30}N_2O_2$ requires: C, 76.89; H, 7.74; N, 7.17%

EXAMPLE 22

8-(4,5-diphenyl-imidazol-1-yl)octanoic acid

Ethyl 8-(4,5-diphenylimidazole-1-yl)octanate. (3.25 g) was treated with sodium hydroxide as described in example 10 to give 8-(4,5-diphenyl-imidazol-1-yl)octanoic acid (0.6 g, 20%) as colourless needles, m.p. 129.5°–130° C.

Found: C, 75.75; H, 7.20; N, 7.53% $C_{23}H_{26}N_2O_2$ 0.1 HCl requires: C, 75.45; H, 7.18; N, 7.65%

EXAMPLE 23

2-(2-methoxyethoxy)ethyl 8-(4,5-diphenylimidazole-1-yl)-octanoate 4,5-Diphenylimidazole (2.85 g) was treated with 2-(2-methoxy-ethoxy)ethyl 8-bromooctanoate (8.63 g) as described in Example 20 to give 2-(2-methoxyethoxy)ethyl 8-(4,5-diphenylimidazole-1-yl)octanoate as a colourless oil (1.5 g, 25%). Found: C, 72.28; H, 7.91; N, 6.35% $C_{28}H_{36}N_2O_4$ requires: C, 72.38; H, 7.81; N, 6.03%

EXAMPLE 24

1-(7-carboxyheptyl)-2-(4-methoxyphenyl)-4,5-diphenyl-imidazole a) 2-(4-Methoxyphenyl)-4,5-diphenylimidazole (10 g) (J. Org. Chem., 1964, 29, 1926–30) was reacted with sodium hydride (1.7 g) and ethyl 8-bromooctanoate (9.6 g) in a method similar to Example 12. Chromatography on silica gel eluted with chloroform gave 1-(7-ethoxy-carbonylheptyl)2-(4-methoxyphenyl)-4,5-diphenylimidazole (12.9 g, 85%) as an oil.

b) 1-(7-Ethoxycarbonylheptyl)-2-(4-methoxyphenyl)-4,5-diphenyl-imidazole (5 g) was treated as in Example 10. Work-up and recrystallisation from ethanol gave 1-(7-carboxyheptyl)-2-(4-methoxy-phenyl)-4,5-diphenyl-imidazole (3.51 g, 75%) as a white solid, m.p 173°–4°.

Found: C, 76.23; H, 6.89; N, 5.71%; $C_{30}H_{32}N_2O_3$+1% w/w $C_2H_5OH$ requires: C, 76.64; H, 6.94; N, 5.92%;

EXAMPLE 25

1-(7-ethoxy-carbonylheptyl)-2-(4-methoxyphenyl)-4,5-diphenylimidazole 1-(7-Carboxyheptyl)-2-(4-methoxyphenyl)-4,5-diphenyl-imidazole (0.4 g) was reacted with ethanol and concentrated sulphuric acid in a method similar to Example 18 to give, after work-up and column chromatography on silica gel eluted with a dichloromethane:ethanol gradient, 1-(7-ethoxy-carbonylheptyl)-2-(4-methoxyphenyl)-4,5-diphenylimidazole (0.21 g, 50%) as an oil. Found: C, 77.39; H, 7.55; N, 5.96%; $C_{32}H_{36}N_2O_3$ requires: C, 77.39; H, 7.31; N, 5.64%.

EXAMPLE 26

1-(7-carboxy-heptyl)-2-(4-hydroxyphenyl)-4,5-diphenyl-imidazole 1-(7-Carboxyheptyl)-2-(4-methoxyphenyl)-4,5-diphenyl-imidazole (2.5 g) was added, in portions over 40 minutes, to a solution of boron tribromide (2.17 ml) in anhydrous dichloromethane (40 ml). The reaction was stirred at room temperature for 5 h, cooled and water (50 ml) was carefully added. The organic layer was removed and the aqueous layer was washed with dichloromethane (3×75 ml). The organic extracts were combined, dried over anhydrous magnesium sulphate and evaporated to dryness in vacuo. Column chromatography on silica gel eluted with a dichloro-methane:methanol gradient and recrystallisation from ethanol/water and acetonitrile gave 1-(7-carboxy-heptyl)-2-(4-hydroxyphenyl)-4,5-diphenyl-imidazole (0.49 g, 20%) as a white solid, m.p. 171°–172°. Further material was obtained from the mother liquors (0.79 g, 33%) m.p. 167°. Found C: 76.85; H, 6.65; N, 6.20%; $C_{29}H_{30}N_2O_3$ requires: C, 76.63; H, 6.65; N, 6.16%;

EXAMPLE 27

1-(7-carboxy-heptyl)-2-(4-hydroxy-3,5-diiodophenyl)-4,5-diphenyl-imidazole

A solution of iodine (0.25 g) and potassium iodide (0.48 g) in water (1 ml) was added to a mixture of 1-(7-carboxyheptyl)-2-(4-hydroxyphenyl)-4,5,-diphenyl-imidazole (0.2 g) in 25% aqueous methylamine (1.5 ml), cooled in an ice-bath. The reaction mixture was stirred at room temperature for 2 h, aqueous sodium metabisulphite solution was added and stirring was continued for 0.5 h. The reaction mixture was acidified to pH 3 with glacial acetic acid. The resulting orange solid was collected and washed with aqueous sodium metabisulphite solution. Recrystallisation from ethanol/water gave 1-(7-carboxy-heptyl)-2-(4-hydroxy-3,5-diiodophenyl)-4,5-diphenyl-imidazole (0.14 g, 45%) as an off-white solid, m.p. 186°. Found: C, 49.49; H, 3.99; N, 4.36; I, 35.64%; $C_{29}H_{28}I_2N_2O_3$ requires: C, 49.31; H, 4.00; N, 3.97; I, 35.93%.

EXAMPLE 28

2-benzyl-1-(7-ethoxycarbonylheptyl)-4,5-diphenylimidazole

2-Benzyl-4,5-diphenylimidazole (3.3 g) (Weiss, M, J. Am. Chem. Soc., 1952, 74, 5193–5) was reacted with ethyl 8-bromooctanoate as in Example 9. Column chromatography on silica gel eluted with a dichloro-methane:ethanol gradient followed by distillation at 200° C./0.1 torr to remove volatile impurities gave a yellow oil. Recrystallisation from hexane gave 2-benzyl-1-(7-ethoxycarbonylheptyl)-4,5-diphenylimidazole (2.69 g, 52.6%) as a white solid, m.p. 82°–3°. Found: C, 80.35; H, 7.58; N, 6.08%; $C_{32}H_{36}N_2O_2$ requires: C, 79.96; H, 7.55; N. 5.83%.

EXAMPLE 29

2-benzyl-1-(7-carboxyheptyl)-4,5-diphenylimidazole

2-Benzyl-1-(7-ethoxycarbonylheptyl)-4,5-diphenyl-midazole (1.5 g) was treated in a method similar to Example 10. Ethanol was removed in vacuo and the aqueous solution was acidified with 2N aqueous hydrochloric acid and extracted with dichloromethane (2×75 ml). The extracts were combined, dried over anhydrous magnesium sulphate and evaporated to dryness in vacuo. Recrystallisation from ethanol gave 2-benzyl-1-(7-carboxy-heptyl)-4,5-diphenylimidazole (1.14 g, 81%) as a white solid, m.p. 148°–9°. Found: C, 79.56; H, 7.13; N, 6.04%; $C_{30}H_{32}N_2O_2$ requires: C, 79.61; H, 7.13; N, 6.19%.

EXAMPLE 30

1-(7-carboxyheptyl)-2-[4-octyloxy-phenyl]-4,5-diphenylimidazole a) 2-(4-Hydroxyphenyl)-4,5-diphenylimidazole (5 g) (J. Org. Chem., 1964, 29, 1926) was reacted with 8-bromooctane (6.2 g) in a method similar to Example 9. Work-up and recrystallisation from ethanol and water gave 2-(4-octyloxyphenyl)-4,5-diphenylimidazole (4.29 g, 63%) as a white solid, m.p. 178°. Found: C, 82.31; H, 7.66; N, 6.73%; $C_{29}H_{32}N_2O$ requires C, 82.04; H, 7.60; N, 6.60%.

b) 2-(4-Octyloxyphenyl)-4,5-diphenylimidazole (2.5 g) was reacted with ethyl 8-bromooctanoate (2.96 g) in a method similar to Example 9. Column chromatography on silica gel eluted with a hexane:ethyl acetate gradient gave 1-(7-ethoxycarbonylheptyl)-2-[4-octyloxyphenyl]-4,5-diphenylimidazole (3.48 g, 94%) as an oil.

NMR d (CDCl$_3$); 0.8–1.5 (23H, m, 10×CH2, CH3), 1.8 (2H, q, OCH2CH2), 2.2 (2H, t, $CH_2$(C=O), 3.85 (2H, t, NCH$_2$), 4.05 (4H, m, $CH_2$OC=O, COCH2), 6.95–7.6 (14H, m, ArH) ppm.

c) 1-(7-Ethoxycarbonylheptyl)-2-[4-octyloxyphenyl]-4,5-diphenylimidazole (3.2 g) was reacted with 2N sodium hydroxide in a method similar to Example 9. Column chromatography on silica gel eluted with a dichloro-methane:methanol gradient and recrystallisation from acetonitrile gave 1-(7-carboxyheptyl)-2-[4-octyloxy-phenyl]-4,5-diphenylimidazole (1.7 g, 58.6%) as a white solid, m.p. 114°–115°. Found: C, 78.61; H, 8.23; N, 4.96%; $C_{37}H_{46}N_2O_3$ requires: C, 78.41; H, 8.18; N, 4.94%.

EXAMPLE 31

1-(7-carboxyheptyl)-2 octylthio-4,5-diphenyl-imidazole a) A mixture of 4,5-diphenyl-2-imidazolethiol (2.5 g), 8-bromooctane (3.8 g), anhydrous potassium carbonate (13.7 g) and dry butanone (60 ml) was stirred at reflux for 2 h. The cooled reaction mixture was filtered to remove solid and the filtrate was evaporated to dryness. The residue was mixed with hexane and the resulting precipitate was collected by filtration. Recrystallisation from ethanol and water gave 2-octylthio-4,5-diphenylimidazole (1.9 g, 53%) as a white solid, m.p. 133°–4°.

Found: C, 76.15; H, 7.82; N, 7.74, S, 9.23%; $C_{23}H_{28}N_2S$ requires: C, 75.78; H, 7.74; N, 7.68; S, 8.80%.

b) 2-Octylthio-4,5-diphenylimidazole (1.7 g) was reacted with ethyl 8-bromoctanoate in a method similar to Example 9 to give, after chromatography on silica gel eluted with a hexane:dichloromethane gradient, 1-(7-ethoxycarbonyl-heptyl)-2-octylthio-4,5 -diphenylimidazole (2.19 g, 87.6%) as an oil. NMR d (CDCl$_3$) 0.89 (3H, t, CH2CH3), 1.0–1.8 (20H, m, 10×(CH$_2$)), 2.2 (2H, t, CH$_2$=O), 3.2 (2H, t, SCH2), 3.78 (2H, t, NCH2), 4.1 (2H, q, CH$_2$OC=O), 7.0–7.5 (10H, m, 2×Ph) ppm.

c) 1-(7-Ethoxycarbonylheptyl)-2-octylthio-4,5-diphenylimidazole (1 g) was reacted with 2N sodium hydroxide in a method similar to Example 10 to give, after chromatography on silica gel eluted with a dichloromethane:methanol gradient, 1-(7-carboxyheptyl)-2 octylthio-4,5-diphenyl-imidazole (0.47 g, 49%) as an oil. Found: C, 73.56; H, 8.59; N, 5.60; S, 6.47%; C$_{31}$H$_{42}$N$_2$O$_2$S requires: C, 73.47; H, 8.35; N, 5.53; S, 6.33%.

EXAMPLE 32

1-(7-ethoxycarbonyl-heptyl)-4,5-bis(4-methoxyphenyl)imidazole 4,5-Bis(4-methoxyphenyl)imidazole (1.8 g) (J. Med. Chem., 1974, 17, 1182–8) and ethyl 8-bromooctanoate (3.2 g) were reacted in a method similar to Example 9. Column chromatography on silica gel eluted with a dichloromethane:ethanol gradient gave 1-(7-ethoxycarbonyl-heptyl)-4,5-bis(4-methoxyphenyl)imidazole (2.42 g, 83%) as an oil. Found: C, 72.30; H, 7.72; N, 6.21%; C$_{27}$H$_{34}$N$_2$O$_4$ requires: C, 71.97; H, 7.61; N, 6.22%.

EXAMPLE 33

1-(7-carboxyheptyl)-4,5-bis(4-methoxyphenyl) imidazole 1-(7-Ethoxycarbonylheptyl)-4,5-bis(4-methoxyphenyl)-imidazole (0.58 g) was reacted with 2N sodium hydroxide in a method similar to Example 10. Recrystallisations from ethanol and water gave 1-(7-carboxyheptyl)-4,5-bis(4-methoxyphenyl)-imidazole (0.25 g, 46%) as a white solid, m.p. 142°–143°.

Found: C, 71.17; H, 7.20; H, 6.67%; C$_{25}$H$_{30}$N$_2$O$_4$ requires: C, 71.07; H, 7.16; N, 6.63%.

EXAMPLE 34

1-(7-carboxyheptyl)-4,5-bis(4-hydroxyphenyl) imidazole a) Boron tribromide (1.3 ml) was added to a solution of 1-(7-ethoxycarbonylheptyl)-4,5-bis(4-methoxyphenyl)-imidazole (1.25 g) in dry dichloromethane (30 ml). The reaction was stirred at room temperature for 4 h, cooled and water (20 ml) was carefully added. The resulting purple precipitate was collected and column chromatography on silica gel eluted with a dichloromethane:methanol gradient, followed by recrystallisation from ethanol and water gave 1-(7-ethoxycarbonylheptyl)-4,5-bis(4-hydroxyphenyl)-imidazole as a white solid (0.58 g, 50%), m.p. 186°–187°.

b) The above ester (0.5 g) was reacted with 2N sodium hydroxide in a method similar to Example 10. Recrystallisations from ethanol and water gave 1-(7-carboxyheptyl)-4,5-bis(4-hydroxyphenyl)-imidazole (0.16 g, 34%) as a white solid, m.p. 203°–204°. Found: C, 69.71; H, 6.70; N, 6.99%;C$_{23}$H$_{26}$N$_2$O$_4$ requires: C, 70.03; H, 6.64; N, 7.10%.

EXAMPLE 35

1-(7-carboxyheptyl)-4,5-bis-(2-chlorophenyl) imidazole a) 4,5-Bis(2-chlorophenyl)imidazole (1.2 g) (Chem. Ber., 1959, 92, 338–343) and ethyl 8-bromooctanoate (2.1 g) were reacted in a method similar to Example 9. Column chromatography on silica gel eluted with a dichloromethane:ethanol gradient gave 4,5-bis(2-chlorophenyl)-1-(7-ethoxycarbonyl-heptyl)imidazole (0.45 g, 23.7%) as an oil. NMR d (CDCl$_3$) 1.0–1.8(11H, m, 4×CH2, CH3), 2.2 (2H, t, CH$_2$C=O), 3.8 (2H, m, N—CH2), 4.1(2H, q, CH$_2$OC=O), 7.1–7.45 (8H, m, ArH), 7.69 (1H, s, N=CH) ppm b) 4,5-Bis(2-chlorophenyl)-1-(7-ethoxycarbonylheptyl)-imidazole (0.4 g) was reacted with 2N sodium hydroxide in a method similar to Example 10. Work-up and chromatography on silica gel eluted with a dichloromethane:methanol gradient followed by recrystallisation from dichloromethane and hexane gave 1-(7-carboxyheptyl)-4,5-bis-(2-chlorophenyl)imidazole (0.25 g, 67%) as a white solid, m.p. 145°–6°.

Found: C, 64.20; H, 5.61; N, 6.64; Cl, 16.62%; C$_{23}$H$_{24}$Cl$_2$N$_2$O$_2$ Requires: C, 64.04; H, 5.61; N, 6.49; Cl, 16.44%.

EXAMPLE 36

1-(7-carboxyheptyl)-4,5-bis(2-chloro-phenyl)-2-phenylimidazole a) 4,5-Bis(2-chlorophenyl)-2-phenylimidazole (1.7 g) (J. Org. Chem., 1971, 36, 2262) was reacted with ethyl 8-bromooctanoate in a method similar to Example 9. Column chromatography on silica gel eluted with a dichloromethane:ethanol gradient gave 4,5-bis(2-chloro-phenyl)-1-(7-ethoxycarbonylheptyl)-2-phenylimidazole (1.94 g, 77.6%) as an oil.

NMR d (CDCl$_3$) 0.8–1.5 (10H, m, 5×CH2), 2.18(2H, t, CH$_2$C=O), 3.85 (2H, m, NCH2), 4.1 (2H, q, CH$_2$OC=O), 7.1–7.5 (13H, m, ArH) ppm.

b) 4,5-Bis(2-chlorophenyl)-1-(7-ethoxycarbonylheptyl)-2-phenylimidazole (1.9 g) was reacted with 2N sodium hydroxide in a method similar to Example 10. The aqueous reaction mixture was evaporated to remove ethanol and acidified to pH 5 with 2N aqueous hydrochloric acid. The resulting white solid was collected and recrystallisation from ethanol gave 1-(7-carboxyheptyl)-4,5-bis(2-chloro-phenyl)-2-phenylimidazole (1.31 g, 73%) as a white solid, m.p. 198°. Found: C, 68.53; H, 5.60; N, 5.37; Cl, 14.79%; C$_{29}$H28Cl$_2$N$_2$O$_2$ 0.2% w/w C$_2$H$_5$OH requires: C, 68.31; H, 5.70; N, 5.40, Cl, 13.69%

EXAMPLE 37

1-(7-carboxyheptyl)-4,5-bis(4-methoxy-phenyl)-2-phenylimidazole a) 4,5-Bis(4-methoxyphenyl)-2-phenylimidazole (7 g) (J. Med. Chem., 1974, 17, 1182–8) and ethyl 8-bromo-octanoate (9.9 g) were reacted in a method similar to Example 9. Column chromatography on silica gel eluted with a hexane:ethyl acetate gradient gave 1-(7-ethoxy-carbonylheptyl)-4,5-bis(4-methoxyphenyl)-2-phenyl-imidazole (10.3 g, 100%) as an oil.

NMR d (CDCl$_3$) 0.8–1.5 (13H, m, 5×CH$_2$, CH$_3$), 2.18 (2H, t, CH$_2$=O), 3.75 (3H, s, OCH$_3$), 3.88 (5H, m, NCH$_2$, OCH$_3$), 4.1 (2H, q, CH$_2$OC=O), 6.7–7.7 (13H, m, ArH) ppm.

b) 1-(7-Ethoxycarbonylheptyl)-4,5-bis(4-methoxyphenyl)-2-phenylimidazole (10 g) was reacted with 2N sodium hydroxide in a method similar to Example 10. The aqueous reaction mixture was evaporated to dryness in vacuo and the residue was mixed with ethanol (150 ml) and insoluble material was filtered off. The filtrate was evaporated to dryness and the residue was purified by column chromatography on silica gel eluted with a dichloromethane:methanol gradient. Further purification on Amberlite resin IRA-400 eluted with a methanol:water to methanol:2N HCl gradient and recrystallisation from ethanol gave 1-(7-carboxyheptyl)-4,5-bis(4-methoxy-phenyl)-2-phenylimidazole (2.01 g, 21%) as a white solid, m.p. 149°–150°. Found: C, 74.50; H, 6.75; N, 5.69%; $C_{31}H_{34}N_2O_4$ 0.5% w/w $C_2H_5OH$ requires: C, 74.56; H, 6.90; N, 5.59%.

EXAMPLE 38

1-(7-carboxyheptyl)-4,5-bis-(4-hydroxyphenyl)-2-phenylimidazole

Boron tribromide (0.7 ml) was added to a suspension of 1-(7-carboxyheptyl)-4,5-bis(4-methoxyphenyl)-2-phenylimidazole (0.7 g) in anhydrous dichloromethane (20 ml) and the reaction was stirred at room temperature for 1 h. Boron tribromide (0.3 ml) was added and the reaction was stirred at reflux for 2 h and at room temperature for 20 h. Water was carefully added to the cooled reaction mixture and the resulting yellow precipitate was collected. Column chromatography on silica gel eluted with a dichloromethane:methanol gradient and recrystallisation from ethanol and water gave 1-(7-carboxyheptyl)-4,5-bis-(4-hydroxyphenyl)-2-phenylimidazole (0.44 g, 67%) as a cream solid, m.p 135°–7°; Found C, 73.97; H, 6.38; N, 5.98%; $C_{29}H_{30}N_2O_4$ requires: C, 74.02; H, 6.42; N, 5.95%.

EXAMPLE 39

8-(4,5-di-(4-bromophenyl)imidazol-1-yl)-octanoate 4,5-Di-(4-bromophenyl)imidazole (2.13 g) was treated with ethyl 8-bromooctanoate (2 g) and $K_2CO_3$ (0.5 g) in 2-butanone as described in Example 9 to give ethyl 8-(4,5-di-(4-bromophenyl)imidazol-1-yl)-octanoate (2.2 g, 52%) as a pale yellow oil.; Found: C, 55.13; H, 5.19; N, 5.18; Br, 28.76%; $C_{28}H_{28}Br_2N_2O_2$ requires: C, 54.76; H, 5.15; N, 5.11; Br, 29.15%

EXAMPLE 40

1-(7-carboxyheptyl)-2-heptyl-4,5-diphenylimidazole a) 2-Heptyl-4,5-diphenylimidazole (1 g) was reacted with ethyl 8-bromooctanoate (1.6 g) in a method similar to Example 9 with a reaction time of 48 hours. Chromatography on silica gel (hexane/ethyl acetate) gave 1-(7-ethoxycarbonyl-heptyl)-2-heptyl-4,5-diphenylimidazole (1.3 g, 87%) as an oil. Found: C, 78.98; H, 9.22; N, 5.76%; $C_{32}H_{44}N_2O_2$ requires: C, 78.64; H, 9.08; N, 5.73%;

b) 1-(7-Ethoxycarbonylheptyl)-2-heptyl-4,5-diphenylimidazole (1 g) was reacted with sodium hydroxide in a method similar to Example 10 to give, after column chromatography on silica gel (dichloromethane/methanol) and recrystallisation from hexane, 1-(7-carboxyheptyl)-2-heptyl-4,5-diphenylimidazole (0.26 g, 28%) as a white solid, m.p. 75°–6°. Found: C, 78.04; H, 8.85; N, 6.10%; $C_{30}H_{40}N_2O_2$ requires: C, 78.22; H, 8.75; N, 6.08%;

EXAMPLE 41

6-(2,4,5-triphenylimidazol-1-yl)hexylthio-acetic acid

To a solution of sodium (0.17 g) in dry methanol (10 ml) was added mercaptoacetic acid (0.3 g followed by 1-(6-bromohexyl)-2,4,5-triphenylimidazole (1.38 g). The suspension was stirred at room temperature for 2 hours then at reflux temperature for 4 hours. The solvent was evaporated and the residue was dissolved in water and acidified to pH 4 with dilute hydrochloric acid. The precipitated oil was taken up in dichloromethane, washed with water, dried over magnesium sulphate and evaporated to an oil which was chromatographed on silica gel (dichloromethane/methanol) giving, after recrystallisation from ethanol, 6-(2,4,5-triphenylimidazol-1-yl)hexylthio-acetic acid (0.86 g, 61%) as a colourless crystalline solid, m.p. 158–9° C. Found: C, 74.14; H, 6.43; N, 5.77; S, 6.91%; $C_{29}H_{30}N_2O_2S$ requires: C, 74.01; H, 6.43; N, 5.95; S, 6.81%

EXAMPLE 42

5-(2,4,5-triphenylimidazole-1-yl)pentyl-thioacetic acid a) A mixture of 2,4,5-triphenylimidazole (20 g), dibromopentane (62 g) and potassium carbonate (18 g) in dry butanone (200 ml) was heated at reflux temperature for 24 hours. The mixture was filtered and the filtrate evaporated to an oil. This was washed with hexane then chromato-graphed on silica gel (hexane/ethyl acetate) to give 1-(5-bromopentyl)-2,4,5-triphenyl-imidazole (7.9 g, 27%) as a pale yellow oil.

NMR d (CDCl$_3$) 1.0–1.6 (3H, m, 3×CH$_2$), 3.1 (2H, t, CH$_2$Br), 3.9 (2H, t, CH$_2$N), 7.1–7.7 (15H, m, 3×Ph) ppm.

b) Mercaptoacetic acid (0.3 g) and 1-(5-bromopentyl)-2,4,5-triphenylimidazole (1.34 g) were reacted in a method similar to example 42 (a) above giving, after recrystallisation from isopropanol, 5-(2,4,5-triphenylimidazol-1-yl) pentyl-thioacetic acid (0.52 g, 38%) as a colourless crystalline solid, m.p. 166°–9° C.; Found: C, 72.98; H, 6.07; N, 5.87; S, 6.90%; $C_{28}H_{28}N_2O_2S$+1% isopropanol+0.5% water requires: C, 73.15; H, 6.28; N, 6.04; S, 6.92%

EXAMPLE 43

7-(1,2,4-triphenylimidazolyl)-hept-5-ynoic acid

A solution of 2,4,5-triphenylimidazole (1.07 g) in dimethyl-formamide (20 ml) was treated with sodium hydride 50% in oil (0.17 g) and methyl 7-bromohept-5-ynoate (0.95 g). The solution was stirred for 18 hours when the solvent was removed under reduced pressure and the residue was chromatographed on silica gel eluted with chloroform-hexane to give a clear oil which was dissolved in methanol (20 ml) and treated with 10% potassium hydroxide solution (10 ml) for 2 hours. The methanol was removed under reduced pressure and the remaining aqueous was acidified (pH 3) and filtered. The filtrate was extracted with chloroform (3×50 ml). The chloroform extracts were dried over magnesium sulphate, filtered and the solvent removed to give a solid which was recrystallised from acetonitrile to give 7-(1,2,4-triphenyl-imidazolyl)-hept-5-ynoic acid as white prisms, m.p. 144°–145° C.; Found: C, 79.99; H, 5.81; N, 6.40% ($C_{28}H_{24}N_2O_2$);Requires: C, 79.97; H, 5.75; N, 6.66%

EXAMPLE 44

9-(1,2,4-tri-phenylimidazolyl)-2,2-dimethylnonanoic acid

A mixture of 2,4,5-triphenylimidazole (4.13 g), ethyl 9-bromo-2,2-dimethylnonanoate (10.95 g), potassium carbonate (10 g) and 2-butanone was stirred at reflux for 48 hours. The mixture was filtered, solvent removed under reduced pressure and the residue was chromatographed on silica gel eluted with chloroform to give a clear oil which was dissolved in dimethyl sulphoxide (30 ml) and treated with potassium hydroxide (3 g). The mixture was stirred at 40° C. for 24 hours when the solvent was removed under reduced pressure. Water (50 ml) was added, the pH of the solution was adjusted to 4 and the aqueous was extracted with chloroform (3×50 ml). The chloroform extracts were dried over magnesium sulphate, filtered and the solvent removed to give a solid which was recrystallised from acetonitrile to give 9-(1,2,4-tri-phenylimidazolyl)-2,2-dimethylnonanoic acid as a white crystalline solid, m.p. 119°–120° C.; Found: C, 79.85; H, 7.64; N, 6.23% ($C_{32}H_{36}N_2O_2$); Requires: C, 79.96; H, 5.54; N, 5.82%

EXAMPLE 45

4-[4-(2,4,5-triphenylimidazolyl)butyloxy]benzoic acid a) A mixture of 1,4 dibromobutane (50 ml), methyl 4-hydroxy-benzoate (15.2 g, 0.1 mole), potassium carbonate (40 g) in 2-butanone (500 ml) was refluxed for 24 hours. The mixture was filtered, solvent removed and the residue was chromatographed on silica gel eluted with chloroform/petrol and recrystallised from pentane to give methyl 4-(4-bromobutyloxy)benzoate (19.26 g).

b) A mixture of 2,4,5-triphenylimidazole (5.93 g), methyl 4-(4-bromobutyloxy)benzoate (3.81 g), potassium carbonate (25 g) and 2-butanone (250 ml) was stirred at reflux for 36 hours. The mixture was filtered, solvent removed under reduced pressure and the residue was chromatographed on silica gel eluted with chloroform and recrystallised from methanol to give 4-[4-(2,4,5-triphenylimidazolyl)butyloxy] benzoate as a white crystalline solid (5.38 g), m.p. 145°–146° C.; Found: C, 79.16; H, 6.15; N, 6.03% ($C_{33}H_{30}N_2O_3$); Requires: C, 78.86; H, 6.01; N, 5.57% c) Methyl 4-[4-(2,4,5 triphenylimidazolyl]butyloxy)-benzoate (1.5 g) was dissolved in methanol (50 ml) and treated with 10% potassium hydroxide solution (15 ml) for 0.5 hours. The methanol was removed under reduced pressure and the remaining aqueous was acidified (pH 4) and the pre-cipitate was collected by filtration and recrystallised from methanol to give 4-[4-(2,4,5-triphenylimidazolyl)-butyloxy]-benzoic acid (1.3 g) as white prisms m.p. 202°–203° C.; Found: C, 78.79; H, 5.75; N, 5.81% ($C_{32}H_{28}N_2O_3$); Requires: C, 78.66; H, 5.78; N, 5.73%

EXAMPLE 46

7-(2,4,5-tri-phenylimidazol-1-yl)heptane-sulphonate 2,4,5-Triphenyl-1-(7-bromoheptyl)imidazole (0.95 g) was dissolved in hot ethanol (10 ml) and a solution of sodium sulphite (0.38 g) in hot water (5 ml) was added. The white suspension was heated at reflux temperature for 20 hours then evaporated to dryness. The mixture was taken up in dichloromethane, filtered and the filtrate evaporated to an oil which was chromatographed on silica gel (dichloromethane/methanol). The resulting oil was dissolved in methanol and excess ether added giving an oil which slowly solidified to give sodium 7-(2,4,5-tri-phenylimidazol-1-yl)heptane-sulphonate (0.32 g; 32%) as a white solid, m.p. 310° C.

Found: C, 65.98; H, 6.11; N, 5.71; S, 6.22%; $C_{28}H_{29}N_2NaO_3S+2.5\%$ $H_2O$ requires: C, 66.03; H, 6.02; N, 5.50; S, 6.30%

EXAMPLE 47

7-(2,4,5-triphenylimidazol-1-yl)heptanephosphonic acid

A mixture of 2,4,5-triphenyl-1-(7-bromoheptyl)-imidazole (0.95 g) and triethyl phosphite (1.66 g) in xylene (5 ml) was heated at reflux temperature for 20 hours. The mixture was evaporated to an oil and chromatographed on silica gel (ethyl acetate/ethanol) to give diethyl 7-(2,4,5-triphenylimidazol-1-yl)heptane-phosphonate (0.37 g, 35%) as a light brown oil.

NMR ù ($CDCl_3$) 0.9–1.7 (18H, m, 6×$CH_2$+2×$CH_3$), 3.9 (2H, t, $CH_2N$), 4.1 (4H, m, 2×$CH_2O$), 7.1–7.7 (15H, m, 3×Ph) ppm.

Diethyl 7-(2,4,5-triphenylimidazol-1-yl)heptane-phosphonate (0.35 g) was dissolved in dry chloroform, cooled to –40° C. and to it was added trimethylsilyl iodide (0.66 g) over 2 minutes under an atmosphere of nitrogen. The cooling bath was removed and the reaction mixture was stirred for 3 hours at room temperature then evaporated to an oil and revaporated evaporated from methanol and water respectively. The oil was taken up in methanol, treated with excess aqueous sodium bicarbonate, evaporated to dryness then taken up in ethanol, filtered and the filtrate evaporated to an oil. This was taken up in water, filtered and dilute hydrochloric acid added to pH4. The precipitated oil was washed with water, taken up in methanol and precipitated with ether to give 7-(2,4,5-triphenylimidazol-1-yl)heptane-phosphonic acid (0.16 g, 51%) as a light brown oil. Found: C, 68.12; H, 6.39, N, 5.60% $C_{28}H_{31}N_2O_3P+4\%$ $H_2O$ requires: C, 68.03; H 6.76); N, 5.66%.

EXAMPLE 48

Ethyl 8-(phenanthrimidazol-1-yl)octanoate

Phenanthrimidazole (2.18 g) (J. Am. Chem. Soc., 1943, 65, 452–6) was treated with ethyl 8-bromooctanoate (5.02 g) and $K_2CO_3$ (2.76 g) in 2-butanone (100 ml) as described in Example 9 to give, after work up and chromatography, ethyl 8-(phenanthrimidazol-1-yl)octanoate (0.8 g, 20%) as off white crystals, m.p. 99°–101° C.; Found: C, 77.34; H, 7.19; N, 7.04%; $C_{25}H_{28}N_2O_2$ requires: C, 77.29; H, 7.26; N, 7.21%

EXAMPLE 49

1-(7-carboxyheptyl )-2-(5-formylpentyl)-4,5-diphenylimidazole a) A mixture of 4,5-diphenyl-2-imidazolethiol (2.66 g), 2-(5-iodopentyl)-1,3-dioxalane (3 g), anhydrous potassium carbonate (7.26 g) and dry 2-butanone (70 ml) was heated at reflux for 4 hours. The cooled reaction mixture was filtered and the filtrate was evaporated to dryness in vacuo. The residue was stirred under hexane and the resulting white precipitate was collected by filtration. Recrystallisations from ethanol/water and dichloro-methane/hexane gave 2-(5-[1,3-dioxalan-2-yl]heptyl-thio)-4,5-diphenylimidazole (3.1 g, 75%) as a white solid, m.p. 116°–118° C.; NMR d ($CDCl_3$) 1.5–1.7 (8H, m, 4×$CH_2$), 3.09 (2H, t, $SCH_2$), 3.8–4.0 (4H, m, O($CH_2$)$_2$O), 4.8 (1H, t, CH), 7.1–7.7 (10H, m, 2×Ph) ppm.

b) 2-(5-[1,3-dioxalan-2-yl]pentylthio]-4,5-diphenyl-imidazole (3 g) and ethyl 8-bromooctanoate (3.82 g) were reacted in a method similar to Example 9. Distillation to remove volatile impurities and column chromatography on silica gel (dichloro-methane/ethanol) gave 2-(5-[1,3- dioxalan-2-yl]heptylthio)-1-(7-ethoxycarbonylpentyl)-4,5-diphenyl-imidazole (3.02 g, 70%) as a colourless oil. Found: C, 70.23; H, 8.09; N, 5.04; S, 5.85%; $C_{33}H_{44}N_2O_4S$ requires: C, 70.18; H, 7.85; N, 4.96; S, 5.65% c) 2-(5-[1,3-Dioxalan-2-yl]pentylthio)-1-(7-ethoxy-carbonylheptyl)-4,5-diphenylimidazole (7 g) was reacted with 2N sodium hydroxide in a method similar to Example 10. Work-up and column chromatography on silica gel (dichloromethane/methanol) gave 1-(7-carboxyheptyl)-2-[5-(1,3-dioxalan-2-yl]pentylthio)-4,5-diphenylimidazole (6.44 g, 89%) as a colourless oil. NMR ù ($CDCl_3$) 1.0–1.9 (18H, m, 9×$CH_2$), 2.3 (2H, t, $CH_2$), 3.2 (2H, t, $SCH_2$), 3.7–4.0 (6H, m, O($CH_2$)$_2$O, $NCH_2$), 4.8 (1H, m, CH), 7.0–7.5 (10H, m, 2×Ph) ppm.

d) A mixture of 1-(7-carboxyheptyl)-2-(5-[1,3-dioxalan-2-yl]pentylthio)-4,5-diphenyl imidazole (2 g), tetrahydrofuran (100 ml), water (100m 1) and concentrated hydrochloric acid (10 ml) was stirred at 90° C. for 1 hour. The reaction mixture was evaporated to remove tetrahydrofuran and the aqueous was extracted with diethyl ether (3×75 ml). The extracts were combined and washed with water (3×75 ml), dried over anhydrous magnesium sulphate and evaporated to dryness in vacuo. Column chromatography on silica gel (dichloro-methane/methanol) gave 1-(7-carboxyheptyl)-2-(5-formylpentyl)-4,5-diphenyl-imidazole (0.93 g, 50%) as a colourless oil. Found: C, 70.62; H, 7.88; N, 5.32; S, 6.34%; $C_{29}H_{36}N_2SO_3$ requires: C, 70.70; H, 7.37; N, 5.39; S, 6.51%

EXAMPLE 50

Sodium 6-(1,4,5-triphenylimidazol-2-yloxy) hexanesulphonate

A mixture of 1,4,5-triphenylimidazol-2-one (6.25 g), dibromohexane (24.4 g) and potassium carbonate (5.53 g) in dry butanone (300 ml) was heated at reflux temperature for 24 hours. The mixture was cooled and the filtrate evaporated to an oil which was chromatographed on silica gel (hexane/ethyl acetate) to give 1,4,5-triphenyl-2-(6-bromohexyloxy)-imidazole (2.8 g, 29%) as a white solid, m.p. 87°–9° C.

NMR d ($CDCl_3$) 1.3–1.9 (8H, m, 5×$CH_2$), 3.4 (2H, t, —$CH_2$Br), 4.5 (2H, t, —$CH_2$O), 7.0–7.6 (15H, m, 3×pH) ppm.

1,4,5-Triphenyl-2-(6-bromohexyloxy)imidazole (0.95 g) was dissolved in hot ethanol (5 ml) and a solution of sodium sulphite (0.25 g) in hot water (3 ml) was added. The white suspension was heated at reflux for 24 hours then evaporated to dryness. The residue was recrystallised from ethanol then methanol/ethanol to give sodium 6-(1,4,5-triphenylimidazol-2-yloxy)hexane-sulphonate (0.15 g, 15%) as a colourless solid, m.p. 265° C.

Found: C, 64.22; H, 5.51; N, 5.32; S, 6.24%$C_{27}H_{27}N_2NaO_4S$+1.2% $H_2O$+0.5% EtOH; Requires: C, 64.20; H, 5.57; N, 5.52; S, 6.32%.

EXAMPLE 51

Sodium 7-(1,4,5-triphenylimidazol-2-yloxy) heptanesulphonate

A mixture of 1,4,5-triphenylimidazol-2-one (15.3 g), dibromoheptane (50.6 g) and potassium carbonate (13.8 g) was heated at reflux temperature in dry butanone (750 ml) for 20 hours. The mixture was cooled, filtered and the filtrate evaporated to an oil which was chromatographed on silica gel (hexane/ethyl acetate) to give 1,4,5-triphenyl-2-(7-bromoheptyloxy)imidazole (5.0 g, 21%) as a white solid, m.p. 97°–9° C.

NMR d ($CDCl_3$) 1.3–1.9 (10H, m, 5×$CH_2$), 3.4 (2H, t, —$CH_2$Br), 4.5 (2H, t, —$CH_2$O), 7.0–7.6 (15H, m, 3×Ph) ppm.

A solution of 1,4,5-triphenyl-2-(7-bromoheptyloxy)-imidazole (2.0 g) in ethanol (10 ml) was refluxed with a solution of sodium sulphite (0.55 g) in water (5 ml) for 20 hours. More sodium sulphite (0.2 g) in water (1 ml) was added and refluxed a further 20 hours. The mixture was evaporated to dryness, boiling ethanol added and filtered hot. Chromatography of the filtrate on silica gel (dichloromethane/methanol 5:1) followed by crystallisation from ethanol/isopropanol gave sodium 7-(1,4,5-triphenylimidazol-2-yloxy)heptanesulphonate (0.3 g, 15%) as a colourless solid, m.p. 246°–8° C. Found: C, 64.47; H, 5.85; N, 5.09; S, 5.50%; $C_{28}H_{29}N_2NaO_4S$+2% isopropanol +2% water, Requires: C, 64.19; H, 5.96;N, 5.25; S, 6.01%.

EXAMPLE 52

Ethyl 7-(1,4,5-triphenylimidazol-2-yloxy) heptanemethyl-phosphinate

A solution of 1,4,5-triphenyl-2-(7-bromoheptyloxy)-imidazole (1.75 g) and diethyl methylphosphonite (2.45 g) in toluene (10 ml) was heated at reflux temperature for 48 hours. Methanol and water were added and the mixture evaporated to an oil. This was chromatographed on silica gel (ethyl acetate/ethanol). The resulting oil slowly crystallised and was triturated with ether/petroleum ether, filtered then recrystallised from ethanol/ether to give ethyl 7-(1,4,5-triphenyl-imidazol-2-yloxy)heptane-methylphosphinate (1.06 g, 57%) as a white solid, m.p. 101°–2° C. Found: C, 72.05; H, 7.26; N, 5.52%; $C_{31}H_{37}N_2O_3P$; Requires: C, 72.07; H, 7.22; N, 5.42%.

EXAMPLE 53

Diethyl 7-(1,4,5-triphenylimidazol-2-yloxy) heptanephosphonate

A mixture of 1,4,5-triphenyl-3-(7-bromoheptyl)-imidazol-2-one (1.0 g) and triethyl phosphite (1.66 g) was heated at reflux temperature in xylene (5 ml) for 40 hours. The solution was evaporated to an oil and re-evaporated from ethanol. The oil was partitioned between ether and water, the ether solution was separated, dried over magnesium sulphate and evaporated to an oil which was chromatographed on silica gel (ethyl acetate) to give diethyl 7-(1,4,5-triphenylimidazol-2-yl-oxy)heptanephosphonate as an oil which solidified on standing to a white solid (0.83 g; 75%), m.p. 76°–7° C. Found: C, 70.49; H, 7.40; N, 4.94%; $C_{32}H_{39}N_2O_4P$; Requires: C, 70.31; H, 7.19; N, 5.12%.

EXAMPLES 54 and 55

7-(3,4,5-Triphenyl-2-oxo-2,3-dihydroimidazol-1-yl) heptanonitrile; and 7-(1,4,5-Triphenylimidazol-2-yloxy)heptanonitrile 1,4,5-Triphenylimidazol-2-one was treated with 7-bromo-heptanonitrile and potassium carbonate in butanone to give after chromatographic work-up 7-(3,4,5-triphenyl-2-oxo-2,3-dihydroimidazol-1-yl)heptanonitrile, m.p. 100°–101° C., Found: C, 79.7; H, 6.6; N, 9.8%; $C_{28}H_{27}N_3O$ requires: C, 79.9; H, 6.4; N, 10.0%; and 7-(1,4,5-triphenylimidazol-2-yloxy)heptanonitrile, m.p. 93°–94° C., Found: C, 79.5; H, 6.6; N, 9.7%; $C_{28}H_{27}N_3O$ requires: C, 79.9; H, 6.4; N, 10.0%.

EXAMPLES 56 AND 57

1-(7-Methoxycarbonylheptyl)-4,5-diphenyltriazole; and 2-(7-Methoxycarbonylheptyl)-4,5-diphenyltriazole A solution of 8-bromooctanoic acid (8.32 g) and sodium hydroxide (1.49 g) in water (50 ml) was added to solution of 4,5-diphenyltriazole (7.5 g) (Chem. Ber., 1970, 103, 1908–17) and sodium hydroxide (1.36 g) in water (75 ml) and the mixture was stirred at 80° C. for 21 hours.

2N Aqueous hydrochloric acid (50 ml) was carefully added to the cooled reaction and then extracted with diethyl ether (3×100 ml). The ether extracts were combined, washed with water (100 ml), dried over anhydrous magnesium sulphate and evaporated to dryness in vacuo to give a mixture of 1(2)-(7-carboxyheptyl)-4,5-diphenyltriazole (12.2 g) as an oil.

The above mixture (12.2 g), p-toluene sulphonic acid, monohydrate (1.2 g) and methanol (250 ml) were heated at reflux through a soxhlet extractor containing 4A molecular sieves for 3.5 hours. The methanol was removed in vacuo and the residue was dissolved in dichloromethane (250 ml), washed with saturated sodium hydrogen carbonate solution (200 ml), water (200 ml), dried over anhydrous magnesium sulphate and evaporated to dryness in vacuo. Column chromatography on silica gel eluted with dichloromethane gave 1-(7-methoxycarbonylheptyl)-4,5-diphenyltriazole (Example 56) (2.4 g, 19.4%) and 2-(7- methoxycarbonylheptyl)-4,5-diphenyltriazole. (Example 57) (3.2 g, 25.2%) as oils. Example 56 found: C, 72.85; H; 7.23; N, 10.93% Example 57 found: C, 73.08, H; 7.20; N, 11.00% $C_{23}H_{27}N_3O_2$ requires: C, 73.18; H, 7.21; N, 11.13%

EXAMPLE 58

1-(7-Carboxyheptyl)-4,5-diphenyltriazole 1-(7-Methoxycarbonylheptyl)-4,5-diphenyltxiazole (1 g) was treated with 2N sodium hydroxide in aqueous ethanol at reflux temperature for 2.5 hours. The ethanol was removed in vacuo and the residual mixture acidified with 2N aq HCl. The aqueous solution was extracted with ethyl acetate and the organic extracts combined, dried over magnesium sulphate and evaporated to dryness in vacuo. Recrystallisation from ethanol and water gave 1-(7-carboxyheptyl)-4,5-diphenyltriazole (0.61 g, 64%) as a white solid, m.p. 103°–104° C.

Found: C, 72.66; H, 6.92; N, 11.44% $C_{22}H_{25}N_3O_2$ requires: C, 72.70; H, 6.93; N, 11.56%

EXAMPLE 59

2-(7-Carboxyheptyl)-4,5-diphenyltriazole 2-(7-Methoxycarbonylheptyl)-4,5-diphenyltriazole (1 g) was reacted with 2N sodium hydroxide in a method similar to Example 58. Recrystallisation from ethanol and water gave 2-(7-carboxyheptyl)-4,5-diphenyltriazole (0.76 g, 79%) as a white solid, m.p. 86°–88° C.

Found: C, 72.70; H, 6.94; N, 11.47% $C_{22}H_{25}N_3O_2$ requires: C, 72.70; H, 6.93; N, 11.56%

EXAMPLE 60

2-(8-Carboxyoctyl)-4,5-diphenyltriazole a) A mixture of 4,5-diphenyltriazole (11 g), 1,8-dibromooctane (67.6 g), and potassium carbonate (10.31 g) in dry butanone (300 ml) was heated at reflux temperature for 24 hours. The mixture was filtered and the solvent evaporated to give an oily residue. Distillation to remove 1,8-dibromooctane and column chromatography on silica gel eluted with a hexane:ethyl acetate gradient gave 2-(8-bromooctyl)-4,5-diphenyl-triazole (11.13 g, 54%) as an oil. NMR d (CDCl$_3$) 1.2–1.5 (8H, m, 4×CH$_2$), 1.84 (2H, m, CH$_2$), 2.05 (2H, m, CH$_2$), 3.37 (2H, t, Br—CH$_2$), 4.47 (2H, t, N—CH$_2$), 7.3–7.6 (10H, m, 2×Ph) ppm
1-(8-Bromooctyl)-4,5-diphenyl-1,2,3-triazole b) 4,5-Diphenyl-1,2,3-triazole was treated with 1,8-dibromooctane and potassium carbonate in butanone to give after chromatographic work up the title compound, m.p. 90°–91° C., Found: C, 64.0; H, 6.5; N, 10.1; Br, 19.8%; $C_{22}H_{26}BrN_3$ requires: C, 64.1;H, 6.4; N, 10.2; Br, 19.4%.

And 1-(8-bromooctyl)-4,5-diphenyltriazole (2.12 g, 10.3%) as a white solid, m.p. 90°–91° C. after recrystallisation from hexane.

Found: C, 64.01; H, 6.47; N, 10.09; Br, 19.84%; $C_{22}H_{26}BrN_3$ requires C, 64.08; H, 6.36; N, 10.19; Br, 19.38%

NMR d (CDCl$_3$) 1.1–1.5 (8H, m, 4×CH$_2$), 1.65–1.9 (4H, m, 2×CH$_2$), 3.37 (2H, t, Br—CH$_2$), 4.20 (2H, t, NCH$_2$), 7.2–7.55 (10H, m, 2×Ph) ppm c) 2-(8-Bromooctyl)-4,5-diphenyltriazole (7 g) in dimethylsulphoxide (220 ml) was added to a suspension of sodium cyanide (1 g) in dimethylsulphoxide (60 ml) over 15 minutes. The reaction mixture was stirred at 24° C. for 1 hour and at 50° C. for 2 hours. The cooled reaction mixture was poured into water (600 ml), extracted with diethyl ether (4×200 ml). The extracts were combined, washed with water (100 ml), dried over anhydrous magnesium sulphate and evaporated to dryness in vacuo. Column chromatography on silica gel eluted with a hexane:ethyl acetate gradient gave 2-(8-cyanooctyl)-4,5-diphenyl-triazole (5.6 g, 92%) as an oil.

Found: C, 75.13; H, 7.16; N, 15.24%; $C_{23}H_{26}N_4$0.5H$_2$O requires: C, 75.18; H, 7.41; N, 15.25.

d) 2-(8-Cyanooctyl)-4,5-diphenyltriazole (3.0 g) was treated with sulphuric acid (50 ml) and water (50 ml) and the mixture heated at reflux temperature for 4 hours. Water (200 ml) was added and the cooled mixture was extracted with ethyl acetate (3×75 ml), and the organic extracts combined and evaporated to give a solid. Recrystallisation from ethanol and water gave 2-(8-carboxyoctyl)-4,5-diphenyltriazole (2.37 g, 75%) as a white solid m.p. 84°–85° C. Found: C, 72.92; H, 7.20; N, 11.07%; $C_{23}H_{27}N_3O_2$ requires: C, 73.18; H, 7.21; N, 11.13%.

EXAMPLE 61

1-(8-Carboxyoctyl)-4,5-diphenyltriazole a) 1-(8-Bromooctyl)-4,5-diphenyltriazole (ex. example 60a) (1.8 g) was reacted with sodium cyanide in a method similar to Example 60b). Work-up and recrystallisation from dichloromethane and hexane gave 1-(8-cyanooctyl)-4,5-diphenyltriazole (1.16 g, 74.4%) as a white solid, m.p. 77°–8° C. Found: C, 77.03; H, 7.25; N, 15.35%; $C_{23}H_{26}N_4$ requires: C, 77.06; H, 7.31; N, 15.63%.

b) 1-(8-Cyanooctyl)-4,5-diphenyltriazole (0.9 g) was treated with sulphuric acid in a method similar to Example 60a. Work-up and recrystallisation from ethanol and water gave 1-(8-carboxyoctyl)-4,5-diphenyltriazole (0.58 g, 64%) as a cream solid, m.p. 86°–87° C. Found: C, 73.10; H, 7.23; N, 10.82%; $C_{23}H_{27}N_3O_2$ requires: C, 73.18, H, 7.21, N, 11.13%.

EXAMPLE 62

2-(8-Ethoxycarbonyloctyl)-4,5-diphenyltriazole

A mixture of 2- (8-carboxyoctyl) -4,5-diphenyltriazole (1 g), absolute alcohol (100 ml) and concentrated sulphuric acid (1 ml) was heated at reflux temperature for 3 hours. The solvent was removed in vacuo, the residue dissolved in diethyl ether (100 ml), washed with water (50 ml), dried and evaporated. The residue was chromatographed on silica gel eluted with a hexane:ethyl acetate to give 2-(8-ethoxycarbonyloctyl)-4,5-diphenyltriazole (0.81 g, 76%) as an oil. Found: C, 73.84; H, 7.78; N, 10.22%; $C_{25}N_{31}N_3O_2$ requires: C, 74.04; H, 7.71; N, 10.36%.

EXAMPLE 63

2-(6-Ethoxycarbonylhexyl)-4,5-diphenyltriazole 4,5-Diphenyltriazole (2.0 g) and ethyl 7-bromoheptanoate (1.5 g) were reacted in a method similar to Example 60. Column chromato-graphy on silica gel eluted with a hexane:ethyl acetate gradient gave 2-(6-ethoxycarbonylhexyl)-4,5-diphenyltriazole (1.1 g, 46%) as an oil.

Found: C, 73.10; H, 7.45; N, 11.11% $C_{23}H_{27}N_3O_2$ requires C, 73.18; H, 7.21; N, 11.13%;

EXAMPLE 64

2-(6-Carboxyhexyl)4,5-triphenyltriazole 2-(6-Ethoxycarbonylhexyl)-4,5-diphenyltriazole (0.7 g) was reacted with sodium hydroxide in a method similar to Example 58. Recrystallisation from ethanol and water gave 2-(6-carboxyhexyl)4,5-triphenyltriazole (0.41 g, 63%) as white needles, m.p. 88°–89° C.

Found: C, 71.30; H, 6.54; N, 11.73%; $C_{21}H_{23}N_3O_3 \cdot 0.2H_2O$ requires: C, 71.44; H, 6.68; N, 11.90%.

EXAMPLE 65

2-(7-Carboxyheptyl)-4,5-diphenyloxazole a) A mixture of benzoin (26.15 g), 8-bromooctanoic acid (25.0 g), 4-dimethylaminopyridine (1.35 g), 1,3-dicyclohexylcarbodiimide (25.4 g) and dry tetrahydrofuran (350 ml) was stirred under nitrogen at room temperature for 20 hours. The reaction mixture was filtered and the filtrate was evaporated to dryness in vacuo. The residue was dissolved in dichloromethane (350 ml), washed with 5% aqueous hydrochloric acid (3×175 ml), saturated sodium hydrogen carbonate solution (2×200 ml), saturated sodium chloride solution (220 ml), dried over anhydrous magnesium sulphate and evaporated to dryness in vacuo. Column chromatography on silica gel eluted with a hexane: dichloromethane gradient gave a yellow oil. This oil was stirred in hexane to give 2-oxo-1,2- diphenyl-ethyl 8-bromooctanoate (27.1 g, 52.7%) as a pale yellow solid m.p. 60°–61° C.

NMR d (CDCl$_3$) 1.2–1.9 (10H, m, 5×CH$_2$), 2.46 (2H, m, CH$_2$C=O), 3.4 (2H, t, BrCH$_2$), 6.86 (1H, s, PhCH), 7.35–7.95 (10H, m, 2×Ph) ppm.

b) A mixture of the above ester (26.8 g), ammonium acetate (19.4 g) and glacial acetic acid (500 ml) was stirred at 80° C., under nitrogen, for 2 hours. The glacial acetic acid was removed in vacuo and water (1000 ml) was added. The aqueous was extracted with dichloromethane (3×250 ml). The organic extracts were combined, washed with water (200 ml), saturated sodium chloride solution (200 ml), dried over anhydrous magnesium sulphate and evaporated to dryness in vacuo. Column chromatography on silica gel eluted with dichloromethane gave 1-(7-bromoheptyl)-4,5-diphenyloxazole (14.09 g, 55%) as an oil.

NMR d (CDCl$_3$) 1.4 (6H, m, 3×CH$_2$), 1.87 (4H, m, 2×CH$_2$), 2.85 (2H, t, N=CCH$_2$), 3.41 (2H, t, BrCH$_2$), 7.3–7.7 (10H, m, 2×Ph) ppm.

c) 2-(7-Bromoheptyl)-4,5-diphenyloxazole (13.8 g) in dimethylsulphoxide (80 ml) was added over 45 minutes to a mixture of sodium cyanide (1.87 g) in dimethylsulphoxide (80 ml). The reaction was stirred at 50° C. for 2 h, cooled and poured into water (500 ml). The aqueous was extracted with diethyl ether (4×250 ml). The ether extracts were combined, washed with water (250 ml), dried over anhydrous magnesium sulphate and evaporated to dryness in vacuo. Column chromatography on silica gel eluted with a hexane: dichloromethane gradient gave 2-(7-cyanoheptyl)-4,5-diphenyloxazole (4.89 g, 41%) as an oil. Found: C, 80.20; H, 7.02; N, 8.13%; $C_{23}H_{24}N_2O$ requires: C, 80.31; H, 7.18; n, 8.16%;

d) 2-(7-Cyanoheptyl)-4,5-diphenyloxazole (2.5 g) was reacted with sulphuric acid in a method similar to Example 60c. Recrystallisation from ethanol and water gave 2-(7-carboxyheptyl)-4,5-diphenyloxazole (1.1 g, 41.7%) as a cream solid, m.p. 82°–83° C. Found: C, 76.07; H, 6.99; N, 3.79%;

$C_{23}H_{25}NO_3$ requires: C, 76.00; H, 6.93; N, 3.85%.

EXAMPLES 66 & 67

8-(3,4-Diphenylpyrazol-1-yl)octanoic acid, and 8-(4,5-Diphenylpyrazol-1-yl)octanoic acid a) Formyldeoxybenzoin (10 g) was suspended in ethanol (50 ml) and hydrazine hydrate (5 ml) added giving an orange solution which warmed to 40° C. This solution was stirred at room temperature for 3 hours and the solvent evaporated. The resulting oil was taken up in dichloromethane and washed with dilute hydrochloric acid (pH 2) and water, dried over potassium carbonate and evaporated to an orange solid. This was boiled in ether, cooled and filtered giving 3,4-diphenylpyrazole (5.64 g, 57%) as pale yellow crystals, m.p. 155°–6° C.

NMR d (CDCl$_3$) 7.2–7.5 (10H, m, 2×Ph), 7.6 (1H, s, pyraz 5-H) ppm b) A mixture of 3,4-diphenylpyrazole (2.2 g), ethyl 8-bromooctanoate (5.5 g) and potassium carbonate (3.7 g) in dry butanone (50 ml) was heated at reflux temperature for 44 hours. The mixture was filtered and the filtrate evaporated to an oil which was chromatographed on silica gel (hexane/ethyl acetate). The oil obtained was heated at reflux temperature in a mixture of ethanol and 2N sodium hydroxide (1:1) for 1 hour. The ethanol was evaporated and the aqueous residue was acidified with dilute hydrochloric acid to pH 3, extracted with dichloromethane, dried over magnesium sulphate and evaporated to a solid. This was recrystallised from dichloromethane/ether to give 8-(3,4-diphenylpyrazol-1-yl) octanoic acid (0.48 g, 13%) as colourless crystals, m.p. 114°–5° C. Found: C, 76.02; H, 7.25; N, 7.63%; $C_{23}H_{26}N_2O_2$ requires: C, 76.21; H, 7.23; N. 7.73% c) The mother liquor from above was evaporated to an oil which was chromatographed on silica gel (dichloromethane/methanol) giving a solid which was recrystallised from ether/petroleum ether to give 8-(4,5-diphenylpyrazol-1-yl) octanoic acid (0.15 g, 5%) as colourless crystals, m.p. 94°–5° C. Found: C, 76.53; H, 7.26; N, 7.82% $C_{23}H_{26}N_2O_2$ requires: C, 76.21; H, 7.23; N, 7.73%

EXAMPLE 68

2-(9-Hydroxynonyl)-4,5-diphenyl-1,2,3-triazole 4,5-Diphenyl-1,2,3-triazole was treated with 9-bromononan-1-ol and potassium carbonate in butanone to give after chromatography the title compound as a light brown oil.

Found: C, 76.0; H, 8.2; N, 11.2% $C_{23}H_{29}N_3O$ requires: C, 76.0; H, 8.0; N, 11.6%.

EXAMPLE 69

Ethyl 3-(3,4,5-triphenyl-2-oxo-2,3-dihydroimidazol-1-yl)propionate 1,4,5-Triphenylimidazole-2-one was treated with ethyl 3-bromo-propionate and potassium carbonate in butanone to give after work-up the title compound. m.p. 111°–112° C.

Found: C. 76.0;H, 5.9;N, 6.7%;$C_{26}H_{24}N_2O_3$ requires:C, 75.7;H, 5.9;N, 6.8%

EXAMPLES 70 & 71

Ethyl 5-(3,4,5-triphenyl-2-oxo-2,3-dihydroimidazol-1-yl)valerate; and Ethyl 5-(1,4,5-triphenylimidazol-2-yloxy)valerate 1,4,5-Triphenylimidazol-2-one was treated with ethyl 5-bromovalerate and potassium carbonate in butanone to give after chromatographic work-up ethyl 5-(3,4,5,-triphenyl-2-oxo 2,3-dihydroimidzol-1-yl)valerate. m.p. 78°–80° C., Found: C, 76.7;H, 6.6;N, 6.4%; $C_{28}H_{28}N_2O_3$ requires: C, 76.3;H, 6.4;N, 6.4% and ethyl 5-(1,4,5-triphenylimidazol-2-yloxy)valerate, m.p. 95°–96° C., Found: C, 76.5;H, 6.5; N, 6.3%; $C_{28}H_{28}N_2O_3$ requires: C, 76.3;H, 6.4;N,6.4%

EXAMPLE 72

Ethyl 6-(3-methyl-4,5-diphenyl-2-oxo-2,3-dihydroimidazol-1-yl)-5-hexanoate

1-Methyl-4,5-dipenylimidazol-2-one was treated with ethyl 6-bromo-hexanoate and potassium carbonate in butanone to give after work-up the title compound, m.p. 93°–94° C.

Found: C, 73.7;H, 7.1; N, 6.9%; $C_{24}H_{28}N_2O_3$ requires: C, 73.4; H, 7.2; N, 7.1%

EXAMPLE 73

Ethyl 8-(4,5-diphenyl-2-oxo-2,3-dihydroimidazol-1-yl)octanoate 4,5-Diphenylimidazol-2-one was treated with ethyl 8-bromooctanoate and potassium carbonate in butanone to give after work-up the title compound, m.p. 78°–79° C., Found:C, 73.7;H, 7.4;N, 6.7%;$C_{25}H_{30}N_2O_3$ requires: C, 73.9;H, 7.4;N, 6.9%

EXAMPLE 74

9-(3,4,5-Triphenyl-2-oxo-2,3-dihydroimidazol-1-yl) nonanoic acid 1,4,5-Triphenylimidazol-2-one was treated with ethyl 9-bromononanoate and potassium carbonate in butanone, followed by sodium hydroxide in ethanol and water, to give after work-up the title compound, m.p. 123°–124° C., Found:C, 76.9;H, 6.9;N, 5.7%;$C_{30}H_{32}N_2O_3$ requires: C, 76.9; H, 6.9; N, 6.0%

EXAMPLE 75

Methyl 7-(3,4,5-triphenyl-2-oxo-2,3-dihydroimidazol-1-yl)-5-heptynoate 1,4,5-Triphenylimidazol-2-one was treated with methyl 7-bromo-5-heptynoate and potassium carbonate in butanone to give after work-up the title compound, m.p. 133°–134° C., Found: C, 76.9; H, 5.8; N, 6.0%; $C_{29}H_{26}N_2O_3$ requires: C 77.3; H, 5.8; N, 6.2%

EXAMPLE 76

Ethyl 8-(4-phenylimidazol-1-yl)octanoate

4-Phenylimidazole was treated with ethyl 8-bromooctanoate and potassium carbonate in butanone to give after work-up the title compound, m.p. 56°–57° C., Found: C, 72.8; H, 8.4; N, 9.0%; $C_{19}H_{26}N_2O_2$ Requires: C, 72.6; H, 8.3;N, 8.9%

EXAMPLE 77

8-(4–5-Diphenylimidazol-2-ylthio)octanoic acid 4,5-Diphenyl-2-imidazolethiol was treated with ethyl 8-bromooctanoate and potassium carbonate in butanone, followed by sodium hydroxide in ethanol and water, to give after work-up the title compound, m.p. 154°–156° C., Found: C, 70.0;H, 6.4;N, 7.2;S, 7.9%; $C_{23}H_{26}N_2O_2S$ Requires: C, 70.0; H, 6.6; N, 7.1; S, 8.1%

EXAMPLE 78 & 79

11-(2,3-Diphenylmaleimido)undecanoic acid; and 8-(2,3-Diphenylmaleimido)undecanoic acid 2,3-Diphenylmaleic anhydride was treated with 11-aminoundecanoic acid and triethylamine in toluene at reflux temperature to give after work-up the title compound, m.p. 124°–125° C., Found: C, 74.5; H, 7.1; N, 3.2% $C_{27}H_{31}NO_4$; requires: C, 74.8; H, 7.2; N, 3.2%.

and in a similar manner with 8-aminoundecanoic acid yields m.p. 107°–108° C., Found C,73.7;H, 6.6; N, 3.5; $C_{24}H_{25}NO_4$ requires: C, 73.6; H, 6.5, N 3.6%.

EXAMPLE 80

8-(1,4,5-Triphenylimidazol-2-yloxy)octanoic acid 1,4,5-Triphenyl-2-chloroimidazole was treated with 8-hydroxyoctanoic acid and sodium hydride in dimethylformamide to give the title compound, m.p. 158°–159° C., Found: C, 75.3; H, 6.6;N, 6.0%; $C_{29}H_{30}N_2O_3 \cdot 0.43H_2O$ Requires: C, 75.3;H, 6.7; N, 6.0%

EXAMPLE 81

Ethyl 6-(3,4,5-triphenyl-2-oxo-2,3-dihydroimidazol-1-yl)hexanoate

A mixture of 1,4,5 triphenylimidazole (6.24 g), ethyl 6-bromohexanoate (13.38 g), potassium carbonate (13.2 g) and 2-butanone was stirred at reflux for 6 hours. The mixture was filtered, and the filtrate was evaporated. The residue was chromatographed on silica gel eluted with ethanol-hexane to give the title compound (5.61 g) m.p. 104°–106° C. Found: C, 76.35; H, 6.58; N, 6.07%; ($C_{29}H_{30}N_2O_2O_3$) Requires: C, 76.63; H, 6.65; N, 6.16%

EXAMPLE 82

8-(1,4,5-Triphenylimidazol-2-yloxy)octanamide 8-(1,4,5-Triphenylimidazol-2-yloxy)octanoic acid was treated with thionyl chloride followed by ammonia to give the title compound, m.p. 152.5°–153.5° C., Found: C, 76.6; H, 7.0; N, 9.1%: $C_{29}H_{31}N_3O_2$ requires: C, 76.8; H, 6:9; N, 9.3%

EXAMPLE 83

11-(3,4,5-Triphenyl-2-oxo-1,2-dihydroimidazol-1-yl)undecanoic acid 1,4,5-Triphenylimidazol-2-one was treated with ethyl 9-bromo-undecanoate and potassium carbonate in butanone, followed by sodium hydroxide in ethanol and water, to give after work-up the title compound, m.p. 83°–84° C. Found: C, 77.5; H, 7.3; N, 5.4%; $C_{32}H_{36}N_2O_3$ requires: C, 77.4; H, 7.3; N, 5.6%

The remaining compounds disclosed herein can be produced in an analagous manner to Examples 1 to 83 as described above or are readily ascertainable to one skilled in the art.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent Therefore, the Examples herein are to be construed as merely illustrative and not a limitation of the scope of the present invention in any way. The embodiments of the invention in which an exclusive property or privilege is claimed are defined as follows.

What is claimed is:

1. A method for treating an inflammatory component of a disease or disorder mediated by the lipid inflammatory mediators, arachidonic acid, its metabolites and/or platelet activating factor (PAF), which method comprises administering to a mammal in need thereof an effective amount of a compound which inhibits lipid mediator production by blocking the production, activation or action of Coenzyme A-independent transacylase (CoA-IT).

2. The method according to claim 1 wherein the disease or disorder is allergic rhinitis, asthma, myocardial infarction, stroke, circulatory shock, hypotension, ischemia, reperfusion injury, arthritis, inflammatory bowel disease, Crohn's disease, ulcerative colitis, asthma, adult respiratory distress syndrome, analphylaxis, shock, endotoxic shock, actinic keratosis, psoriasis, contact dermatitis, pyresis, or any other disease, disorder or syndrome mediated in some part by the lipid inflammatory mediators.

3. A method for treating disease or disorders mediated by the lipid inflammatory mediators, arachidonic acid, its metabolites and/or platelet activating factor (PAF), which method comprising administering to a mammal in need thereof an effective Coenzyme A independent transacylase (CoA-IT) inhibiting amount of a compound of the formula

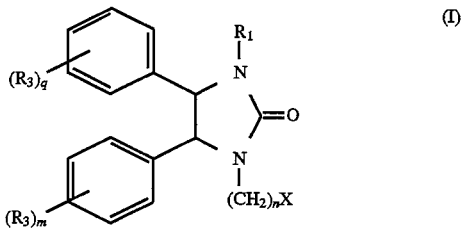

wherein $R_1$ is hydrogen, $C_{1-4}$alkyl, optionally substituted phenyl or optionally substituted heteroaryl;

n is 4 to 12;

X is 5-tetrazolyl, $SO_3H$, $P(O)(OR_2)_2$, $P(O)(OH)_2$, or $P(O)(R_2)(OR_2)$;

$R_2$ is hydrogen or $C_{1-4}$alkyl;

$R_3$ is independently hydrogen, $C_{1-4}$alkyl, halo substituted $C_{1-4}$alkyl, halogen, hydroxy or C1-4 alkoxy;

m is a number having a value of 1 to 3;

q is a number having a value of 1 to 3;

or a pharmaceutically acceptable salt thereof.

4. The method according to claim 3 wherein the compound is

Diethyl-7-(3,4,5-triphenylimidazol-2-oxo-2,3-dihydroimidazol-1-yl)heptane phosphonate;

Ethyl-7-(3,4,5-triphenyl-2-oxo-2,3-dihydroimidazol-1-yl)methyl-phosphinate; or 7-(3,4,5-triphenyl-2-oxo-2,3-dihydroimidazol-1-yl) heptanephosphonate.

5. A compound which is

Diisopropyl-7-(3,4,5-triphenyl-2-oxo-2,3-dihydroimidazol-1-yl)heptanephosphonate;

Dimethyl-7-(3,4,5-triphenyl-2-oxo-2,3-dihydroimidazol-1-yl) heptanephosphonate;

Diethyl-6-(3,4,5-triphenyl-2-oxo-2,3-dihydroimidazol-1-yl)hexanephosphonate;

Diethyl-8-(3,4,5-triphenyl-2-oxo-2,3-dihydroimidazol-1-yl)octanephosphonate; or a pharmacuetically acceptable salt thereof.

6. A pharmaceutical composition comprising a pharmaceutically acceptable diluent or carrier and a compound selected from the group consisting of:

Diisopropyl-7-(3,4,5-triphenyl-2-oxo-2,3-dihydroimidazol-1-yl)heptanephosphonate;

Dimethyl-7-(3,4,5-triphenyl-2-oxo-2,3-dihydroimidazol-1-yl)heptanephosphonate;

Diethyl-6-(3,4,5-triphenyl-2-oxo-2,3-dihydroimidazol-1-yl)hexanephosphonate; and Diethyl-8-(3,4,5-triphenyl-2-oxo-2,3-dihydroimidazol-1-yl)octanephosphonate; or a pharmacuetically acceptable salt thereof.

7. The method according to claim 3 or 4 wherein the disease or disorder is allergic rhinitis, asthma, myocardial infarction, stroke, circulatory shock, hypotension, ischemia, reperfusion injury, arthritis, inflammatory bowel disease, Crohn's disease, ulcerative colitis, asthma, adult respiratory distress syndrome, analphylaxis, shock, endotoxic shock, actinic keratosis, psoriasis, contact dermatitis, or pyresis.

8. A method for treating disease or disorders mediated by the lipid inflammatory mediators, arachidonic acid, its metabolites and/or platelet activating factor (PAF), which method comprising administering to a mammal in need thereof an effective Coenzyme A independent transacylase (CoA-IT) inhibiting amount of a compound of the formula

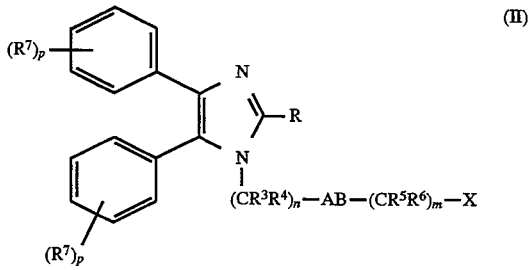

wherein

R is hydrogen, $C_{1-8}$alkyl, $C_{1-8}$alkoxy, $SC_{1-8}$alkyl, optionally substituted phenyl, phenyl $C_{1-4}$alkyl in which the phenyl group is optionally substituted, $C_{1-6}$alkylCHO or $C_{1-6}$alkylCH(OR$^1$)(OR$^2$) in which each group R$^1$ and $R^2$ is $C_{1-4}$alkyl, or together form an ethane 1,2-diyl or propane 1,3-diyl group;

n is an integer having a value of 2 to 6;

m is an integer having a value of 0 to 6;

p is an integer having a value of 1 to 3;

$R^3$, $R^4$, $R^5$ and $R^6$ are independently hydrogen or $C_{1-4}$alkyl;

AB is a bond, —CH=CH—, —S—, S-phenyl or O-phenyl;

X is $CO_2H$ or a group hydrolysable to $CO_2H$, 5-tetrazolyl, $SO_3H$, $P(O)(OR)_2$, $P(O)(OH)_2$, or $P(O)(R)(OR)$ in which R is hydrogen or $C_{1-4}$alkyl;

$R^7$ is hydrogen, $C_{1-4}$alkyl, halo$C_{1-4}$alkyl, halogen, hydroxy, or $C_{1-4}$alkoxy;

or a pharmaceutically acceptable salt thereof; provided that:

a) when X is 5-tetrazolyl, $R^7$ is hydrogen, R is phenyl, and AB is a bond, then n+m are equal to a number greater than 6;

b) when X is $CO_2H$, AB is a bond, n+m is equal to 7, and $(R^7)p$ is the same and is hydrogen, then R is not hydrogen;

c) when X is $CO_2H$, AB is a bond, n+m is equal to 7, and $(R^7)p$ is the same and is hydrogen, then R is not alkyl or hydrogen;

d) when X is $CO_2H$, AB is a bond, n+m is equal to 7, and $(R^7)p$ is the same and is 4-hydroxy, then R is not phenyl;

e) when X is $CO_2H$, AB is a bond, n+m is equal to 7, and $(R^7)p$ is the same and is 4-Methoxy or is 4-hydroxy, then R is not hydrogen;

f) when X is $CO_2H$, AB is a bond, n+m is equal to 7, and $(R^7)p$ is the same and is 2-chloro, then R is not hydrogen;

g) when $(R^7)p$ is the same and is hydrogen, R is phenyl, n is 4, m is 0, and AB is O-phenyl then X is not $CO_2$—$C_{1-6}$alkyl;

h) when R is hydrogen, $(R^7)p$ is the same and is hydrogen, AB is a bond, n+m is equal to 7, than X is not $CH_3O$—$(CH_2)_2$—O—$(CH_2)_2$—O—C(O)—;

i) when X is $CO_2$—$C_{1-6}$alkyl, AB is a bond, n+m is equal to 7, and $(R^7)p$ is the same and is hydrogen, then R is not phenyl or 4-methoxyphenyl;

j) when X is $CO_2$—$C_{1-6}$alkyl, AB is a bond, n+m is equal to 7, and $(R^7)p$ is the same and is 4-bromo or 4-methoxy, then R is not hydrogen;

k) when X is $CO_2$—$C_{1-6}$alkyl, AB is a bond, n+m is equal to 7, and $(R^7)p$ is the same and is hydrogen, then R is not 2-(4-methoxybenzyl);

l) when $(R^7)p$ is the same and is hydrogen, R is phenyl, AB is a bond n+m is equal to 10, then X is not $CO_2$—$C_{1-6}$alkyl;

m) when $(R^7)p$ is the same and is hydrogen, R is phenyl, n is 4, m is 0 and AB is O-phenyl, then X is not $CO_2$—$C_{1-6}$alkyl;

n) when AB is —S—, n is 5 or 6, then m is 1 and X is $CO_2H$;

or a pharmaceutically acceptable salt thereof.

9. The method according to claim 8 wherein the compound is 1-(7-Carboxyheptyl)-2-heptyl-4,5-diphenylimidazole;

1-(7-(5-Tetrazolylheptyl)-2,4,5-triphenylimidazole;

1-(10-Carboxydecyl)-2,4,5-triphenylimidazole;

4-[4-(2,4,5-triphenylimidazolyl)butyloxy]benzoic acid;

9-(1,2,4-tri-phenylimidazolyl)-2,2-dimethylnonanoic acid;

1-(8-Carboxyoctyl)-2,4,5-triphenylimidazole;

1-(7-Carboxy-heptyl)-2-(4-hydroxy-3,5-diiodophenyl)-4,5-diphenylimidazole;

Ethyl 8-(4,5-diphenylimidazol-1-yl)octanoate;

1-(7-Ethoxycarbonylheptyl)-2-methyl-4,5-diphenylimidazole; or 1-(7-Carboxyheptyl)-2-(4-hydroxyphenyl)-4,5-diphenylimidazole.

10. The method according to claim 8 or 9 wherein the disease or disorder is allergic rhinitis, asthma, myocardial infarction, stroke, circulatory shock, hypotension, ischemia, reperfusion injury, arthritis, inflammatory bowel disease, Crohn's disease, ulcerative colitis, asthma, adult respiratory distress syndrome, analphylaxis, shock, endotoxic shock, actinic keratosis, psoriasis, contact dermatitis, pyresis, or any other disease, disorder or syndrome mediated in some part by the lipid inflammatory mediators.

11. A method for treating disease or disorders mediated by the lipid inflammatory mediators, arachidonic acid, its metabolites and/or platelet activating factor (PAF), which method comprising administering to a mammal in need thereof an effective Coenzyme A independent transacylase (CoA-IT) inhibiting amount of a compound of the formula

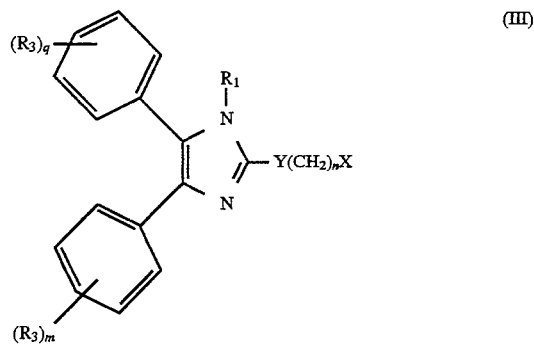

(III)

wherein $R_1$ is hydrogen, $C_{1-4}$alkyl, optionally substituted phenyl or optionally substituted heteroaryl;

n is an integer having a value of 4 to 12;

Y is oxygen or sulfur;

X is 5-tetrazolyl, $SO_3H$, $P(O)(OR_2)_2$, $P(O)(OH)_2$, or $P(O)(R_2)(OR_2)$;

$R_2$ is hydrogen or $C_{1-4}$alkyl;

$R_3$ is independently $C_{1-4}$alkyl, halo substituted $C_{1-4}$alkyl, halogen, hydroxy or C1–4 alkoxy;

m is an integer having a value of 1 to 3;

q is an integer having a value of 1 to 3;

or a pharmaceutically acceptable salt thereof.

12. The method according to claim 11 wherein the compound is

Ethyl-7-(1,4,5-triphenyl-imidazol-2-yl-oxy)heptane methylphosphinate;or

Diethyl-7-(1,4,5-triphenyl-imidazol-2-yl-oxy) heptanephosphonate.

13. The method according to claim 11 or 12 wherein the disease or disorder is allergic rhinitis, asthma, myocardial infarction, stroke, circulatory shock, hypotension, ischemia, reperfusion injury, arthritis, inflammatory bowel disease, Crohn's disease, ulcerative colitis, asthma, adult respiratory distress syndrome, analphylaxis, shock, endotoxic shock, actinic keratosis, psoriasis, contact dermatitis, pyresis, or any other disease, disorder or syndrome mediated in some part by the lipid inflammatory mediators.

14. A method for treating disease or disorders mediated by the lipid inflammatory mediators, arachidonic acid, its metabolites and/or platelet activating factor (PAF), which method comprising administering to a mammal in need thereof an effective Coenzyme A independent transacylase (CoA-IT) inhibiting amount of a compound of the formula

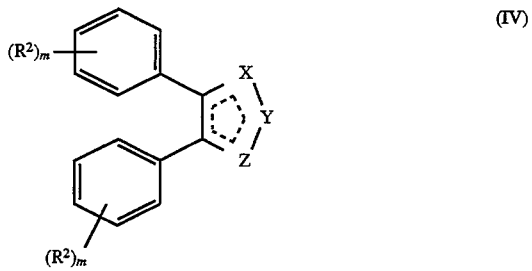

(IV)

wherein

X is nitrogen or $CR^1$;

$R^1$ is hydrogen, $C_{1-4}$alkyl, optionally substituted phenyl or optionally substituted heteroaryl;

Y is nitrogen, $N(CH_2)_nA$ or $C(CH_2)_nA$

Z is nitrogen, oxygen or $N(CH_2)_nA'$, and the dotted line indicates the optional presence of a double bond so as to form a fully unsaturated heterocyclic ring;

n is an integer having a value of 4 to 12;

A' is $CO_2H$ or a group hydrolysable to $CO_2H$, 5-tetrazolyl, $SO_3H$, $P(O)(OR)_2$, $P(O)(OH)_2$, or $P(O)(R)(OR)$ in which R is hydrogen or $C_{1-4}$alkyl;

A is $CO_2H$ or a group hydrolysable to $CO_2H$, OH, Br, Cyano, 5-tetrazolyl, $SO_3H$, $P(O)(OR)_2$, $P(O)(OH)_2$, or $P(O)(R)(OR)$ in which R is hydrogen or $C_{1-4}$alkyl;

$R^2$ is independently $C_{1-4}$alkyl, halo substituted $C_{1-4}$alkyl, halogen, hydroxy or $C_{1-4}$alkoxy;

m is an integer having a value of 1 to 3; provided that a) X, Y and Z are not all at the same time, nitrogen;
b) when X is $CR^1$, Y and Z are not both nitrogen;
c) when Y is $N(CH_2)_nA$, Z is nitrogen; and
d) when Z is oxygen, Y is $C(CH_2)_nA$;
e) when Y is $N(CH_2)_nA$, X and Z are nitrogen, $(R_2)_m$ is the same and is hydrogen, and n is 6, 7, or 8 then X is not —$CO_2$—$C_{1-6}$alkyl;
f) when Z is oxygen, Y is $C(CH_2)_nA$, n is 8, and $(R_2)_m$ is the same and is hydrogen, then X is not cyano;
g) when Z is $N(CH_2)_nA'$, X is nitrogen, Y is nitrogen, $(R_2)_m$ is the same and is hydrogen, and n is 7, then X is not $CO_2H$;
h) when Y is $N(CH_2)_nA$, X and Z are nitrogen, $(R_2)_m$ is the same and is hydrogen, and n is 8 then X is not cyano;

or a pharmaceutically acceptable salt thereof.

15. The method according to claim 14 wherein the compound is 1-(8-Bromooctyl)-4,5-diphenyltriazole;

2-(8-Cyanooctyl)-4,5-diphenyl-triazole;

8-(3,4-Diphenylpyrazol-1-yl)octanoic acid;

2-(9-Hydroxynonyl)-4,5-diphenyl-1,2, 3-triazole 2-(7-Methoxycarbonylheptyl)-4,5-diphenyltriazole 8-(3,4-Diphenylpyrazol-1-yl)octanoic acid;

8-(4,5-Diphenylpyrazol-1-yl)octanoic acid;

2-(6-Carboxyhexyl)-4,5-triphenyltriazole; or 2-(7-Carboxyheptyl)-4,5-diphenyloxazole.

16. The method according to claim 14 or 15 wherein the disease or disorder is allergic rhinitis, asthma, myocardial infarction, stroke, circulatory shock, hypotension, ischemia, reperfusion injury, arthritis, inflammatory bowel disease, Crohn's disease, ulcerative colitis, asthma, adult respiratory distress syndrome, analphylaxis, shock, endotoxic shock, actinic keratosis, psoriasis, contact dermatitis, pyresis, or any other disease, disorder or syndrome mediated in some past by the lipid inflammatory mediators.

17. A method for treating disease or disorders mediated by the lipid inflammatory mediators, arachidonic acid, its metabolites and/or platelet activating factor (PAF), which method comprising administering to a mammal in need thereof an effective Coenzyme A independent transacylase (CoA-IT) inhibiting amount of a compound of the Formula

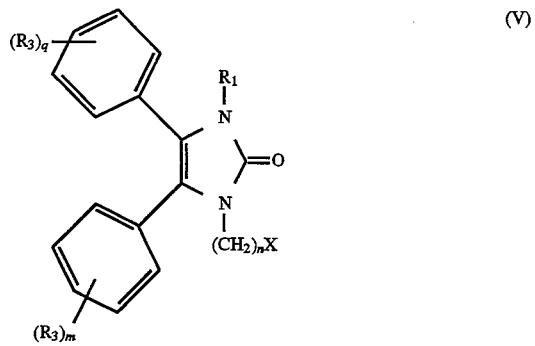

(V)

wherein $R_1$ is hydrogen, $C_{1-4}$alkyl, or optionally substituted phenyl;

n is 2 or 4 m 12;

X is cyano, $CO_2H$ or a group hydrolysable to $CO_2H$;

$R_3$ is independently $C_{1-4}$alkyl, halo substituted $C_{1-4}$alkyl, halogen, hydroxy or $C_{1-4}$alkoxy;

q is an integer having a value of 1 to 3;

or a pharmaceutically acceptable salt thereof.

18. The method according to claim 17 wherein the compound is:

Ethyl 3-(3,4,5-triphenyl-2-oxo-2,3-dihydroimidazol-1-yl) propionate;

Ethyl 6-(3,4,5-triphenyl-2-oxo-2,3-dihydroimidazol-1-yl) hexanoate;

Ethyl 5-(3,4,5-triphenyl-2-oxo-2,3-dihydroimidazol-1-yl) valerate;

9-[1-(3,4,5-Triphenyl-2-oxo-2,3-dihydroimidazolyl)] nonanoic acid;

7-(3,4,5-Triphenyl-2-oxo-1,2-dihydroimidazol-1-yl) heptanitrile;

Ethyl 6-(3-methyl-4,5-diphenyl-2-oxo-2,3-dihydroimidazol-1-yl)hexanoate;

11-(3,4,5-Triphenyl-2-oxo-1,2-dihydroimidazol-1-yl) undecanoic acid; or

Ethyl-8-(4,5-diphenyl-2-oxo-2,3-dihydroimidazol-1-yl) octanoate.

19. The method according to claims 17 or 18 wherein the disease or disorder is allergic rhinitis, asthma, myocardial infarction, stroke, circulatory shock, hypotension, ischemia, reperfusion injury, arthritis, inflammatory bowel disease, Crohn's disease, ulcerative colitis, asthma, adult respiratory distress syndrome, analphylaxis, shock, endotoxic shock, actinic keratosis, psoriasis, contact dermatitis, pyresis, or any other disease, disorder or syndrome mediated in some part by the lipid inflammatory mediators.

20. A method for treating disease or disorders mediated by the lipid inflammatory mediators, arachidonic acid, its metabolites and/or platelet activating factor (PAF), which method comprising administering to a mammal in need thereof an effective Coenzyme A independent transacylase (CoA-IT) inhibiting amount of a compound of the Formula:

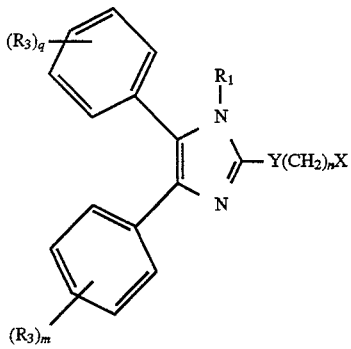

(VI)

wherein $R_1$ is hydrogen, $C_{1-4}$alkyl, or optionally substituted phenyl;

n is 4 to 12;

Y is oxygen or sulfur;

X is $CO_2H$ or a group hydrolysable to $CO_2H$;

$R_3$ is independently $C_{1-4}$alkyl, halo substituted $C_{1-4}$alkyl, halogen, hydroxy or $C_{1-4}$alkoxy;

q is an integer having a value of 1 to 3;

or a pharmaceutically acceptable salt thereof.

21. The method according to claim 20 wherein the compound is

Ethyl 5-(1,4,5-triphenylimidazol-1-yl-oxy)valerate;

8-(1,4,5-Triphenylimidazol-2-yl-oxy)octanamide;

8-[1,4,5-Triphenylimidazol-2-yl-oxy]octanoic acid; or

8-[1,4,5-triphenylimidazol-2-yl-oxy]octanoic acid ammonium salt.

22. The method according to claim 20 or 21 wherein the disease or disorder is allergic rhinitis, asthma, myocardial infarction, stroke, circulatory shock, hypotension, ischemia, reperfusion injury, arthritis, inflammatory bowel disease, Crohn's disease, ulcerative colitis, asthma, adult respiratory distress syndrome, analphylaxis, shock, endotoxic shock, actinic keratosis, psoriasis, contact dermatitis, pyresis, or any other disease, disorder or syndrome mediated in some part by the lipid inflammatory mediators.

23. A method for treating disease or disorders mediated by the lipid inflammatory mediators, arachidonic acid, its metabolites and/or platelet activating factor (PAF), which method comprising administering to a mammal in need thereof an effective Coenzyme A independent transacylase (CoA-IT) inhibiting amount of a compound selected from 7-(3,4,5-Triphenylimidazol-1-yl-oxy)heptanitrile;

8-(2,3-Diphenylmaleimido)octanoic acid;

11-(2,3-Diphenylmaleimido)undecanoic acid;

1-(7-Ethoxycarbonyl)-4-phenylimidazole;

Methyl-7-(3,4,5-triphenyl)-2-oxo-1,2-dihydroimidazol-1-yl)-5-heptynoate;

2-[4-(3-Carboxypropoxy)phenyl]-4,5-diphenylimidazole;

1-(7-Carboxyheptyl)-2-phenylimidazole;

1-(7-Ethoxycarbonyl)-4-phenylimidazole;

1-(7-Carboxyheptyl)-2-octylthio-4,5,-diphenylimidazole;

8-(1,4,5-Triphenylimidazol-2-yl-oxy)octanamide; and the pharmaceutically acceptable salts thereof.

24. The method according to claim 23 wherein the compound is 1-(7-Carboxyheptyl)-2-octylthio-4,5,-diphenylimidazole;

8-[1,4,5-Triphenylimidazol-2-yl-oxy]octanoic acid;

Ethyl 5-(3,4,5-triphenyl-2-oxo-2,3-dihydroimidazol-1-yl)valerate;

Ethyl 3-(3,4,5-triphenyl-2-oxo-2,3-dihydroimidazol-1-yl)propionate;

Ethyl 6-(3,4,5-triphenyl-2-oxo-2,3-dihydroimidazol-1-yl)hexanoate;

7-(3,4,5-Triphenylimidazol-2-oxo-2,3-dihydroimidazol-1-yl)heptanonitrile;

Ethyl 6-(3-methyl-4,5-diphenyl-2-oxo-2,3-dihydroimidazol-1-yl)hexanoate;

1-(7-Ethoxycarbonyl)-4-phenylimidazole; and

Methyl-7-(3,4,5-triphenyl)-2-oxo-1,2-dihydroimidazol-1-yl)-5-heptynoate.

25. The method according to claims 23 or 34 wherein the disease or disorder is allergic rhinitis, asthma, myocardial infarction, stroke, circulatory shock, hypotension, ischemia, reperfusion injury, arthritis, inflammatory bowel disease, Crohn's disease, ulcerative colitis, asthma, adult respiratory distress syndrome, analphylaxis, shock, endotoxic shock, actinic keratosis, psoriasis, contact dermatitis, pyresis, or any other disease, disorder or syndrome mediated in some part by the lipid inflammatory mediators.

26. The compound which is 1-(7-Carboxyheptyl)-2-octylthio-4,5,-diphenylimidazole;

8-(2,3-Diphenylmaleimido)octanoic acid;

11-(2,3-Diphenylmaleimido)undecanoic acid;

1-(7-Ethoxycarbonyl)-4-phenylimidazole;

7-(3,4,5-Triphenylimidazol-2-oxo-2,3-dihydroimidazol-1-yl)heptanonitrile;

Ethyl 3-(3,4,5-triphenyl-2-oxo-2,3-dihydroimidazol-1-yl)propionate;

Ethyl 6-(3,4,5-triphenyl1,2-oxo-2,3-dihydroimidazol-1-yl)hexanoate;

Ethyl 5-(3,4,5-triphenyl-2-oxo-2,3-dihydroimidazol-1-yl)valerate;

9-[1-(3,4,5-Triphenyl-2-oxo-2,3-dihydroimidazolyl)]nonanoic acid;

Ethyl 6-(3-methyl-4,5-diphenyl-2-oxo-2,3-dihydroimidazol-1-yl)hexanoate;

Ethyl-8-(4,5-diphenyl-2-oxo-2,3-dihydroimidazol-1-yl)octanoate;

7-(3,4,5-Triphenyl-2-oxo-1,2-dihydroimidazol-1-yl)heptanitrile; or

Methyl-7-(3,4,5-triphenyl)-2-oxo-1,2-dihydroimidazol-1-yl)-5-heptynoate.

27. The compound according to claim 26 which is 1-(7-Carboxyheptyl)-2-octylthio-4,5-diphenylimidazole; or Ethyl 5-(3,4,5-triphenyl-2-oxo-2,3-dihydroimidazol-1-yl)valerate.

28. A pharmaceutical composition comprising a pharmaceutically acceptable diluent or carrier and a compound selected from the group consisting of:

1-(7-Carboxyheptyl)-2-octylthio-4,5,-diphenylimidazole;

8-(2,3-Diphenylmaleimido)octanoic acid;

11-(2,3-Diphenylmaleimido)undecanoic acid;

1-(7-Ethoxycarbonyl)-4-phenylimidazole;

7-(3,4,5-Triphenylimidazol-2-oxo-2,3-dihydroimidazol-1-yl)heptanonitrile;

Ethyl 3-(3,4,5-triphenyl-2-oxo-2,3-dihydroimidazol-1-yl)propionate;

Ethyl 6-(3,4,5-triphenyl-2-oxo-2,3-dihydroimidazol-1-yl)hexanoate;

Ethyl 5-(3,4,5-triphenyl-2-oxo-2,3-dihydroimidazol-1-yl)valerate;

9-[1-(3,4,5-Triphenyl-2-oxo-2,3-dihydroimidazolyl)]nonanoic acid;

Ethyl 6-(3-methyl-4,5-diphenyl-2-oxo-2,3-dihydroimidazol-1-yl)hexanoate;

Ethyl-8-(4,5-diphenyl-2-oxo-2,3-dihydroimidazol-1-yl)octanoate;

7-(3,4,5-Triphenyl-2-oxo-1,2-dihydroimidazol-1-yl)heptanitrile; or

Methyl-7-(3,4,5-triphenyl)-2-oxo-1,2-dihydroimidazol-1-yl)-5-heptynoate.

29. The compound according to claim 28 which is 1-(7-Carboxyheptyl)-2-octylthio-4,5-diphenylimidazole; or Ethyl 5-(3,4,5-triphenyl-2-oxo-2,3-dihydroimidazol-1-yl)valerate.

30. The method according to claim 2 wherein the disease or disorder is allergic rhinitis, asthma, myocardial infarction, stroke, circulatory shock, hypotension, ischemia, reperfusion injury, arthritis, inflammatory bowel disease, Crohn's disease, ulcerative colitis, asthma, adult respiratory distress syndrome, analphylaxis, shock, endotoxic shock, actinic keratosis, psoriasis, contact dermatitis, pyresis, or any other disease, disorder or syndrome in which a significant increase in the amount, or production of, a lipid inflammatory mediator, arachidonic acid, its metabolites, and/or platelet activating factor occurs.

* * * * *